(12) United States Patent
Verhoest et al.

(10) Patent No.: US 7,429,665 B2
(45) Date of Patent: Sep. 30, 2008

(54) HETEROAROMATIC QUINOLINE COMPOUNDS

(75) Inventors: Patrick R. Verhoest, Old Lyme, CT (US); Christopher J. Helal, East Lyme, CT (US); Dennis J. Hoover, Mysic, CT (US); John M. Humphrey, Mystic, CT (US)

(73) Assignee: Pfizer Inc, New York, NY (US)

( * ) Notice: Subject to any disclaimer, the term of this patent is extended or adjusted under 35 U.S.C. 154(b) by 180 days.

(21) Appl. No.: 11/326,221

(22) Filed: Jan. 5, 2006

(65) Prior Publication Data

US 2006/0154931 A1 Jul. 13, 2006

Related U.S. Application Data

(60) Provisional application No. 60/642,058, filed on Jan. 7, 2005.

(51) Int. Cl.
*C07D 215/00* (2006.01)
*A01N 43/42* (2006.01)

(52) U.S. Cl. ...................... 546/152; 514/314
(58) Field of Classification Search ................. 546/152; 514/314
See application file for complete search history.

(56) References Cited

U.S. PATENT DOCUMENTS

| 4,681,940 A | 7/1987 | Musser et al. | |
|---|---|---|---|
| 4,876,346 A | 10/1989 | Musser et al. | |
| 5,500,427 A | 3/1996 | Kubo et al. | 514/256 |
| 5,693,652 A * | 12/1997 | Takase et al. | 514/322 |
| 5,843,958 A | 12/1998 | Ferro et al. | |
| 7,250,518 B2 | 7/2007 | Magee et al. | 546/284.1 |
| 2006/0111368 A1 | 5/2006 | Osakada et al. | 514/253.06 |

FOREIGN PATENT DOCUMENTS

| WO | WO 93/16071 A1 | 8/1993 |
|---|---|---|
| WO | WO03/000269 A | 1/2003 |
| WO | WO03/014115 A | 2/2003 |
| WO | WO03/093499 A | 11/2003 |
| WO | WO 2005/019211 A | 3/2005 |
| WO | WO2005/120514 A | 12/2005 |

OTHER PUBLICATIONS

Musser, John H.; Kubrak, Dennis M.; Bender, Reinhold H. W.; Kreft, Anthony F.; Nielsen, Susan T.; Lefer, Allan M.; Chang, Joseph; Lewis, Alan J.; Hand, James M. Wyeth Lab., Inc., Philadelphia, PA, 19104, USA "Phenylephrine derivatives as leukotriene D4 antagonists" Journal of Medicinal Chemistry (1987), 30(11), 2087-93 CODEN: JMCMAR; ISSN: 0022-2623.
Victor Segarra, Phosphodiesterase inhibitory properties of losartin. Design and synthesis of new lead compounds, Bioorganic & Medicinal Chemistry Letters (1998), vol. 8, No. 5, pp. 505-510.

* cited by examiner

*Primary Examiner*—Rita Desai
*Assistant Examiner*—John Mabry
(74) *Attorney, Agent, or Firm*—Steve T. Zelson; Christian M. Smolizza

(57) ABSTRACT

The invention pertains to heteroaromatic compounds that serve as effective phosphodiesterase (PDE) inhibitors. In particular, the invention relates to said compounds which are selective inhibitors of PDE10. The invention also relates to intermediates for preparation of said compounds; pharmaceutical compositions comprising said compounds; and the use of said compounds in a method for treating certain central nervous system (CNS) or other disorders.

9 Claims, No Drawings

HETEROAROMATIC QUINOLINE COMPOUNDS

CROSS REFERENCE TO RELATED APPLICATION

The present application claims benefit of U.S. Ser. No. 60/642,058 filed on Jan. 7, 2005 which is incorporated by reference herein in its entirety.

FIELD OF THE INVENTION

The invention pertains to heteroaromatic compounds that serve as effective phosphodiesterase (PDE) inhibitors. The invention also relates to compounds which are selective inhibitors of PDE10. The invention further relates to intermediates for preparation of such compounds; pharmaceutical compositions comprising such compounds; and the use of such compounds in methods for treating certain central nervous system (CNS) or other disorders. The invention relates also to methods for treating neurodegenerative and psychiatric disorders, for example psychosis and disorders comprising deficient cognition as a symptom.

BACKGROUND OF INVENTION

Phosphodiesterases (PDEs) are a class of intracellular enzymes involved in the hydrolysis of the nucleotides cyclic adenosine monophosphate (cAMP) and cyclic guanosine monophosphates (cGMP) into their respective nucleotide monophosphates. The cyclic nucleotides cAMP and cGMP are synthesized by adenylyl and guanylyl cyclases, respectively, and serve as secondary messengers in several cellular pathways.

The cAMP and cGMP function as intracellular second messengers regulating a vast array of intracellular processes particularly in neurons of the central nervous system. In neurons, this includes the activation of cAMP and cGMP-dependent kinases and subsequent phosphorylation of proteins involved in acute regulation of synaptic transmission as well as in neuronal differentiation and survival. The complexity of cyclic nucleotide signaling is indicated by the molecular diversity of the enzymes involved in the synthesis and degradation of cAMP and cGMP. There are at least ten families of adenylyl cyclases, two of guanylyl cyclases, and eleven of phosphodiesterases. Furthermore, different types of neurons are known to express multiple isozymes of each of these classes, and there is good evidence for compartmentalization and specificity of function for different isozymes within a given neuron.

A principal mechanism for regulating cyclic nucleotide signaling is by phosphodiesterase-catalyzed cyclic nucleotide catabolism. There are 11 known families of PDEs encoded by 21 different genes. Each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE families or isozymes may offer particular therapeutic effects, fewer side effects, or both.

PDE10 is identified as a unique family based on primary amino acid sequence and distinct enzymatic activity. Homology screening of EST databases revealed mouse PDE10A as the first member of the PDE10 family of PDEs (Fujishige et al., J. Biol. Chem. 274:18438-18445, 1999; Loughney, K. et al., Gene 234:109-117, 1999). The murine homologue has also been cloned (Soderling, S. et al., Proc. Natl. Acad. Sci. USA 96:7071-7076, 1999) and N-terminal splice variants of both the rat and human genes have been identified (Kotera, J. et al., Biochem. Biophys. Res. Comm. 261:551-557, 1999; Fujishige, K. et al., Eur. J. Biochem. 266:1118-1127, 1999). There is a high degree of homology across species. The mouse PDE10A1 is a 779 amino acid protein that hydrolyzes both cAMP and cGMP to AMP and GMP, respectively. The affinity of PDE10 for cAMP ($Km=0.05$ μM) is higher than for cGMP ($Km=3$ μM). However, the approximately 5-fold greater Vmax for cGMP over cAMP has lead to the suggestion that PDE10 is a unique cAMP-inhibited cGMPase (Fujishige et al., J. Biol. Chem. 274:18438-18445, 1999).

The PDE 10 family of polypeptides shows a lower degree of sequence homology as compared to previously identified PDE families and has been shown to be insensitive to certain inhibitors that are known to be specific for other PDE families. U.S. Pat. No. 6,350,603, incorporated herein by reference.

PDE10 also is uniquely localized in mammals relative to other PDE families. mRNA for PDE10 is highly expressed only in testis and brain (Fujishige, K. et al., Eur J Biochem. 266:1118-1127, 1999; Soderling, S. et al., Proc. Natl. Acad. Sci. 96:7071-7076, 1999; Loughney, K. et al., Gene 234:109-117, 1999). These initial studies indicated that within the brain PDE10 expression is highest in the striatum (caudate and putamen), n. accumbens, and olfactory tubercle. More recently, a detailed analysis has been made of the expression pattern in rodent brain of PDE10 mRNA (Seeger, T. F. et al., Abst. Soc. Neurosci. 26:345.10, 2000) and PDE10 protein (Menniti, F. S., Stick, C. A., Seeger, T. F., and Ryan, A. M., Immunohistochemical localization of PDE10 in the rat brain. William Harvey Research Conference 'Phosphodiesterase in Health and Disease', Porto, Portugal, Dec. 5-7, 2001).

A variety of therapeutic uses for PDE inhibitors has been reported including obtrusive lung disease, allergies, hypertension, angina, congestive heart failure, depression and erectile dysfunction (WO 01/41807 A2, incorporated herein by reference).

The use of selected benzimidazole and related heterocyclic compounds in the treatment of ischemic heart conditions has been disclosed based upon inhibition of PDE associated cGMP activity. U.S. Pat. No. 5,693,652, incorporated herein by reference.

United States Patent Application Publication No. 2003/0032579 discloses a method for treating certain neurologic and psychiatric disorders with the selective PDE10 inhibitor papaverine. In particular, the method relates to psychotic disorders such as schizophrenia, delusional disorders and drug-induced psychosis; to anxiety disorders such as panic and obsessive-compulsive disorder; and to movement disorders including Parkinson's disease and Huntington's disease.

SUMMARY OF THE INVENTION

The present invention provides for compounds of formula I or pharmaceutical salts thereof,

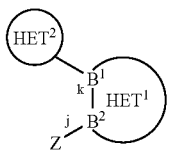

wherein Z is

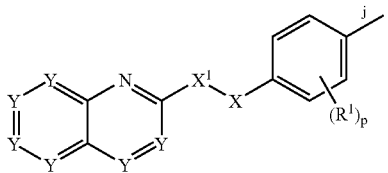

$R_1$ is each independently selected from a group consisting of hydrogen, halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_1$ to $C_8$ haloalkyl, $C_3$ to $C_8$ cycloalkyl, $C_3$ to $C_8$ cycloalkyl-$C_1$ to $C_8$ alkyl, 4 to 7 membered heterocycloalkyl, $C_1$ to $C_8$ alkylthio, —$NR^3R^3$, —O—$CF_3$, —$S(O)_n$—$R^3$, $C(O)$—$NR^3R^3$, and $C_1$ to $C_8$ alkyl substituted with a heteroatom wherein the heteroatom is selected from a group consisting of nitrogen, oxygen and sulfur and wherein the heteroatom may be further substituted with a substituent selected from a group consisting of hydrogen, $C_1$ to $C_8$ alkyl, $C_3$ to $C_8$ cycloalkyl, $C_2$ to $C_8$ alkenyl, $C_2$ to $C_8$ alkynyl, and $C_1$ to $C_8$ haloalkyl;

each $R^3$ is independently selected from a group consisting of hydrogen, $C_1$ to $C_8$ alkyl, $C_2$ to $C_8$ alkenyl, $C_2$ to $C_8$ alkynyl, $C_1$ to $C_8$ haloalkyl, $C_3$ to $C_8$ cycloalkyl;

$R^2$ is selected from the group consisting of hydrogen, $C_1$ to $C_8$ alkyl, $C_3$ to $C_8$ cycloalkyl-$C_1$ to $C_8$ alkyl, $C_2$ to $C_8$ alkenyl, $C_2$ to $C_8$ alkynyl, $C_1$ to $C_8$ haloalkyl and $C_3$ to $C_8$ cycloalkyl;

$HET^1$ is selected from a group consisting of a monocyclic heteroaryl and a bicyclic heteroaryl, wherein the monocyclic and bicyclic heteroaryl may be optionally substituted with at least one $R^4$ and;

$R^4$ is selected from a group consisting of halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_3$ to $C_8$ cycloalkyl, $C_3$ to $C_8$ cycloalkyl-$C_1$ to $C_8$ alkyl, $C_1$ to $C_8$ alkylthio, and $C_1$ to $C_8$ alkyl substituted with a substituent is selected from the group consisting of —$OR^8$, —$NR^8R^8$, and —$SR^8$, wherein $R^8$ is independently selected from the group consisting of hydrogen and $C_1$ to $C_8$ alkyl $HET^2$ is a monocyclic or bicyclic heteroaryl, wherein the monocyclic and bicyclic heteroaryl optionally substituted with at least one $R^5$, with the proviso that $HET^2$ is not tetrazole;

$R^5$ is independently selected from a group consisting of halogen, hydroxyl, cyano, $C^1$ to $C_8$ alkyl, $C_2$ to $C_8$ alkenyl, $C_2$ to $C_8$ alkynyl, $C_1$ to $C_8$ alkoxy, $C_3$ to $C_8$ cycloalkyl, $C_3$ to $C_8$ cycloalkyl-$C_1$ to $C_8$ alkyl, $C_1$ to $C_8$ alkylthio, —$NR^7R^7$ and $C_1$ to $C_8$ haloalkyl;

$B^1$ and $B^2$ are adjacent atoms in $Het^1$ which are independently selected from a group consisting of carbon and nitrogen;

bond j is a covalent bond between Z and $B^2$;

bond k is a covalent bond in $Het^1$ between $B^1$ and $B^2$;

X and $X^1$ are each independently selected from the group consisting of oxygen, sulfur, $C(R_2)_2$ and $NR_2$; provided that at least one of X or $X^1$ is carbon;

Y is selected from a group consisting of carbon and nitrogen, provided that when Y is carbon it is substituted with $R^6$;

wherein each $R^6$ is independently selected from a group consisting of hydrogen, halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_1$ to $C_8$ cycloalkyl, $C_3$ to $C_8$ cycloalkyl-$C_1$ to $C_8$ alkyl, $C_1$ to $C_8$ alkylthio, $C_1$ to $C_8$ haloalkyl, —$NR^7R^7$, —O—$CF_3$, —$S(O)$m-$R^7$, and $C(O)$—$NR^7R^7$, $C_1$ to $C_8$ alkyl substituted with a heteroatom wherein the heteroatom is selected from a group consisting of nitrogen, oxygen and sulfur and wherein the heteroatom may be further substituted with a substituent selected from the group consisting of hydrogen, $C_1$ to $C_8$ alkyl, $C_3$ to $C_8$ cycloalkyl, $C_2$ to $C_8$ alkenyl, $C_2$ to $C_8$ alkynyl and $C_1$ to $C_8$ haloalkyl;

wherein each $R^7$ is independently selected from the group consisting of hydrogen and $C_1$-$C_8$ alkyl; p is 1, 2 or 3; n is 0, 1 or 2; and m is 0, 1 or 2.

In another embodiment, the present invention provides for compounds of formula I or pharmaceutical salts thereof;

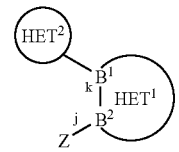

wherein Z is

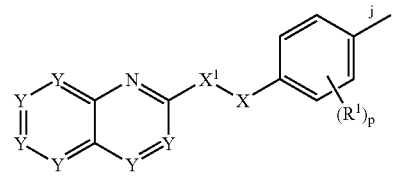

$R^1$ is each independently selected from a group consisting of hydrogen, halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_1$ to $C_8$ haloalkyl, $C_3$ to $C_8$ cycloalkyl, $C_3$ to $C_8$ cycloalkyl-$C_1$ to $C_8$ alkyl, 4 to 7 membered heterocycloalkyl, $C_1$ to $C_8$ alkylthio, —$NR^3R^3$, —O—$CF_3$, —$S(O)_n$—$R^3$, $C(O)$—$NR^3R^3$, and $C_1$ to $C_8$ alkyl substituted with a heteroatom wherein the heteroatom is selected from a group consisting of nitrogen, oxygen and sulfur and wherein the heteroatom may be further substituted with a substituent selected from a group consisting of hydrogen, $C_1$ to $C_8$ alkyl, $C_3$ to $C_8$ cycloalkyl, $C_2$ to $C_8$ alkenyl, $C_2$ to $C_8$ alkynyl, and $C_1$ to $C_8$ haloalkyl;

each $R^3$ is independently selected from a group consisting of hydrogen, $C_1$ to $C_8$ alkyl, $C_2$ to $C_8$ alkenyl, $C_2$ to $C_8$ alkynyl, $C_1$ to $C_8$ haloalkyl, $C_3$ to $C_8$ cycloalkyl;

$R^2$ is selected from the group consisting of hydrogen, $C_1$ to $C_8$ alkyl, $C_3$ to $C_8$ cycloalkyl-$C_1$ to $C_8$ alkyl, $C_2$ to $C_8$ alkenyl, $C_2$ to $C_8$ alkynyl $C_2$ to $C_8$ alkenyl, $C_1$ to $C_8$ haloalkyl and $C_3$ to $C_8$ cycloalkyl;

$HET^1$ is selected from a group consisting of a monocyclic heteroaryl and a bicyclic heteroaryl, wherein the monocyclic and bicyclic heteroaryl may be optionally substituted with at least one $R^4$;

$R^4$ is selected from a group consisting of $C_1$ to $C_8$ haloalkyl;

$HET^2$ is a monocyclic or bicyclic heteroaryl, wherein the monocyclic and bicyclic heteroaryl and may be substituted with at least one $R^5$;

$R^5$ is independently selected from a group consisting of halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_3$ to $C_8$ cycloalkyl, $C_3$ to $C_8$ cycloalkyl-$C_1$ to $C_8$ alkyl, $C_1$ to $C_8$ alkylthio, —$NR^7R^7$, and $C_1$ to $C_8$ haloalkyl;

$B^1$ and $B^2$ are adjacent atoms in $Het^1$ which are independently selected from a group consisting of carbon and nitrogen;

bond j is a covalent bond between Z and $B^2$;

bond k is a bond in $Het^1$ between $B^1$ and $B^2$;

X and $X^1$ are each independently selected from the group consisting of oxygen, sulfur, $C(R_2)_2$ and $NR_2$, provided that at least one of X or $X^1$ is carbon;

Y is selected from a group consisting of carbon and nitrogen, provided that when Y is carbon it is substituted with $R^6$;

wherein each $R_6$ is independently selected from a group consisting of hydrogen, halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_1$ to $C_8$ cycloalkyl, $C_3$ to $C_8$ cycloalkyl-$C_1$ to $C_8$ alkyl, $C_1$ to $C_8$ alkylthio, $C_1$ to $C_8$ haloalkyl, $NR^7R^7$—O—$CF_3$, —S(O)m-$R^7$, and C(O)—$NR^7R^7$. $C_1$ to $C_8$ alkyl substituted with a heteroatom wherein the heteroatom is selected from a group consisting of nitrogen, oxygen and sulfur and wherein the heteroatom may be further substituted with a substituent selected from the group consisting of hydrogen, $C_1$ to $C_8$ alkyl, $C_3$ to $C_8$ cycloalkyl, $C_2$ to $C_8$ alkenyl, $C_2$ to $C_8$ alkynyl, and $C_1$ to $C_8$ haloalkyl;

wherein each $R^7$ is independently selected from the group consisting of hydrogen and $C_1$-$C_8$alkyl; p is 1, 2 or 3; n is 0, 1 or 2 and m is 0, 1 or 2.

In one aspect of the present invention, Y is selected from a group consisting of carbon and nitrogen, provided that not more than one Y is nitrogen.

In another aspect of the present invention, $X^1$ is carbon and X is oxygen.

In another aspect of the present invention all Y's are carbon (i.e., the heteroaryl is quinoline).

The present invention also provides compounds of formula I or pharmaceutical salts thereof, wherein $HET^1$ is a 5 membered heteroaryl group. Preferably, $HET^1$ is selected from a group consisting of pyrazole, isoxazole, triazole, oxazole, thiazole and imidazole.

The present invention also provides subgenera providing for number of ring members for $HET^2$ of formula I wherein $HET^2$ is selected from a group consisting of 4-pyridyl, 4-pyridazine and isoxazole. More preferably, $HET^2$ is 4-pyridyl.

In a preferred embodiment, the invention is directed to a compound of formula I(a)-I(k):

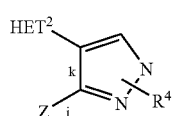

1(a)

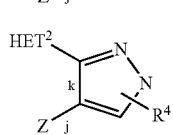

1(b)

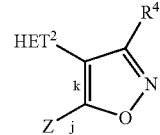

1(c)

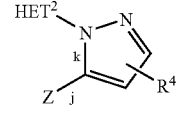

1(d)

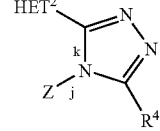

1(e)

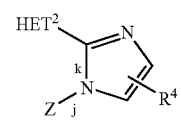

1(f)

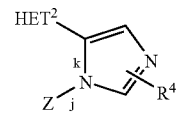

1(g)

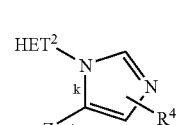

1(h)

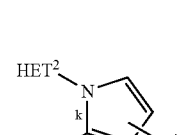

1(i)

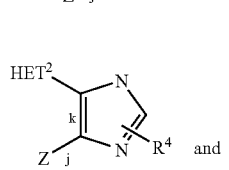

1(j)

and

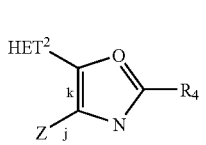

1(k)

wherein j, k, Z $HET^2$ and $R^4$ are as defined above. More preferably, the compounds of formula I have the following general structure:

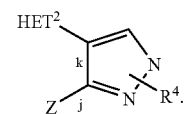

Most preferably, the compounds of formula I have the following general structure:

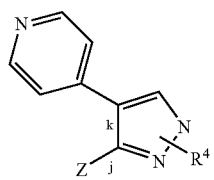

In another aspect, for the above compounds of Formula I, HET¹ is not tetrazole.

Compounds of the Formula I may have optical centers and therefore may occur in different enantiomeric and diastereomeric configurations. The present invention includes all enantiomers, diastereomers, and other stereoisomers of such compounds of the Formula I, as well as racemic compounds and racemic mixtures and other mixtures of stereoisomers thereof.

Pharmaceutically acceptable salts of the compounds of Formula I include the acid addition and base salts thereof.

Suitable acid addition salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable base salts are formed from bases which form non-toxic salts. Examples include, but are not limited to, the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal iron.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO⁻Na⁺, —COO⁻K⁺, or —SO₃⁻Na⁺) or non-ionic (such as —N⁻N⁺(CH₃)₃) polar head group. For more information, see Crystals and the Polarizing Microscope by N. H. Hartshorne and A. Stuart, 4$^{th}$ Edition (Edward Arnold, 1970).

Hereinafter all references to compounds of Formula I include references to salts, solvates, multi-component complexes and liquid crystals thereof and to solvates, multi-component complexes and liquid crystals of salts thereof.

The compounds of the invention include compounds of Formula I as hereinbefore defined, including all polymorphs and crystal habits thereof, prodrugs and isomers thereof (including optical, geometric and tautomeric isomers) as hereinafter defined and isotopically-labeled compounds of Formula I.

As indicated, so-called 'prodrugs' of the compounds of Formula I are also within the scope of the invention. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some examples of prodrugs in accordance with the invention include, but are not limited to, (i) where the compound of Formula I contains a carboxylic acid functionality (—COOH), an ester thereof, for example, a compound wherein the hydrogen of the carboxylic acid functionality of the compound of Formula (I) is replaced by ($C_1$-$C_8$)alkyl;

(ii) where the compound of Formula I contains an alcohol functionality (—OH), an ether thereof, for example, a compound wherein the hydrogen of the alcohol functionality of the compound of Formula I is replaced by ($C_1$-$C_6$)alkanoyloxymethyl; and (iii) where the compound of Formula I contains a primary or secondary amino functionality (—$NH_2$ or —NHR where R≠H), an amide thereof, for example, a compound wherein, as the case may be, one or both hydrogens of the amino functionality of the compound of Formula I is/are replaced by ($C_1$-$C_{10}$)alkanoyl.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug. Some examples of metabolites in accordance with the invention include, but are not limited to, (i) where the compound of Formula I contains a methyl group, an hydroxymethyl derivative thereof (—$CH_3$->—$CH_2OH$):

(ii) where the compound of Formula I contains an alkoxy group, an hydroxy derivative thereof (—OR->—OH);

(iii) where the compound of Formula I contains a tertiary amino group, a secondary amino derivative thereof (—$NR^1R^2$->—$NHR^1$ or —$NHR^2$);

(iv) where the compound of Formula I contains a secondary amino group, a primary derivative thereof (—$NHR^1$->—$NH_2$);

(v) where the compound of Formula I contains a phenyl moiety, a phenol derivative thereof (-Ph->-PhOH); and (vi) where the compound of Formula I contains an amide group, a carboxylic acid derivative thereof (—$CONH_2$->COOH);

(vii) where the compound contains an aromatic nitrogen atom or an tetrtiary aliphatic amine function, an N-oxide derivative thereof.

Compounds of Formual I having a nitrogen atom in a tertiary amine functional group may be further substituted with oxygen (i.e., an N-oxide);

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds that contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula I, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

Specific embodiments of the present invention include the compounds exemplified in the Examples below and their pharmaceutically acceptable salts, complexes, solvates, polymorphs, steroisomers, metabolites, prodrugs, and other derivatives thereof;

This invention also pertains to a pharmaceutical composition for treatment of certain psychotic disorders and conditions such as schizophrenia, delusional disorders and drug induced psychosis; to anxiety disorders such as panic and obsessive-compulsive disorder; and to movement disorders including Parkinson's disease and Huntington's disease, comprising an amount of a compound of formula I effective in inhibiting PDE 10.

In another embodiment, this invention relates to a pharmaceutical composition for treating psychotic disorders and condition such as schizophrenia, delusional disorders and drug induced psychosis; anxiety disorders such as panic and obsessive-compulsive disorder; and movement disorders including Parkinson's disease and Huntington's disease, comprising an amount of a compound of formula I effective in treating said disorder or condition.

Examples of psychotic disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type.

Examples of movement disorders that can be treated according to the present invention include but are not limited to selected from Huntington's disease and dyskinesia associated with dopamine agonist therapy, Parkinson's disease, restless leg syndrome, and essential tremor.

Other disorders that can be treated according to the present invention are obsessive/compulsive disorders, Tourette's syndrome and other tic disorders.

In another embodiment, this invention relates to a method for treating an anxiety disorder or condition in a mammal which method comprises administering to said mammal an amount of a compound of formula I effective in inhibiting PDE 10.

This invention also provides a method for treating an anxiety disorder or condition in a mammal which method comprises administering to said mammal an amount of a compound of formula I effective in treating said disorder or condition.

Examples of anxiety disorders that can be treated according to the present invention include, but are not limited to, panic disorder; agoraphobia; a specific phobia; social phobia; obsessive-compulsive disorder; post-traumatic stress disorder; acute stress disorder; and generalized anxiety disorder.

This invention further provides a method of treating a drug addiction, for example an alcohol, amphetamine, cocaine, or opiate addiction, in a mammal, including a human, which method comprises administering to said mammal an amount of a compound of formula I effective in treating drug addiction.

This invention also provides a method of treating a drug addiction, for example an alcohol, amphetamine, cocaine, or opiate addiction, in a mammal, including a human, which method comprises administering to said mammal an amount of a compound of formula I effective in inhibiting PDE10.

A "drug addiction", as used herein, means an abnormal desire for a drug and is generally characterized by motivational disturbances such a compulsion to take the desired drug and episodes of intense drug craving.

This invention further provides a method of treating a disorder comprising as a symptom a deficiency in attention and/or cognition in a mammal, including a human, which method comprises administering to said mammal an amount of a compound of formula I effective in treating said disorder.

This invention also provides a method of treating a disorder or condition comprising as a symptom a deficiency in attention and/or cognition in a mammal, including a human, which method comprises administering to said mammal an amount of a compound of formula I effective in inhibiting PDE10.

This invention also provides a method of treating a disorder or condition comprising as a symptom a deficiency in attention and/or cognition in a mammal, including a human, which method comprises administering to said mammal an amount of a compound of formula I effective in treating said disorder or condition.

The phrase "deficiency in attention and/or cognition" as used herein in "disorder comprising as a symptom a deficiency in attention and/or cognition" refers to a subnormal functioning in one or more cognitive aspects such as memory, intellect, or learning and logic ability, in a particular individual relative to other individuals within the same general age population. "Deficiency in attention and/or cognition" also refers to a reduction in any particular individual's functioning in one or more cognitive aspects, for example as occurs in age-related cognitive decline.

Examples of disorders that comprise as a symptom a deficiency in attention and/or cognition that can be treated according to the present invention are dementia, for example Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a mood disorder or mood episode in a mammal, including a human, comprising administering to said mammal an amount of a compound of formula I effective in treating said disorder or episode.

This invention also provides a method of treating a mood disorder or mood episode in a mammal, including a human, comprising administering to said mammal an amount of a compound of formula I effective in inhibiting PDE10.

Examples of mood disorders and mood episodes that can be treated according to the present invention include, but are not limited to, major depressive episode of the mild, moderate or severe type, a manic or mixed mood episode, a hypomanic mood episode; a depressive episode with atypical features; a depressive episode with melancholic features; a depressive episode with catatonic features; a mood episode with post-partum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder.

This invention further provides a method of treating a neurodegenerative disorder or condition in a mammal, including a human, which method comprises administering to said mammal an amount of a compound of formula I effective in treating said disorder or condition.

This invention further provides a method of treating a neurodegenerative disorder or condition in a mammal, including a human, which method comprises administering to said mammal an amount of a compound of formula I effective in inhibiting PDE10.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temperal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the present invention, the neurodegenerative disorder or condition comprises neurodegeneration of striatal medium spiny neurons in a mammal, including a human.

In a further embodiment of the present invention, the neurodegenerative disorder or condition is Huntington's disease.

This invention also provides a pharmaceutical composition for treating psychotic disorders, delusional disorders and drug induced psychosis; anxiety disorders, movement disorders, mood disorders, neurodegenerative disorders, obesity, and drug addiction, comprising an amount of a compound of formula I effective in treating said disorder or condition.

This invention also provides a method of treating a disorder selected from psychotic disorders, delusional disorders and drug induced psychosis; anxiety disorders, movement disorders, obesity, mood disorders, and neurodegenerative disorders, which method comprises administering an amount of a compound of formula I effective in treating said disorder.

This invention also provides a method of treating disorders selected from the group consisting of: dementia, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; age-related cognitive decline, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder comprising a delusional disorder or schizophrenia; a bipolar disorder comprising bipolar I disorder, bipolar II disorder, cyclothymic disorder, Parkinson's disease; Huntington's disease; dementia, Alzheimer's disease, multi-infarct dementia, AIDS-related dementia, Fronto temperal Dementia; neurodegeneration associated with cerebral trauma; neurodegeneration associated with stroke; neurodegeneration associated with cerebral infarct; hypoglycemia-induced neurodegeneration; neurodegeneration associated with epileptic seizure; neurodegeneration associated with neurotoxin poisoning; multi-system atrophy, paranoid, disorganized, catatonic, undifferentiated or residual type; schizophreniform disorder; schizoaffective disorder of the delusional type or the depressive type; delusional disorder; substance-induced psychotic disorder, psychosis induced by alcohol, amphetamine, cannabis, cocaine, hallucinogens, obesity, inhalants, opioids, or phencyclidine; personality disorder of the paranoid type; and personality disorder of the schizoid type, which method comprises administering an amounot of a compound of Formula I effecting in said disorders.

This invention also provides a method of treating psychotic disorders, delusional disorders and drug induced psychosis; anxiety disorders, movement disorders, mood disorders, neurodegenerative disorders, obesity, and drug addiction which method comprises administering an amount of a compound of formula I effective in inhibiting PDE10.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The term "alkoxy", as used herein, unless otherwise indicated, as employed herein alone or as part of another group refers to an alkyl, groups linked to an oxygen atom.

The term "alkylthio" as used herein, unless otherwise indicated, employed herein alone or as part of another group includes any of the above alkyl groups linked through a sulfur atom.

The term "halogen" or "halo" as used herein alone or as part of another group refers to chlorine, bromine, fluorine, and iodine.

The term "haloalkyl" as used herein, unless otherwise indicated, refers to at least one halo group, linked to an alkyl group. Examples, of haloalkyl groups include, but are not limited, to trifluoromethyl, trifluoroethyl, difluoromethyl and fluoromethyl groups.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl.

The term "aryl", as used herein, unless otherwise indicated, includes an organic radical derived from an aromatic hydrocarbon by removal of one hydrogen, such as phenyl, naphthyl, indenyl, and fluorenyl. "Aryl" encompasses fused ring groups wherein at least one ring is aromatic.

The terms "heterocyclic", "heterocycloalkyl", and like terms, as used herein, refer to non-aromatic cyclic groups containing one or more heteroatoms, prefereably from one to four heteroatoms, each preferably selected from oxygen, sulfur and nitrogen. The heterocyclic groups of this invention can also include ring systems substituted with one or more oxo moieties. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

The term "heteroaryl", as used herein, refers to aromatic groups containing one or more heteroatoms (preferably oxygen, sulfur and nitrogen), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Heteroaryl groups containing a tertiary nitrogen may also be further substituted with oxygen (i.e., an N-oxide). Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzthiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. For clarity, the term heteroaryl includes the heteroaryl structure in substituent Z in Formula I (i.e., the heteroaryl structure containing Y).

Unless otherwise indicated, the term "one or more" substituents, or "at least one" substituent as used herein, refers to from one to the maximum number of substituents possible based on the number of available bonding sites.

Unless otherwise indicated, all the foregoing groups derived from hydrocarbons may have up to about 1 to about 20 carbon atoms (e.g. $C_1$-$C_{20}$ alkyl, $C_2$-$C_{20}$ alkenyl, $C_3$-$C_{20}$ cycloalkyl, 3-20 membered heterocycloalkyl; $C_6$-$C_{20}$ aryl, 5-20 membered heteroaryl, etc.) or 1 to about 15 carbon atoms (e.g., $C_1$-$C_{15}$ alkyl, $C_2$-$C_{15}$ alkenyl, $C_3$-$C_{15}$ cycloalkyl, 3-15 membered heterocycloalkyl, $C_6$-$C_{15}$ aryl, 5-15 membered heteroaryl, etc.), or 1 to about 12 carbon atoms, or 1 to about 8 carbon atoms, or 1 to about 6 carbon atoms.

"Neurotoxin poisoning" refers to poisoning caused by a neurotoxin. A neurotoxin is any chemical or substance that can cause neural death and thus neurological damage. An example of a neurotoxin is alcohol, which, when abused by a pregnant female, can result in alcohol poisoning and neurological damage known as Fetal Alcohol Syndrome in a newborn. Other examples of neurotoxins include, but are not limited to, kainic acid, domoic acid, and acromelic acid; certain pesticides, such as DDT; certain insecticides, such as organophosphates; volatile organic solvents such as hexacarbons (e.g. toluene); heavy metals (e.g. lead, mercury, arsenic, and phosphorous); aluminum; certain chemicals used as weapons, such as Agent Orange and Nerve Gas; and neurotoxic antineoplastic agents.

As used herein, the term "selective PDE10 inhibitor" refers to a substance, for example an organic molecule, that effectively inhibits an enzyme from the PDE10 family to a greater extent than enzymes from the PDE 1-9 families or PDE11 family. In one embodiment, a selective PDE10 inhibitor is a substance, for example an organic molecule, having a $K_i$ for inhibition of PDE10 that is less than or about one-tenth the $K_i$ that the substance has for inhibition of any other PDE enzyme. In other words, the substance inhibits PDE10 activity to the same degree at a concentration of about one-tenth or less than the concentration required for any other PDE enzyme.

In general, a substance is considered to effectively inhibit PDE10 activity if it has a $K_i$ of less than or about 10 µM, preferably less than or about 0.1 µM.

A "selective PDE10 inhibitor" can be identified, for example, by comparing the ability of a substance to inhibit PDE10 activity to its ability to inhibit PDE enzymes from the other PDE families. For example, a substance may be assayed for its ability to inhibit PDE10 activity, as well as PDE1A, PDE1B, PDE1C, PDE2, PDE3A, PDE3B, PDE4A, PDE4B, PDE4C, PDE4D, PDE5, PDE6, PDE7, PDE8, PDE9, and PDE11.

The term "treating", as in "a method of treating a disorder", refers to reversing, alleviating, or inhibiting the progress of the disorder to which such term applies, or one or more symptoms of the disorder. As used herein, the term also encompasses, depending on the condition of the patient, preventing the disorder, including preventing onset of the disorder or of any symptoms associated therewith, as well as reducing the severity of the disorder or any of its symptoms prior to onset. "Treating" as used herein refers also to preventing a recurrence of a disorder.

For example, "treating schizophrenia, or schizophreniform or schizoaffective disorder" as used herein also encompasses treating one or more symptoms (positive, negative, and other associated features) of said disorders, for example treating, delusions and/or hallucination associated therewith. Other examples of symptoms of schizophrenia and schizophreniform and schizoaffecctive disorders include disorganized speech, affective flattening, alogia, anhedonia, inappropriate affect, dysphoric mood (in the form of, for example, depression, anxiety or anger), and some indications of cognitive dysfunction.

The term "mammal", as used herein, refers to any member of the class "Mammalia", including, but not limited to, humans, dogs, and cats.

The compound of the invention may be administered either alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed thereby can then be readily administered in a variety of dosage forms such as tablets, powders, lozenges, liquid preparations, syrups, injectable solutions and the like. These pharmaceutical compositions can optionally contain additional ingredients such as flavorings, binders, excipients and the like. Thus, the compound of the invention may be formulated for oral, buccal, intranasal, parenteral (e.g. intravenous, intramuscular or subcutaneous), transdermal (e.g. patch) or rectal administration, or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration, the composition may take the form of tablets or lozenges formulated in conventional manner.

The compounds of the invention may be formulated for parenteral administration by injection, including using conventional catheterization techniques or infusion. Formulations for injection may be presented in unit dosage form, e.g. in ampules or in multi-dose containers, with an added preservative. They may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

When a product solution is required, it can be made by dissolving the isolated inclusion complex in water (or other aqueous medium) in an amount sufficient to generate a solution of the required strength for oral or parenteral administration to patients. The compounds may be formulated for fast dispersing dosage forms (fddf), which are designed to release the active ingredient in the oral cavity. These have often been formulated using rapidly soluble gelatin-based matrices. These dosage forms are well known and can be used to deliver a wide range of drugs. Most fast dispersing dosage forms utilize gelatin as a carrier or structure-forming agent. Typically, gelatin is used to give sufficient strength to the dosage form to prevent breakage during removal from packaging, but once placed in the mouth, the gelatin allows immediate dissolution of the dosage form. Alternatively, various starches are used to the same effect.

The compounds of the invention may also be formulated in rectal compositions such as suppositories or retention enemas, e.g. containing conventional suppository bases such as cocoa butter or other glycerides.

For intranasal administration or administration by inhalation, the compound of the invention is conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made e.g. from gelatin) for use in an inhaler or insulator may be formulated containing a powder mix of a compound of the invention and a suitable powder base such as lactose or starch.

Aerosol formulations for treatment of the conditions referred to above (e.g. migraine) in the average adult human are preferably arranged so that each metered dose or "puff" of aerosol contains about 20 mg to about 1000 mg of the compound of the invention. The overall daily dose with an aerosol will be within the range of about 100 mg to about 10 mg. Administration may be several times daily, e.g. 2, 3, 4 or 8 times, giving for example, 1, 2 or 3 doses each time.

A proposed daily dose of the compound of the invention for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

Assay methods are available to screen a substance for inhibition of cyclic nucleotide hydrolysis by the PDE 10 and the PDEs from other gene families. The cyclic nucleotide substrate concentration used in the assay is 1/3 of the $K_m$ concentration, allowing for comparisons of $IC_{50}$ values across the different enzymes. PDE activity is measured using a Scintillation Proximity Assay (SPA)-based method as previously described (Fawcett et al., 2000). The effect of PDE inhibitors is determined by assaying a fixed amount of enzyme (PDEs 1-11) in the presence of varying substance concentrations and low substrate, such that the $IC_{50}$ approximates the $K_i$ (cGMP or cAMP in a 3:1 ratio unlabelled to [$^3$H]-labeled at a concentration of 1/3 Km). ). The final assay volume is made up to 100 μl with assay buffer [50 mM Tris-HCl pH 7.5, 8.3 mM $MgCl_2$, 1 mg/ml bovine serum albumin]. Reactions are initiated with enzyme, incubated for 30-60 min at 30° C. to give <30% substrate turnover and terminated with 50 µl yttrium silicate SPA beads (Amersham) (containing 3 mM of the respective unlabelled cyclic nucleotide for PDEs 9 and 11). Plates are re-sealed and shaken for 20 min, after which the beads were allowed to settle for 30 minutes in the dark and then counted on a TopCount plate reader (Packard, Meriden, Conn.). Radioactivity units can be converted to percent activity of an uninhibited control (100%), plotted against inhibitor concentration and inhibitor $IC_{50}$ values can be obtained using the "Fit Curve" Microsoft Excel extension.

Using such assay, compounds of the present invention were determined to have an $IC_{50}$ for inhibiting PDE10 activity of less than about 10 micromolar.

This invention also pertains to the preparation of compounds of formula I. The present invention also provides for methods for the synthesis compounds of formula I. For example, the present invention provides for a process for forming the compound of formula I, comprising a step of reacting a compound of formula II

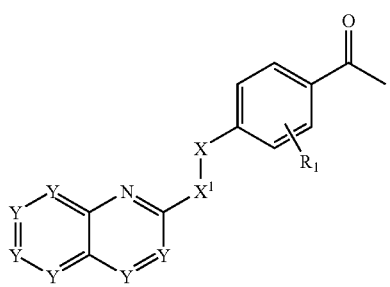

with dimethoxymethyl-dimethyl amine and hydrazine or substituted hydrazine (e.g., such as $R_{20}$—$NHNH_2$ where $R_{20}$ is alkyl).

The present invention also provides for a process for forming the compound of formula I, comprising a step of reacting a compound of formula III

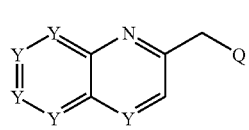

with dimethyl oxalate and a hydrazine of formula $HET^2$-$NHNH_2$.

The present invention also provides for a process for forming the compound of formula I, comprising a step of reacting a compound of formula IV

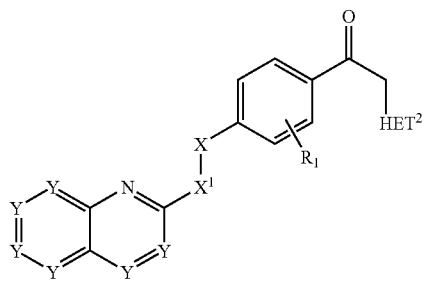

with dimethoxymethyl-dimethyl amine and hydrazine or substituted hydrazine.

The present invention also provides for a process for forming the compound of formula I, comprising a step of reacting a compound of formula V

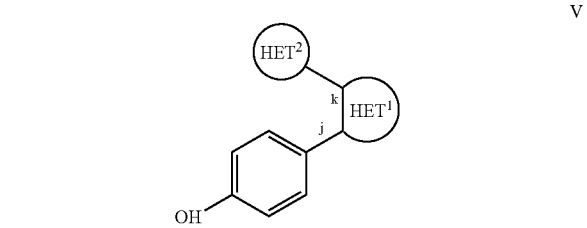

with a compound of formula VI

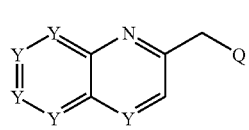

wherein Q is a hydroxyl or a halide.

DETAILED DESCRIPTION OF THE INVENTION

Scheme 1 depicts the preparation of the pyrazole class of compounds of this invention. Alkylation of a substituted phenol with 2-methyl chloro quinoline provides the desired ether. Hydrolysis of the ester and treatment with thionyl chloride provides the desired acid chloride. Addition of O,N-dimethyl hydroxyl amine hydrochloride provides the Weinreb amide for coupling (Weinreb et al, *Tet Lett.*, 1981, 22(39) 3815). Anion generation with 4-picoline and LDA followed by addition of the Weinreb amide affords the ketone. The ketone can then be treated with dimethoxymethyl-dimethyl amine at reflux to form the enaminone intermediate. Treatment with various hydrazines affords the pyrazole analogues. A variety of ratios of the two isomers were obtained. These isomers were separated via, crystallization, Biotage MPLC, preparative TLC or preparative HPLC. This reaction scheme is general for a variety of starting substituted phenols, substituted quinolines and substituted hydrazines.

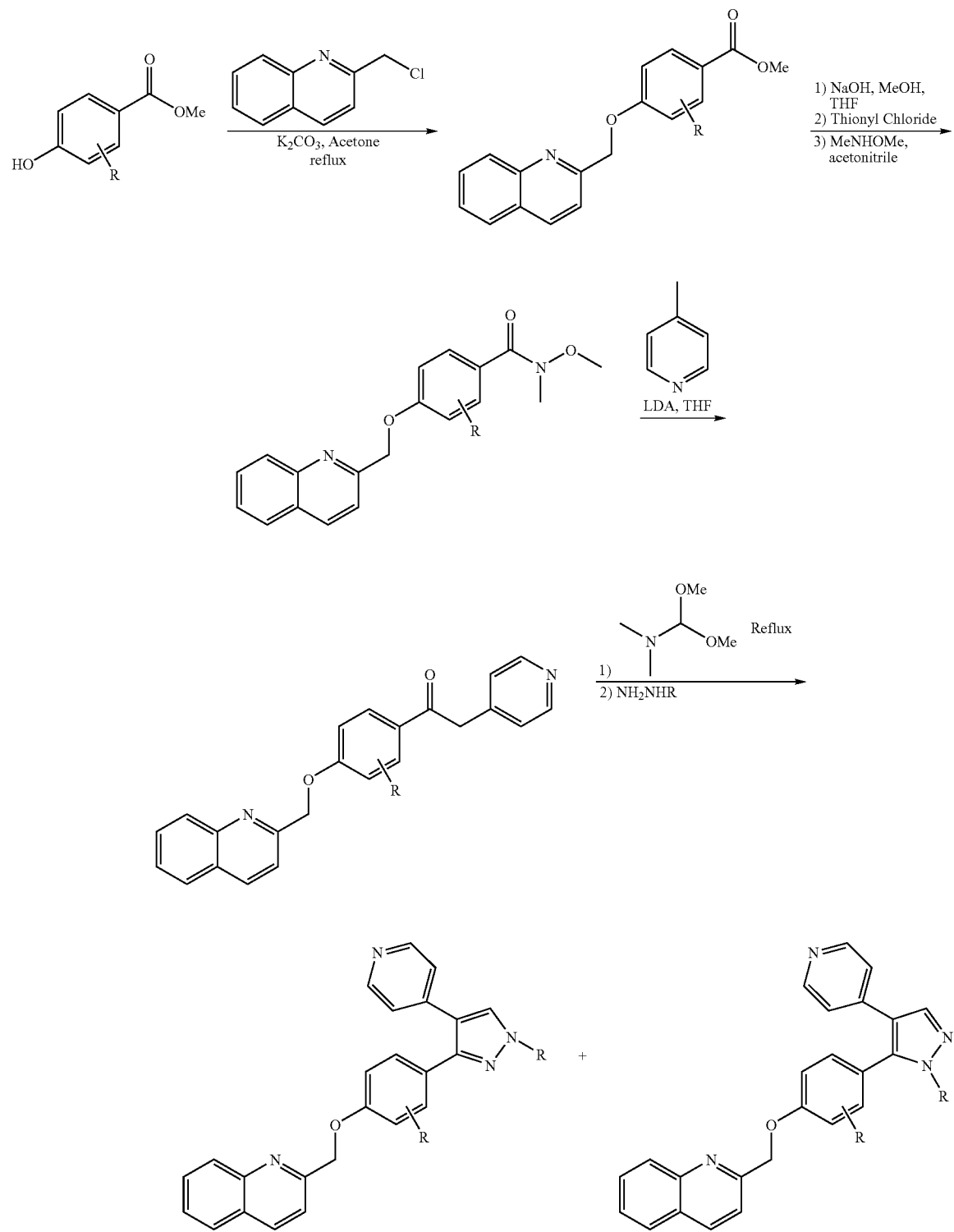

Alternatively, the substituted pyrazole compounds can be prepared by alkylation of the NH pyrazole. One set of conditions is the utilization of cesium carbonate as the base with an alkyl halide as the electrophile in a solvent such as dimethyl formamide. Some reactions require heating.

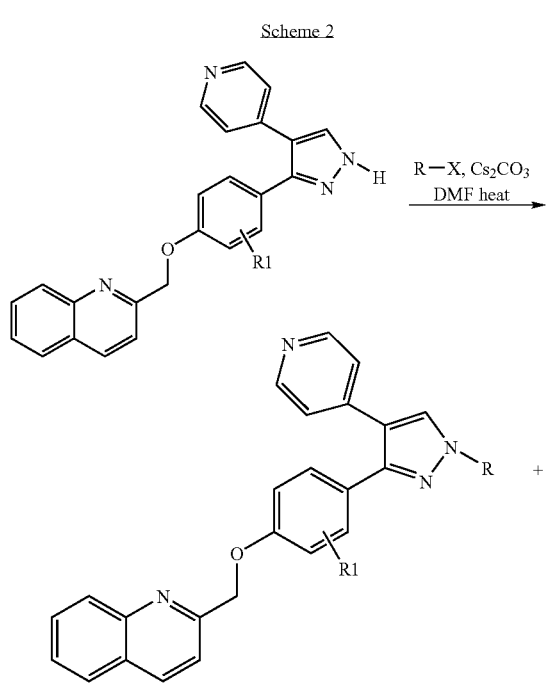

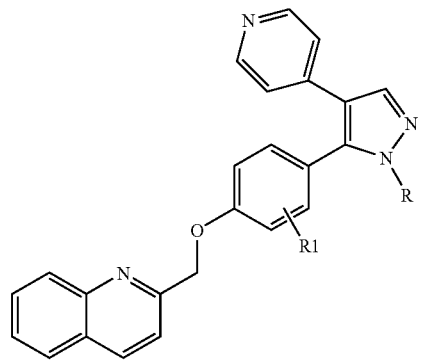

As depicted in Scheme 3, a variety of heterocycles can be prepared from the enaminone intermediate. Pyrimidines can be prepared by heating with substituted formamides in the presence of ethanol and sodium ethoxide. Isoxazoles are prepared by heating the enaminone with hydroxyl amine in methanol/acetic acid. Only one isomer in the isoxazole case is formed. By heating with amino pyroles, amino imidazoles or amino triazoles, 6-5 bicyclic systems can be formed.

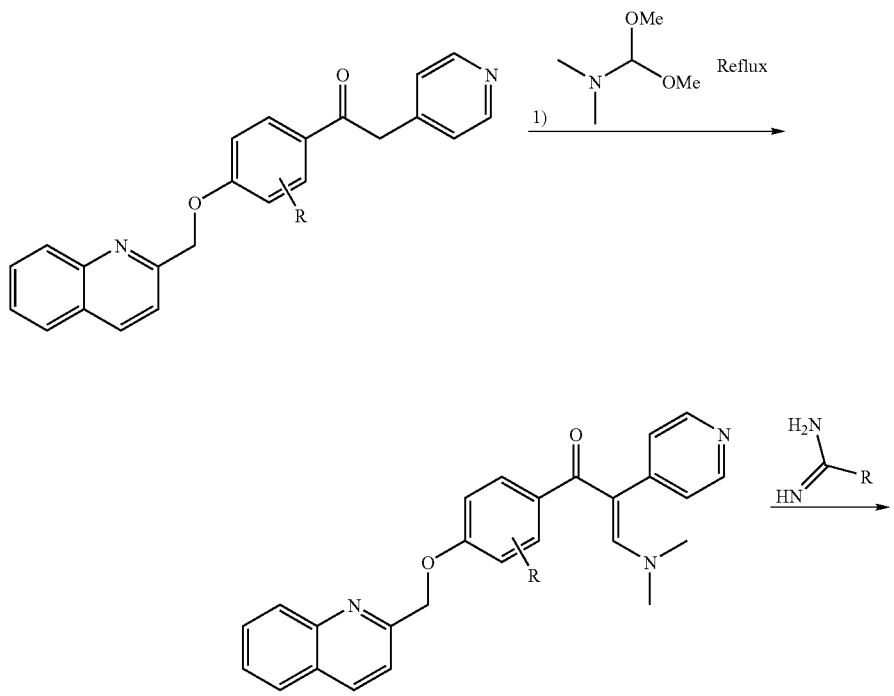

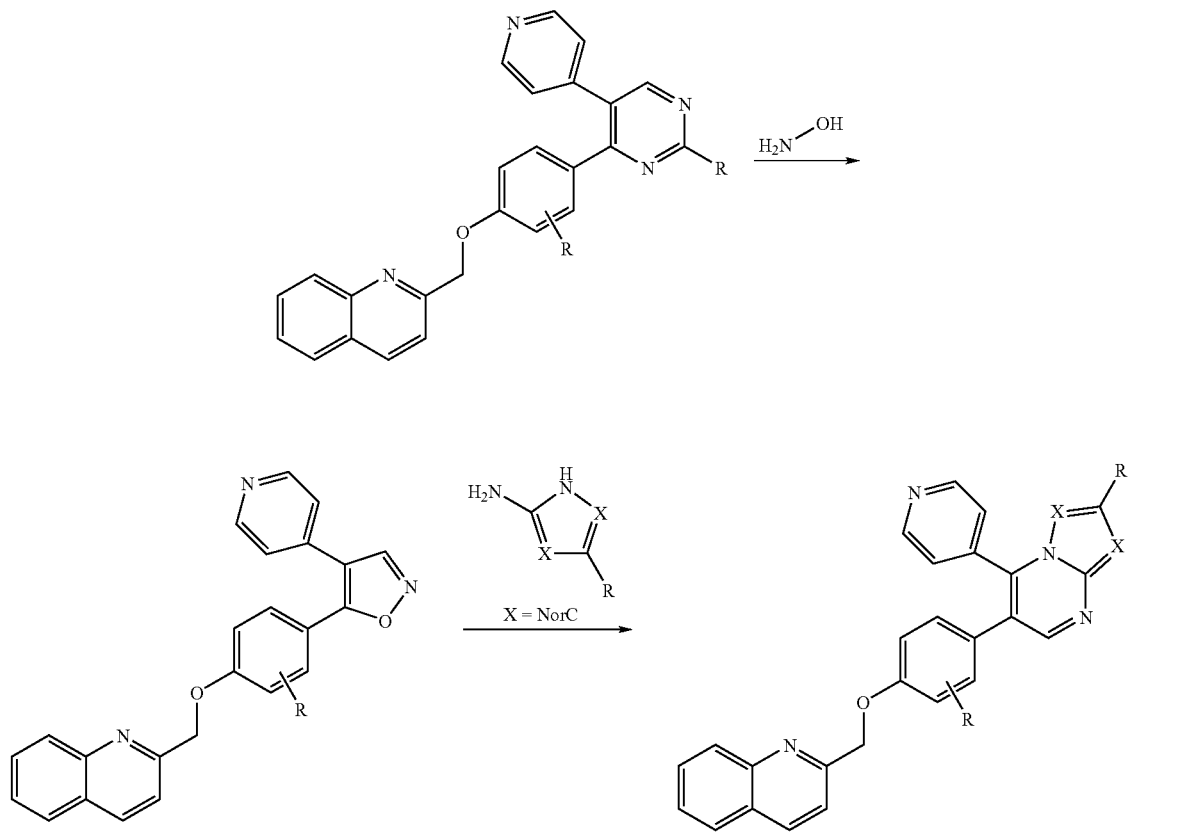

A variety of 4-pyridyl heterocyclic replacements can be prepared according to scheme 4. Methyl heterocycles such as 3,5-dimethyl isoxazole and methyl pyridazine can be deprotated with lithium diisopropyl amide and added to a Weinreb amide (Weinreb et al, *Tet Lett.*, 1981, 22(39) 3815) to provide the desired ketone. Sequential treatment with dimethoxymethyl-dimethyl amine and a hydrazine provides the heterocyclic pyrazoles. Pyrimidines and isoxazoles can also be prepared as described in Scheme 3.

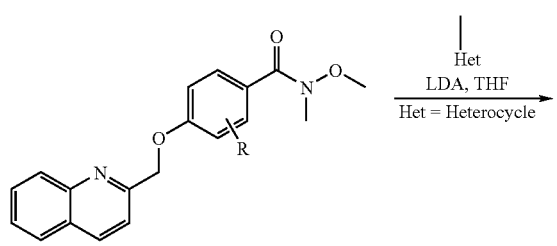

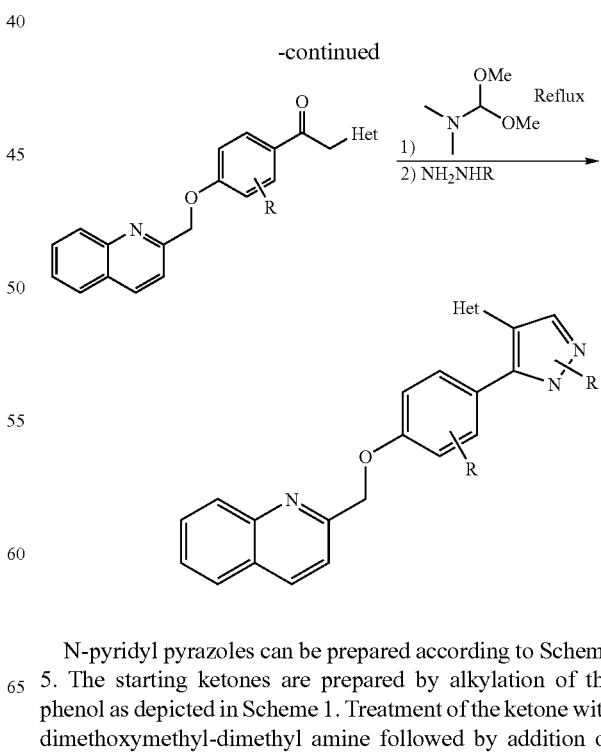

N-pyridyl pyrazoles can be prepared according to Scheme 5. The starting ketones are prepared by alkylation of the phenol as depicted in Scheme 1. Treatment of the ketone with dimethoxymethyl-dimethyl amine followed by addition of 4-pyridyl hydrazine (see *J. Med. Chem.* 2002, 45(24) 5397) provides the desired compounds. Other heterocyclic replacements for 4-pyridyl can be prepared by using the requisite hydrazine.

Scheme 5

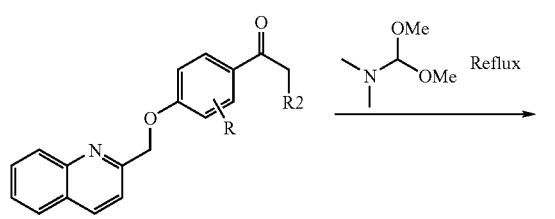

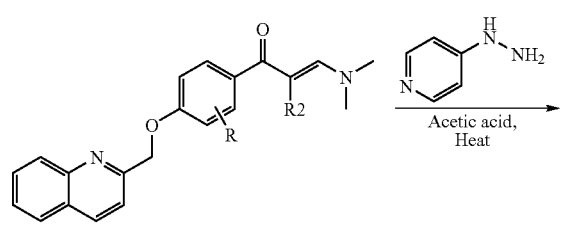

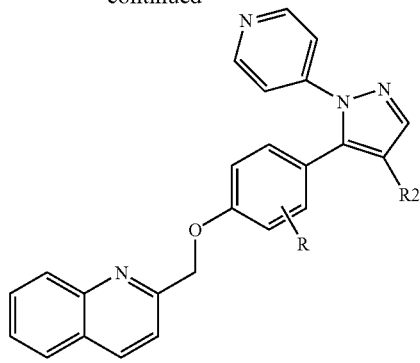

As depicted in Scheme 6, 3-substituted-N-pyridyl pyrazoles can be prepared by literature methods. (see *J. Med. Chem.* 2004, 47, 2180). Treatment of the acetophenone (prepared according to scheme 1) with sodium methoxide and dimethyl oxalate provides the ester intermediate. Addition of 4-pyridyl hydrazine (see *J. Med. Chem.* 2002, 45(24) 5397) provides the pyrazole with an ester at the 3-position. This ester can be converted to amides by hydrolysis and coupling with amines. It can be converted to ethers by reduction to the alcohol and alkylation. Amine formation is capable by amide formation followed by reduction or conversion to the aldehyde followed by reductive amination. All of these transformations can be carried out by those skilled in the art of organic chemistry.

Scheme 6

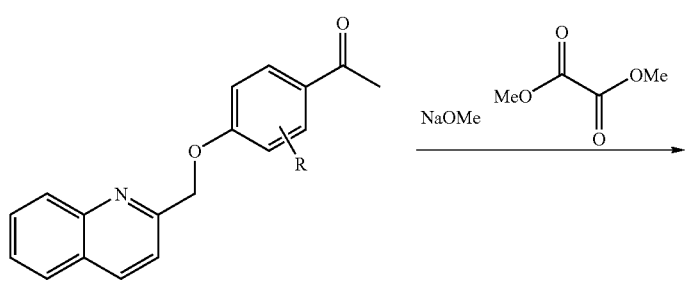

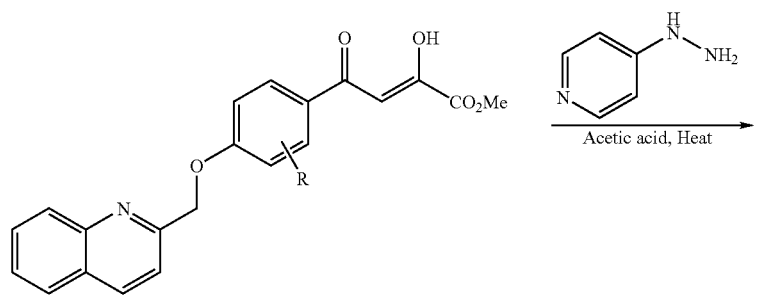

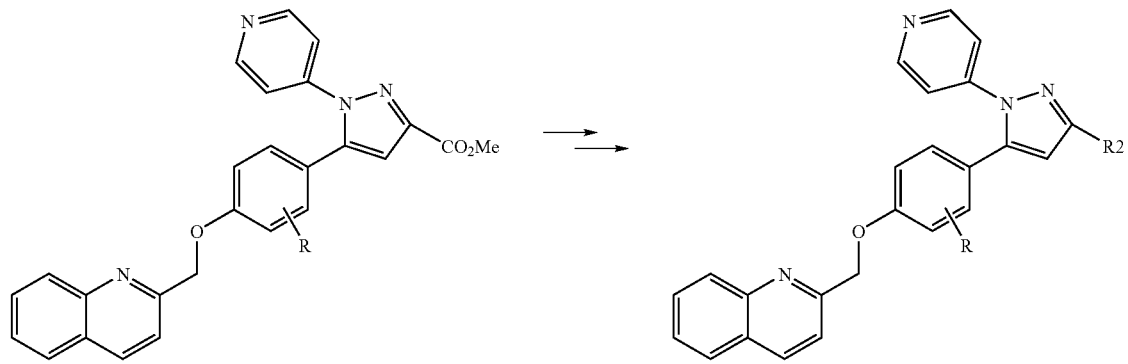

The benzyl intermediates can be prepared by the method shown in scheme 1. The benzyl ether can be removed via treatment with hydrogen gas over a palladium catalyst such as palladium on carbon or palladium hydroxide in a variety of solvents. The phenol can then be alkylated using a benzylic chloride in acetone heating with potassium carbonate. Also Mitsunobu chemistry (Hughes, D. L., *The Mitsunobu Reaction.* Organic Reactions. Vol. 42. 1992, New York. 335-656.) can be applied to couple the phenol with alcohols.

Scheme 7

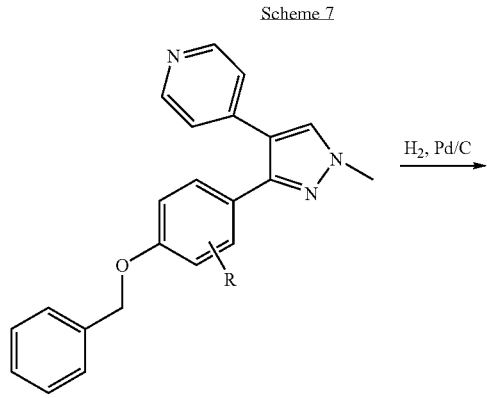

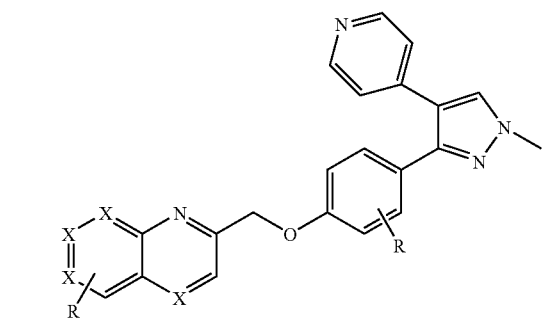

X = C or N

Many benzylic halides or alcohols are commericially available or are known in the literature. General ways to make these intermediates by those skilled in the art are reduction of an ester, acid or aldehyde to form an alcohol. One general procedure is the oxidation of a benzylic site with selenium dioxide to provide an aldehyde that is subsequentially reduced with sodium borohydride. Benzylic halide can be formed vial halogenation (see Syn. Comm. 1995, 25(21) 3427-3434).

Scheme 8

1) SeO$_2$, 140° C. Dioxane
2) NaBH$_4$, EtOH

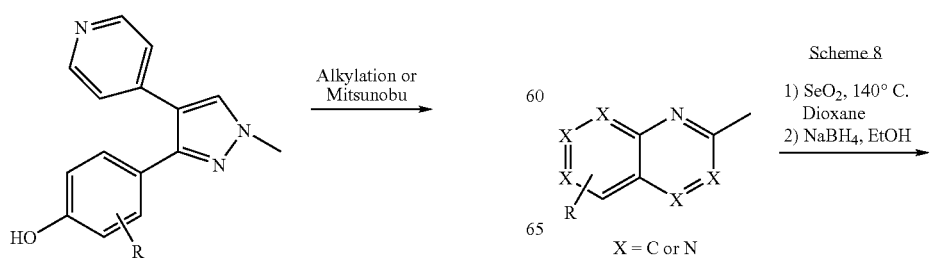

X = C or N

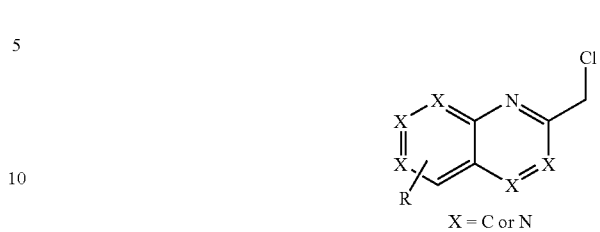

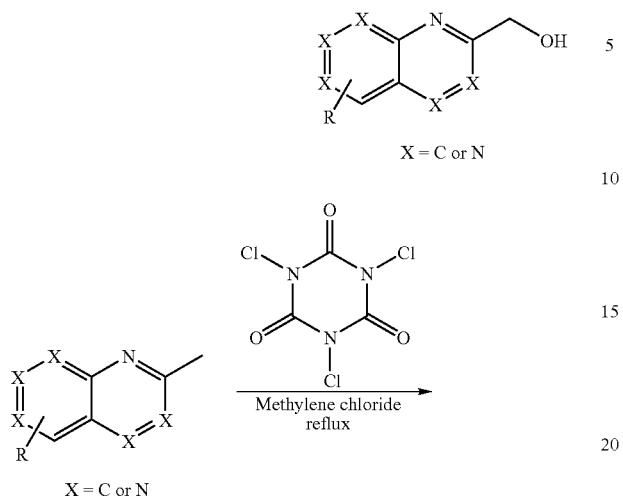

Triazole analogues can be prepared in many ways. One way is depicted in Scheme 9. Treatment of a hydrazide with dimethyl formamide dimethyl acetal to form an intermediate, which is subsequently treated with an amine or aniline with the addition of heat and acetic acid provides the 1,2,4 triazoles (see *Org. Lett*, 2004, 6(17), 2969-2971). The regioisomeric triazoles can be prepared by interchanging the functionality of the starting materials.

Scheme 9

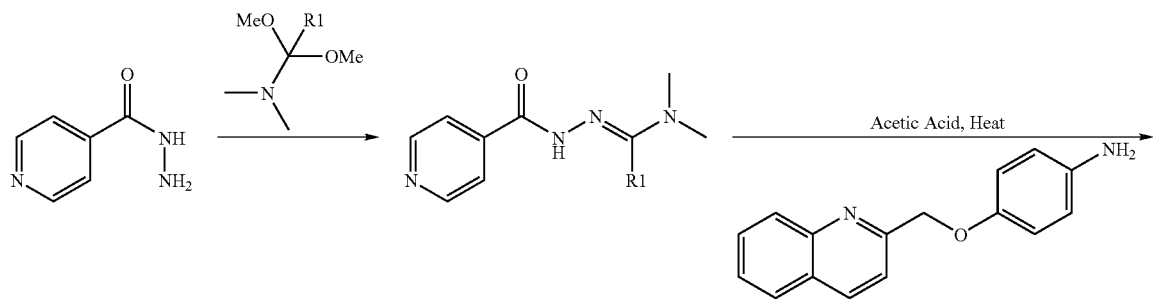

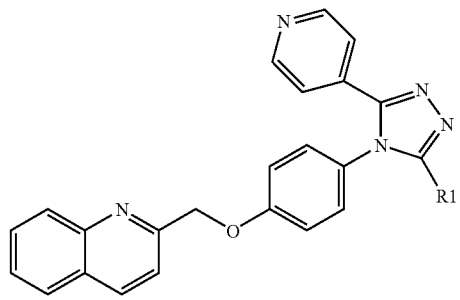

Other triazole isomers can be prepared according to scheme 10 by starting with the carboxyamides and treating with dimethyl formamide dimethyl acetal followed by the addition of aromatic hydrazines. The regioisomeric triazoles can be prepared by interchanging the functionality of the starting materials.

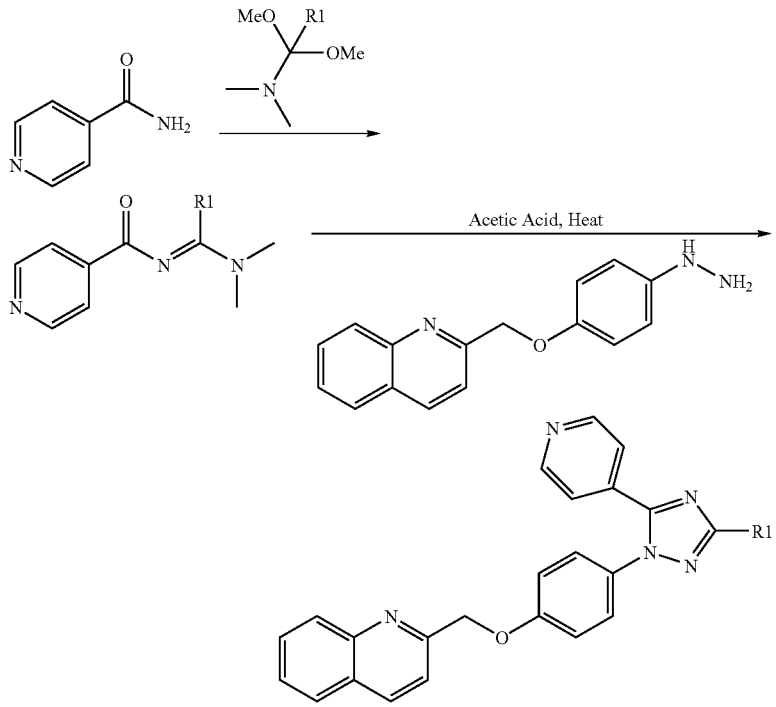

The inverted ketone isomer can be prepared according to Scheme 11. (Bunting et al. *JACS*, 1988, 110, 4008.) The starting aldehyde is coupled with a phosphonate to provide the enaminone. The enaminone is hydrolyzed to provide the desired ketone. The ketone can then be utilized according to Scheme 1,2 and 3 to provide the desired compounds

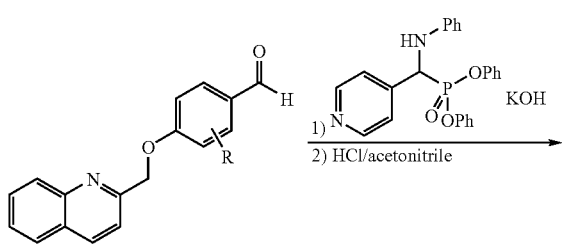

-continued

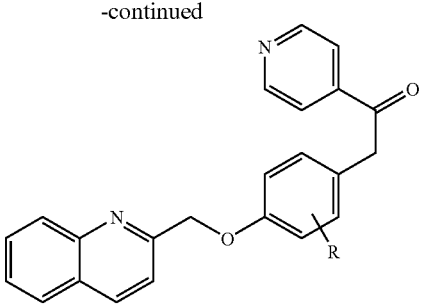

Scheme 12 depicts a method for synthesizing a 4,5-diaryl oxazole. In the illustrated case, 4-benzyloxy-benzaldehyde and 4-methylbenzenesulfinic acid are heated with formamide to generate a substituted formamide as shown. This transformation is known in the literature. [J. Med Chem., 2002, 45, 1697] Dehydration of the formamide in a reaction mediated by POCl3 gives a tosylmethyl isocyanate. This class of compound can be treated with an aldehyde and a base to yield an oxazole. In the illustrated case, the tosylmethylisocyanate is treated with isonicotinaldehyde and potassium carbonate. The product of this reaction is an oxazole possessing a 4-benzyloxyphenyl group at the 4-position of the oxazole ring, and a 4-pyridyl substituent at the 5-position. These substituents can be substituted with other aryl groups simply by utilizing different aryl-aldehydes for steps one and three of the sequence. Cleavage of the benzyloxy group is achieved by the standard method of catalytic hydrogenation, and the resultant phenol is easily alkylated by treatment with an alkyl halide, such as 2-(chloromethyl)quinoline, and cesium fluoride in DMF. The method is not limited to the illustrated case as the relative positions of the phenyl and pyridyl rings can be switched, and said rings may comprise a variety of aryl groups displaying various substitution patterns.

-continued

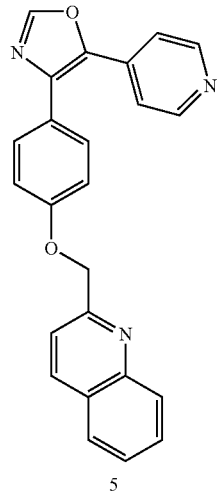

5

Scheme 13 depicts a method for preparing 4,5-substituted oxazoles possessing alkyl group substitution in the 2-position of the oxazole ring. In the illustrated case, 1-(4-Benzyloxyphenyl)-2-pyridin-4-yl-ethanone is brominated by treatment with bromine in acetic acid according to traditional methods. The resultant α-bromoketone is then treated with ammonium acetate and sodium acetate in acetic acid, which yields the methyl-substituted oxazole ring as disclosed in the patent literature (WO 9513067). The methyl group can be replaced by other alkyl groups. For example, substitution of ammonium ethanoate, sodium ethanoate, and ethanoic acid acid would yield ethyl group substitution. Cleavage of the benzyloxy group is achieved by the standard method of catalytic hydrogenation, and the resultant phenol is easily alkylated by treatment with an alkyl halide as described above. The method is not limited to the illustrated case as the relative positions of the phenyl and pyridyl rings can be switched, and said rings may comprise a variety of aryl groups displaying various substitution patterns.

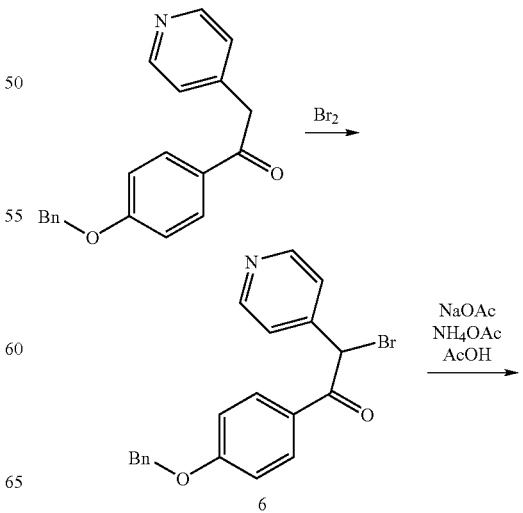

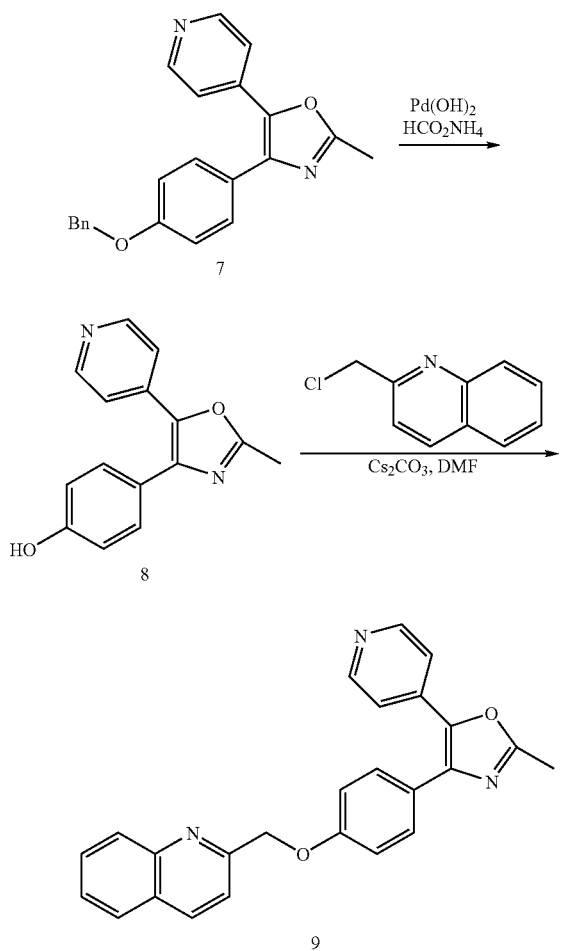

Step 1 of Scheme 14 is an imine formation/heterocycle formation. A compound of formula 2A wherein R1 is alkyl, benzyl, or allyl, is condensed with 4-pyridine carboxaldehyde in solvent such as toluene and is heated to reflux with a Dean-Stark apparatus attached to remove water for about 40 hours. After removal of toluene, the crude imine is mixed with tosylmethylisocyanide and a base such as potassium carbonate, in a solvent mixture of 1,2-dimethoxyethane and methanol, and is heated at reflux for about 3 hours to afford 3A.

Step 2 of Scheme 14 is a phenol dealkylation. If R1 is methyl, the dealkylation can be effected with boron tribromide (BBr3) in a non-coordinating solvent such as methylene chloride at about 20-40° C. for about 3-48 hours, where about 24 hours is preferred to yield 4A. If R2 is benzyl, the dealkylation can be effected with in neat trifluoracetic acid with anisole at a temperature of about 75° C. for about 3-48 hours, where about 24 hours is preferred to yield 4A. If R1 is allyl, the dealkylation can be effected with a palladium catalyst, such as dichloropalladium bis(triphenylphosphine) of palladium acetate, where dichloropalladium bis(triphenylphosphine) is preferred, with a reducing agent such as n-butylammonium formate, in a solvent such as tetrahydrofuran, 1,2-dichloroethane, methylene chloride, or an alkanol, where 1,2-dichloroethane is preferred, in a temperature range from about 20° C. to 75° C., to yield 4A.

Step 3 of Scheme 14 is a phenol alkylation. Treatment of 4A with a base such as potassium carbonate, sodium carbonate, cesium carbonate, sodium hydride, or potassium hydride, where cesium carbonate or sodium hydride are preferred, in a solvent such as tetrahydrofuran, 1,2-dimethoxyethane, N,N-dimethylformamide, dimethylacetamide, N-methylpyrrolidinone, or dimethylsulfoxide, where dimethylsulfoxide or N,N-dimethylformamide are preferred, at a temperature from about 20° C. to 70° C., where about 23° C. is preferred, for about 3-48 hours, where about 24 hours is preferred, affords 1A.

Step 4 of Scheme 14 is an imidazole deprotonation/electrophilic trapping. Treatment of 3A with a base such as lithium diisopropyl amide or lithium 2,2,6,6-tetramethylpiperidine, where lithium diisopropylamide is preferred, in a solvent such as tetrahydrofuran, at a temperature from about −78° C. to 0° C., where about −20° C. is preferred, for about 5 minutes to 30 minutes, where about 10 minutes is preferred, followed by addition of the desired electrophile R3-1, affords 3B.

Step 5 of Scheme 14 is a phenol dealkylation and uses the same methods as described for Step 2 above to produce 4B.

Step 6 of Scheme 14 is a phenol alkylation and uses the same methods as described for Step 3 above to produce 1B.

Scheme 14

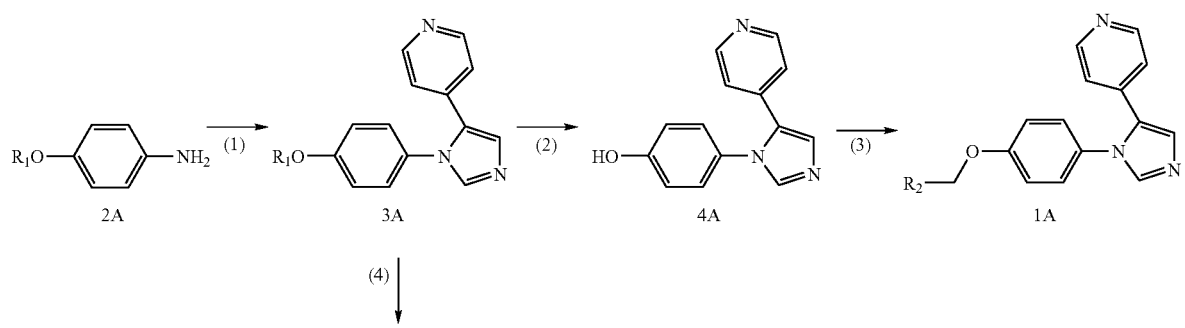

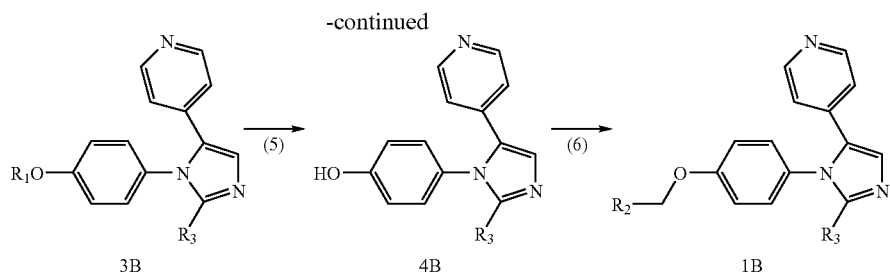

Step 1 of Scheme 15 is an acylation of an amine to form an amide. Compound 2A, wherein R1 can be methyl, benzyl, or allyl, is treated with an acid chloride or a carboxylic acid in the presence of a coupling reagent, such as tri-n-propylphosphonic anhydride or dicyclohexyl carbodiimide, where tri-n-propylphosphonic anhydride is preferred, in the presence of a base such as sodium hydroxide, potassium or sodium carbonate, triethylamine, or diisopropylethylamine, where diisopropylethylamine is preferred, in a solvent system such as water/methylene chloride, water/ethyl acetate, ethyl acetate, tetrahydrofuran, or methylene chloride, where ethyl acetate is preferred, at a temperature from about 0° C. to 50° C., where about 20° C. to 30° C. is preferred, to yield 5A.

Step 2 consists of a chlorination to form an iminochloride, reaction with an amine to form an amidine, followed by treatment with acid to form an imidazole. Compound 5A is treated with a chlorinating agent such as $PCl_5/POCl_3$ at a temperature of about 120° C. for about 4 hours. The chlorinating agent is removed in vacuo and an excess of 1,1-diethoxy-2-ethylamine in a solvent such as isopropanol is added and the mixture is stirred for about 5-24 hours at about 23° C. The solvent is removed in vacuo and concentrated hydrochloric acid and isopropanol is added and the mixture is heated to about 90° C. for about 24 hours to yield 6A.

Step 3 of Scheme 15 is a phenol dealkylation. If R1 is methyl, the dealkylation can be effected with boron tribromide (BBr3) in a non-coordinating solvent such as methylene chloride at about 20-40° C. for about 3-48 hours, where about 24 hours is preferred to yield 7A. If R2 is benzyl, the dealkylation can be effected with in neat trifluoracetic acid with anisole at a temperature of about 75° C. for about 3-48 hours, where about 24 hours is preferred to yield 7A. If R1 is allyl, the dealkylation can be effected with a palladium catalyst, such as dichloropalladium bis(triphenylphosphine) of palladium acetate, where dichloropalladium bis(triphenylphosphine) is preferred, with a reducing agent such as n-butylammonium formate, in a solvent such as tetrahydrofuran, 1,2-dichloroethane, methylene chloride, or an alkanol, where 1,2-dichloroethane is preferred, in a temperature range from about 20° C. to 75° C., to yield 7A.

Step 4 of Scheme 15 is a phenol alkylation. Treatment of 7A with a base such as potassium carbonate, sodium carbonate, cesium carbonate, sodium hydride, or potassium hydride, where cesium carbonate is preferred, in a solvent such as tetrahydrofuran, 1,2-dimethoxyethane, N,N-dimethylformamide, dimethylacetamide, N-methylpyrrolidinone, or dimethylsulfoxide, where dimethylsulfoxide is preferred, at a temperature from about 20° C. to 70° C., where about 23° C. is preferred, for about 3-48 hours, where about 24 hours is preferred, affords 1C.

Scheme 15

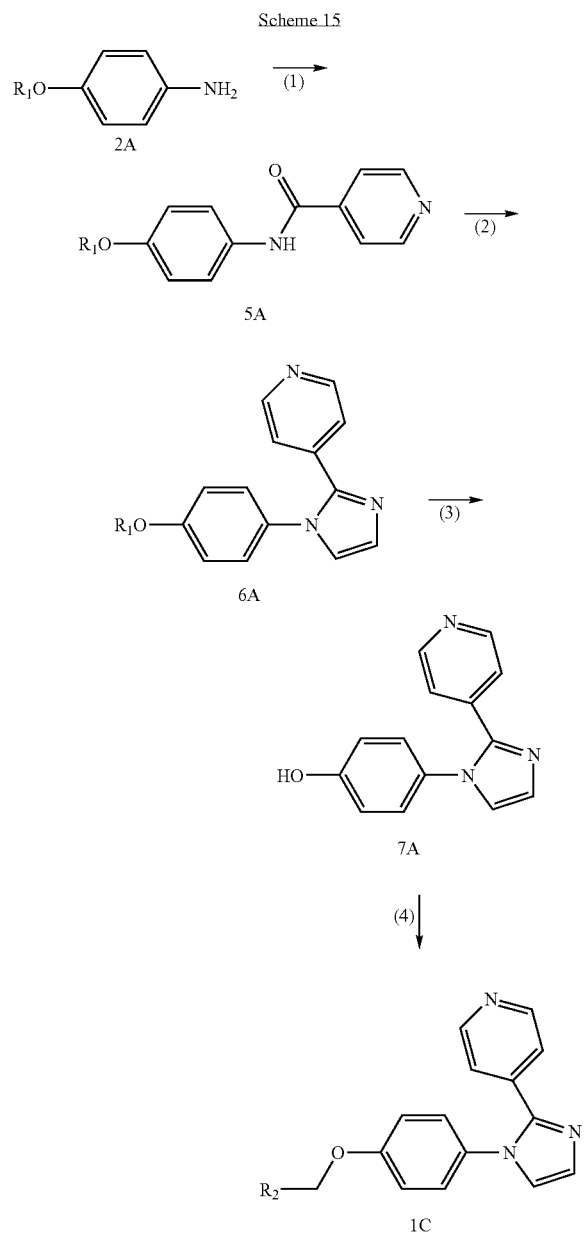

The quinolyl benzaldehyde can be coupled with the ketone in the presence of refluxing piperidine to provide the desired olefin. Treatment with hydrazine affords the NH-pyrazole.

This can be further elaborated by treatment with sodium hydride and an electrophile such as methyl iodide to provide substituted pyrazoles.

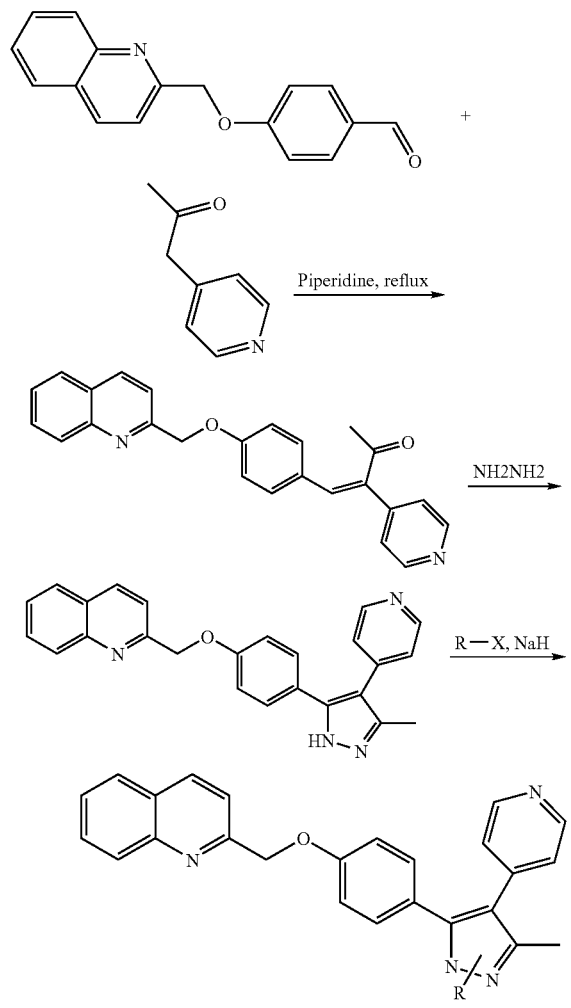

As depicted in scheme 17, the alkyne and iodide can be coupled via a Sonagashira coupling and the methyl ether deprotected with boron tribromide in dichloromethane. Alkylation of the phenol with 2-chloromethylquinoline according to the methods described above provides the penultimate intermediate. Treatment with trimethyl silyl azide in a sealed tube at 70-190° C., preferably about 150° C., for 24-72 h, provides the desired triazole.

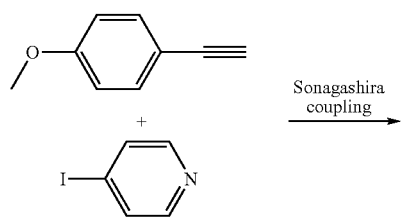

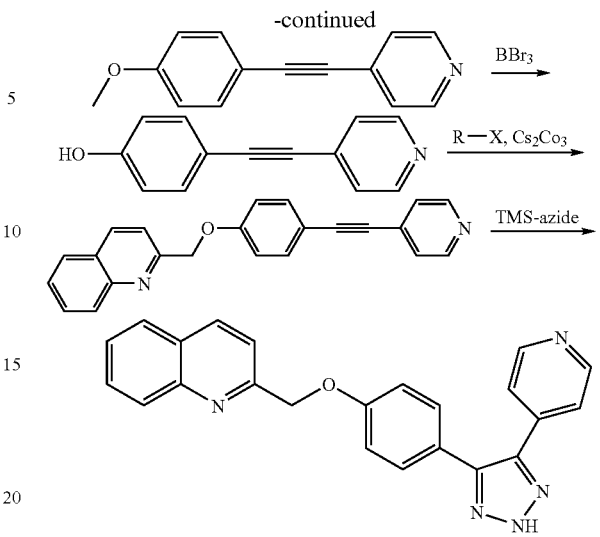

General Experimental

Organic solutions were dried with magnesium or sodium sulfate if not otherwise specified. Room temperature is abbreviated as RT. HPLC-MS system 1 consisted of Zorbax Bonus-RP™ 4.6×150 mm column, 1.0 mL/min, solvent A=MeCN, solvent B=0.1% aqueous formic acid, linear gradient of 1:9 A:B to 95:5 A:B over 10 min, using a Hewlett-Packard 1100 HPLC system equipped with diode array and mass detectors. HPLC system 2 used a linear gradient of 3:7 A:B to 95:5 A:B over 15 min. When purification by RP-HPLC is indicated, a Shimadzu preparative HPLC instrument equipped with X-Terra™ 50×50 mm column, solvent A=acetonitrile, solvent B=water, each containing either 0.1% trifluoroacetic acid ("acidic conditions") or 0.1% concentrated ammonium hydroxide ("basic conditions"), linear gradient of 25%-85% A:B over 10 min.

The following Examples illustrate the present invention. It is to be understood, however, that the invention, as fully described herein and as recited in the claims, is not intended to be limited by the details of the following Examples.

Experimental Procedures

Preparation 1

4-(Quinolin-2-ylmethoxy)-benzoic acid methyl ester

To a solution of 2-Chloromethyl quinoline. (2 g, 9.3 mmole) in acetone (47 ml, 0.2M) was added 4-hydroxy benzoic acid methyl ester (1.42 g, 1.0 eq.) and potassium carbonate (3.86 g, 3 eq.). The reaction mixture was heated at 60° C. for 16 h under $N_2$ atmosphere, cooled to ambient temperature and poured into 1N sodium hydroxide (50 ml)/ethyl acetate (100 ml). The layers were separated and the organic layer dried magnesium sulfate, filtered and concentrated. Biotage MPLC was run using a 5-30% ethyl acetate/hexane gradient on a 40 M column to provide the title compound as a white solid (1.66 g, 61%). $^1$H NMR (400 MHz, CDCl$_3$) δ 8.18 (d, J=8.7 Hz, 1 H), 8.07 (d, J=8.3 Hz, 1 H), 7.95 (M, 2H), 7.82 (d, J=7.9 Hz, 1 H), 7.74 (dt, J=7.1, 1.7 Hz, 1 H), 7.62 (d, J=8.3 Hz, 1 H), 7.55 (dt, J=7.9, 1.2 Hz, 1 H), 7.03 (d, J=9.1, 2 H), 5.41 (s, 2 H), 3.84 (s, 3 H); MS: (M$^+$H m/z=294.2).

Preparation 2

4-(Quinolin-2-ylmethoxy)-benzoic acid

To a solution of 4-(Quinolin-2-ylmethoxy)-benzoic acid methyl ester (500 mg, 1.7 mmole) in tetrahydrofuran (8.5 ml) and methanol (3 ml) was added 1N NaOH (3.4 ml, 2 eq.). The reaction mixture was stirred at ambient temperature for 16 h. To the reaction mixture was added 50 ml of brine and the pH was adjusted to 3 with 1N HCl to provide a white precipitate which was filtered and dried to provide the title compound as a white solid (463 mg, 98%). $^1$H NMR (400 MHz, DMSO) δ 8.39 (d, J=8.3 Hz, 1 H), 7.99 (m, 2 H), 7.81 (M, 2H), 7.76 (dt, J=8.3, 1.7 Hz, 1 H), 7.64 (d, J=8.3 Hz, 1 H), 7.60 (dt, J=7.9, 1.3 Hz, 1 H), 7.12 (M, 2 H), 5.41 (s, 2 H); MS: (M$^+$H m/z=280.2).

Preparation 3

N-Methoxy-N-methyl4-(quinolin-2-ylmethoxy)-benzamide

To a solution of 4-(Quinolin-2-ylmethoxy)-benzoic acid (25.98 g, 93 mmole) was added 250 ml of thionyl chloride under N$_2$. The reaction mixture stirred 3 h and the excess thionyl chloride was removed under vacuum. The acid chloride was dissolved in tetrahydrofuran (450 ml) and triethylamine (50 ml, 4 eq.) was slowly added. O,N-dimethyl hydroxyl amine hydrochloride (27 g, 3 eq.) was added and the reaction stirred 18 h. The reaction mixture was placed on a rotovap to remove the solvent, partitioned between 1N NaOH and methylene chloride, separated, dried magnesium sulfate, filtered and concentrated. The crude product was filtered through silica gel eluting with 30-70% ethyl acetate/hexane to proved the title compound as a brown oil (26.26 g, 87%); $^1$H NMR (400 MHz, CDCl$_3$) δ 8.17 (d, J=8.7 Hz, 1 H), 8.06 (d, J=8.3 Hz, 1 H), 7.81 (d, J=8.3 Hz, 1H), 7.67 (m, 3 H), 7.63 (d, J=8.3 Hz, 1 H), 7.52 (m, 1 H), 7.01 (M, 2 H), 5.39 (s, 2 H), 3.52 (s, 3 H) 3.31 (s, 2H); MS: (M$^+$H m/z=323.2).

Preparation 4

2-pyridin-4-yl-1-[4-(quinolin-2-ylmethoxy)-phenyl]-ethanone

To a solution of Lithium diisopropyl amide (1.0M) in tetrahydrofuran was added 4-picoline dropwise (7.55 ml, 5 eq.) at 0° C. under N$_2$. After 30 min the anion was cooled to −78° C. In a separate round bottom flask N-Methoxy-N-methyl-4-(quinolin-2-ylmethoxy)-benzamide (5.0, 15.5 mmole) was dissolved in tetrahydrofuran (77 ml, 0.2M) and cooled to −78° C. under N$_2$. 1.2 eq. of the 4-picoline anion was added dropwise to the amide solution. After 45 min, 1 eq. more of the 4-picoline anion was added. After an addition 30 min, acetic acid (40 ml) was added dropwise and the reaction was slowly warmed to ambient temperature. The solid product (acetate salt) was filtered and partitioned between saturated sodium bicarbonate and dichloromethane. The layers were separated, dried magnesium sulfate filtered and concentrated to provide the title compound as a tan solid (4.41 g, 80%). $^1$H NMR (400 MHz, CDCl$_3$) δ 8.52 (d, J=5.8 Hz, 2 H), 8.19 (d, J=8.7 Hz, 1 H), 8.07 (d, J=8.7 Hz, 1H), 7.93 (m, 2 H), 7.82 (d, J=8.3 Hz, 1 H), 7.75 (m, 1 H), 7.61 (d, J=8.3 Hz, 1 H), 7.54 (dt, J=7.9, 1.0 Hz, 1 H), 7.23 (m, 2 H) 7.07 (m, 2H), 5.42 (s, 2H), 4.19 (s, 2H); MS: (M$^+$H m/z=355.2).

Preparation 5

3-Dimethylamino-2-pyridin-4-yl-1-[4-(quinolin-2-ylmethoxy)-phenyl}-propenone To 2-pyridin-4-yl-1-[4-(quinolin-2-ylmethoxy)-phenyl]-ethanone (4.0 g, 11.3 mmole) was added dimethoxymethyl-dimethyl amine (10 ml) and the reaction mixture was heated at reflux for 1 hr. Concentrated to give a quantitative yield of the title compound which was used as is in the next step. LC/MS: RT=1.4 min, MS: (M$^+$H m/z=410.2).

EXAMPLE 1

2-[-4-(4-Pyridin-4-yl-2H-pyrazol-3-yl)-phenoxymethyl]-quinoline

To a solution of 3-Dimethylamino-2-pyridin-4-yl-1-[4-(quinolin-2-ylmethoxy)-phenyl}-propenone (9.57 g, 27 mmole) in methanol was added hydrazine hydrate (3.33 g, 40.5 mmole) and the reaction mixture was heated at reflux for 1 h. The solvent was evaporated to yield a white solid. The solid was washed with water and ethyl ether. The solid was recrystallized from hot ethanol/ethylacetate (10 ml/g) to give 8.34 g of the title compound (82%). $^1$H NMR (400 MHz, DMSO) δ 8.41 (m, 3 H), 8.16 (s, 1 H), 7.97 (m, 2H), 7.86 (s, 1 H), 7.75 (t, J=7.9 Hz, 1 H), 7.68 (d, J=8.3 Hz, 1 H), 7.60 (t, J=7.5 Hz, 1 H), 7.33 (m, 2 H), 7.18 (m, 2 H) 7.15 (d, J=8.3 Hz, 1H), 7.06 (d, J=8.3 Hz, 1H), 5.38 (s, 2H); MS: (M$^+$H m/z=379.2).

EXAMPLE 2

2-[4-(2-Methyl-4-pyridin-4-yl-2H-pyrazol-3-yl)-phenoxymethyl]-quinoline

To a solution of 2-[4-(4-Pyridin-4-yl-2H-pyrazol-3-yl)-phenoxymethyl}-quinoline (1.72 g) in ethanol (20 ml) was added methyl hydrazine (3.5 ml, 1.5 eq.) and concentrated sulfuric acid (0.1 ml). The reaction mixture was stirred 1 h at ambient temperature and solvent evaporated. The reaction mixture was partitioned between methylene chloride and saturated sodium bicarbonate. The layers were separated and the organic layer dried magnesium sulfate, filtered and concentrated. Preparative HPLC chromatography provided the title compound (minor isomer) as a white solid (0.30 g, 17%). $^1$H NMR (400 MHz, CDCl$_3$) δ 8.31 (d, J=5.4 Hz, 2 H), 8.21 (d, J=8.7 Hz, 1 H), 7.80 (d, J=8.3 Hz, 1H), 7.77 (s, 1 H), 7.66 (m, 3 H), 7.53 (m, 1H), 7.19 (d, J=8.7 Hz, 2 H), 7.11 (d, J=8.7 Hz, 2H), 7.01 (d, J=6.2 Hz, 2H) 5.40 (s, 2H), 3.69 (s, 3H); MS: (M$^+$H m/z=393.3).

EXAMPLE 3

2-[4-(1-Methyl-4-pyridin-4-yl-1H-pyrazol-3-yl)-phenoxymethyl]-quinoline

To a solution of 2-[-4-(4-Pyridin-4-yl-2H-pyrazol-3-yl)-phenoxymethyl}-quinoline (1.72 g) in ethanol (20 ml) was added methyl hydrazine (3.5 ml, 1.5 eq.) and concentrated sulfuric acid (0.1 ml). The reaction mixture was stirred 1 h at ambient temperature and solvent evaporated. The reaction mixture was partitioned between methylene chloride and saturated sodium bicarbonate. The layers were separated and the organic layer dried magnesium sulfate, filtered and concentrated. Preparative HPLC chromatography provided the title compound (major isomer) as a clear oil (0.97 g, 56%). $^1$H NMR (400 MHz, CDCl$_3$) δ 8.44 (d, J=5.0 Hz, 2 H), 8.17 (d, J=8.7 Hz, 1 H), 8.05 (d, J=8.3 Hz, 1H), 7.81 (d, J=7.9 Hz, 1 H), 7.70 (m, 1 H), 7.66 (d, J=8.7 Hz, 1H), 7.54 (s, 1H), 7.53 (m, 1H), 7.37 (d, J=8.7 Hz, 2H) 7.15 (d, J=5.0, 2H), 7.00 (d, J=8.7 Hz, 2H), 5.38 (s, 2H), 3.93 (s, 3H); MS: (M$^+$H m/z=393.3).

EXAMPLE 4

2-[4-(2-Ethyl-4-pyridin-4-yl-2H-pyrazol-3-yl)-phenoxymethyl]-quinoline

Following the procedure for the preparation of 2-[4-(1-Methyl-4-pyridin-4-yl-1H-pyrazol-3-yl)-phenoxymethyl]-quinoline but substituting ethyl hydrazine provided the title compound. $^1$H NMR (400 MHz, CDCl$_3$) δ 8.35 (bs, 2H), 8.23 (d, J=8.3 Hz, 1 H), 8.08 (d, J=8.3 Hz, 1 H), 7.85 (d, J=7.4 Hz, 1H), 7.83 (s, 1 H), 7.74 (m, 2 H), 7.57 (t, J=7.9 Hz, 1H), 7.21 (d, J=8.7 Hz, 2 H), 7.14 (d, J=9.1 Hz, 2 H), 7.04 (m, 2H) 5.42 (s, 2H), 4.03 (q, J=7.5 Hz, 2H), 1.36 (t, J=7.5 Hz, 3H); MS: (M$^+$H m/z=407.3).

EXAMPLE 5

2-[4-(1-Ethyl-4-pyridin-4-yl-1H-pyrazol-3-yl)-phenoxymethyl]-quinoline

Following the procedure for the preparation of 2-[4-(1-Methyl-4-pyridin4-yl-1H-pyrazol-3-yl)-phenoxymethyl]-quinoline but substituting ethyl hydrazine provided the title compound. $^1$H NMR (400 MHz, CDCl$_3$) δ 8.35 (bs, 2H), 8.19 (d, J=8.3 Hz, 1 H), 8.07 (d, J=9.1 Hz, 1 H), 7.82 (d, J=7.9 Hz, 1H), 7.73 (t, J=8.3 Hz, 1H), 7.67 (d, J=8.3 Hz, 2 H), 7.62 (s, 1H), 7.55 (t, J=7.9 Hz, 1 H), 7.37 (d, J=9.1 Hz, 2H), 7.21 (bs, 2 H), 7.01 (d, J=8.7 Hz, 2H) 5.39 (s, 2H), 4.24 (q, J=7.5 Hz, 2H), 1.56 (t, J=7.5 Hz, 3H); MS: (M$^+$H m/z=407.3).

EXAMPLE 6

Dimethyl-(2-{4-pyridin-4-yl-3-[4-(quinolin-2-yl-methoxy)-phenyl]-pyrazol-1-yl}-ethyl)-amine Following the procedure for the preparation of 2-[4-(1-Methyl-4-pyridin4-yl-1H-pyrazol-3-yl)-phenoxymethyl]-quinoline but substituting (2-hydrazino-ethyl)-dimethyl-amine provided the title compound. $^1$H NMR (400 MHz, CDCl$_3$) δ 8.44 (dd, J=4.6, 1.7, Hz, 2 H), 8.18 (d, J=8.3 Hz, 1 H), 8.06 (d, J=8.3 Hz, 1H), 7.82 (d, J=8.7 Hz, 1 H), 7.71 (m 2H), 7.55 (t, J=7.1 Hz, 1H), 7.38 (d, J=8.7 Hz, 2H), 7.15 (d, J=6.2 Hz, 2H) 7.00 (d, J=8.7 Hz, 2H), 5.38 (s, 2H), 4.25 (t, J=6.6 Hz, 2H), 2.82 (t, J=6.6 Hz, 2H), 2.28 (s, 6H); MS: (M$^+$H m/z=450.4).

EXAMPLE 7

Dimethyl-(2-{4-pyridin-4-yl-5-[4-(quinolin-2-yl-methoxy)-phenyl]-pyrazol-1-yl}-ethyl)-amine Following the procedure for the preparation of 2-[4-(1-Methyl-4-pyridin4-yl-1H-pyrazol-3-yl)-phenoxymethyl]-quinoline but substituting (2-hydrazino-ethyl)-dimethyl-amine provided the title compound. $^1$H NMR (400 MHz, CDCl$_3$) δ 8.35 (d, J=6.2 Hz, 2 H), 8.22 (d, J=8.3 Hz, 1 H), 8.08 (d, J=8.7 Hz, 1H), 7.85 (m, 2 H), 7.73 (m, 2H), 7.57 (t, J=7.1 Hz, 1H), 7.23 (m, 2H), 7.17 (d, J=9.1 Hz, 2H) 7.00 (d, J=6.2 Hz, 2H), 5.42 (s, 2H), 4.05 (t, J=6.6 Hz, 2H), 2.66 (t, J=7.1 Hz, 2H), 2.10 (s, 6H); MS: (M$^+$H m/z=450.4).

EXAMPLE 8

2-{4-[-Pyridin4-yl-2-(2,2,2-trifluoro-ethyl)-2H-pyrazol-3-yl]-phenoxymethyl}-quinoline Following the procedure for the preparation of 2-[4-(1-Methyl-4-pyridin4-yl-1H-pyrazol-3-yl)-phenoxymethyl]-quinoline but substituting (2,2,2-trifluoro-ethyl)-hydrazine provided the title compound. MS: (M$^+$H m/z=461.2).

EXAMPLE 9

2-{4-[-Pyridin-4-yl-1-(2,2,2-trifluoro-ethyl)-1H-pyrazol-3-yl]-phenoxymethyl}-quinoline To a solution of 2-[4-(4-Pyridin4-yl-2H-pyrazol-3-yl)-phenoxymethyl}-quinoline (26.5 g) in dimethyl formamide (140 mL) was added 1,1,1-Trifluoro-2-iodo-ethane (21 mL, 2.0 eq.) and cesium carbonate (68.3 g, 3 eq.) and the reaction mixture heated at 60° C. for 24 h. The reaction mixture was diluted with water, extracted 3× methylene chloride, dried with magnesium sulfate, filtered and concentrated. Purification via flash chromatography eluting with 5% methanol/70% ethyl acetate/hexanes provided the title compound 20.85 g as an 8:1 regioisomeric mixture. Preparative HPLC eluting with acetonitile/methanol (98:2) on a chiralpak AD column with a flow rate of 430 ml/Min provided the pure title compound as a free base 13.4 g. $^1$H NMR (400 MHz, CDCl$_3$) δ 8.45 (m, 2 H), 8.16 (d, J=8.3 Hz, 1 H), 8.04 (d, J=8.3 Hz, 1H), 7.96 (s, 1H), 7.79 (d, J=8.3 Hz, 1 H), 7.69 (m, 1 H), 7.64 (d, J=8.3 Hz, 1 H), 7.50 (m, 1H), 7.36 (d, J=8.7 Hz, 2H), 7.14 (d, J=6.2 Hz, 2H), 6.98 (d, J=9.1 Hz, 2 H), 5.35 (s, 2H), 4.75 (q, J=8.3 Hz, 2 H); MS: (M$^+$H m/z=427.1).MS: (M$^+$H m/z=461.2).

EXAMPLE 10

1-{4-Pyridin-4-yl-3-[4-(quinolin-2-ylmethoxy)-phenyl]-pyrazol-1-yl}-propan-2-ol

Following the procedure for the preparation of 2-[4-(1-Methyl-4-pyridin-4-yl-1H-pyrazol-3-yl)-phenoxymethyl]-quinoline but substituting 1-hydrazino-propan-2-ol provided the title compound. $^1$H NMR (400 MHz, CDCl$_3$) δ 8.44 (bs, 2 H), 8.20 (d, J=8.3 Hz, 1 H), 8.08 (d, J=8.3 Hz, 1H), 7.83 (d, J=8.3 Hz, 1 H), 7.75 (m 2H), 7.67 (d, J=8.3 Hz, 1H), 7.56 (t, J=8.3 Hz, 1H), 7.36 (d, J=8.7 Hz, 2H) 7.30 (m, 2H), 7.03 (d, J=9.1 Hz, 2 H), 5.40 (s, 2H), 4.49 (m, 1H), 4.23 (m, 1H), 4.02 (m, 1H), 1.83 (m, 1H), 1.28 (d, J=6.2 Hz, 3H); MS: (M$^+$H m/z=437.2).

EXAMPLE 11

1-{4-Pyridin-4-yl-5-[4-(quinolin-2-ylmethoxy)-phenyl]-pyrazol-1-yl}-propan-2-ol

Following the procedure for the preparation of 2-[4-(1-Methyl-4-pyridin4-yl-1H-pyrazol-3-yl)-phenoxymethyl]-quinoline but substituting 1-hydrazino-propan-2-ol provided the title compound. $^1$H NMR (400 MHz, CDCl$_3$) δ 8.37 (d, J=6.2 Hz, 2 H), 8.23 (d, J=8.7 Hz, 1 H), 8.08 (d, J=8.3 Hz, 1H), 7.84 (m, 2 H), 7.75 (m, 2H), 7.57 (t, J=6.6 Hz, 1H), 7.20 (d, J=9.1 Hz, 2H), 7.13 (d, J=8.7 Hz, 2H) 7.00 (dd, J=6.2, 1.7 Hz, 2H), 5.42 (s, 2H), 4.17 (m, 1H), 3.94 (m, 2H), 3.86 (m, 1H), 1.12 (d, J=6.6 Hz, 3H); MS: (M$^+$H m/z=437.3).

EXAMPLE 12

2-[4-(2-Isopropyl-4-pyridin-4-yl-2H-pyrazol-3-yl)-phenoxymethyl]-quinoline

Following the procedure for the preparation of 2-[4-(1-Methyl-4-pyridin-4-yl-1H-pyrazol-3-yl)-phenoxymethyl]-quinoline but substituting isopropyl hydrazine provided the title compound. $^1$H NMR (400 MHz, CDCl$_3$) δ 8.33 (bs, 2 H), 8.24 (d, J=8.3 Hz, 1 H), 8.08 (d, J=8.3 Hz, 1H), 7.86 (s, 1H) 7.83 (m, 1 H), 7.72 (m 2H), 7.58 (t, J=7.9 Hz, 1H), 7.20 (d, J=8.7 Hz, 2H), 7.15 (d, J=9.1 Hz, 2H) 7.04 (m, 2H), 5.43 (s, 2H), 4.31 (m, 1H), 1.43 (d, J=6.6 Hz), 6H); MS: (M$^+$H m/z=421.2).

EXAMPLE 13

2-[4-(4-Pyridin-4yl-isoxazol-5-yl)-phenoxymethyl]-quinoline 2-pyridin-4-yl-1-[4-(quinolin-2-ylmethoxy)-phenyl]-ethanone (200 mg, 0.56 mmole) was heated at reflux in dimethoxymethyl-dimethyl amine (1 ml) for 1 h and concentrated. The crude product was dissolved in methanol/water (3:1, 4 ml) and hydroxyl amine hydrochloride (43 mg, 1.1 eq.) was added. After 1 h, acetic acid was added (0.016 ml) and the reaction was heated at reflux for 1h. Cooled to ambient temperature poured into saturated sodium bicarbonate, extracted with methylene chloride, dried magnesium sulfate, filtered and concentrated. Biotage MPLC was run on a 25S column elution with 3% methanol/1% ammonium hydroxide/ethyl acetate 50% in hexanes to provide the title compound as a tan solid (94 mg, 45%). $^1$H NMR (400 MHz, CDCl$_3$) δ 8.59(dd, J=6.2, 1.7 Hz, 2 H), 8.36 (s, 1H), 8.20 (d, J=8.3 Hz, 1H), 8.07 (d, J=8.7 Hz, 1 H), 7.82 (d, J=9.1 Hz, 1H), 7.73 (dt, J=7.1, 1.7 Hz, 1H), 7.64 (d, J=8.3 Hz, 1H), 7.54 (m, 3H), 7.28 (d, J=4.2 Hz, 2H) 7.05 (d, J=9.1, 2H), 5.40 (s, 2H); MS: (M$^+$H m/z=380.2).

EXAMPLE 14

2-[4-(5-Pyridin-4-yl-pyrimidin-4-yl)-phenoxymethyl]-quinoline 2-pyridin-4-yl-1-[4-(quinolin-2-ylmethoxy)-phenyl]-ethanone (200 mg) was heated at reflux in dimethoxymethyl-dimethyl amine (1 ml) for 1 h and concentrated. The crude reaction mixture was dissolved in ethanol (3 ml) and formamidine hydrochloride (90 mg, 2 eq.) was added. In a separate flask sodium (40 mg) was added to ethanol 3 ml and stirred 10 min. The sodium ethoxide solution was added to the reaction mixture and was heated at reflux for 1 h. The reaction mixture was concentrated and purified via Biotage MPLC chromatography on a 25S column eluting with 40-100% ethyl acetate/hexane to provide the title compound (83 mg, 38%). $^1$H NMR (400 MHz, CDCl$_3$) δ 8.53(m, 3 H), 8.14 (d, J=8.7 Hz, 1H), 8.03 (d, J=8.3 Hz, 1H), 7.79 (d, J=7.9 Hz, 1 H), 7.70 (m, 1 H), 7.58 (d, J=8.7 Hz, 1H), 7.50 (m, 1H), 7.33 (d, J=9.1 Hz, 2H) 7.10 (d, J=6.2, 2H), 6.91(d, J=9.1 Hz, 2H), 5.34 (s, 2H) 2.77 (s, 3H); MS: (M$^+$H m/z=391.2).

EXAMPLE 15

2-[4-(2-Methyl-5-pyridin-4-yl-pyrimidin-4-yl)-phenoxymethyl]-quinoline

Following the procedure for the preparation of 2-[4-(5-Pyridin-4-yl-pyrimidin-4-yl)-phenoxymethyl]-quinoline but substituting acetamidine hydrochloride provide the title compound. $^1$H NMR (400 MHz, CDCl$_3$) δ 9.21 (s, 1H), 8.63 (S, 1H), 8.58(m, 2 H), 8.17 (d, J=8.7 Hz, 1H), 8.04 (d, J=8.7 Hz, 1H), 7.81 (d, J=8.3 Hz, 1 H), 7.70 (m, 1 H), 7.60 (d, J=8.3 Hz, 1H), 7.52 (m, 1H), 7.37 (m, 2H) 7.15 (d, J=6.2, 2H), 6.93 (d, J=9.1 Hz, 2H), 5.35 (s, 2H); MS: (M$^+$H m/z=405.2).

EXAMPLE 16

2-[4-(2-Methyl-6-pyridin-4-yl-pyrazolo[1,5-a]pyrimidin-7-yl)-phenoxymethyl]-quinoline To a solution of 3-Dimethylamino-2-pyridin-4-yl-1-[4-(quinolin-2-ylmethoxy)-phenyl}-propenone (229 mg, 0.56 mmole) in ethanol (3 ml) was added piperidine (2 eq.) and 5-methyl-2H-pyrazol-3-ylamine (108 mg, 2 eq.) and the reaction mixture was heated at reflux for 3 h. The reaction mixture was cooled to RT, filtered and product washed with ethanol and hexane to provide the title compound (96 mg, 39%). $^1$H NMR (400 MHz, CDCl$_3$) δ 8.51 (d, J=7.9 Hz, 2H), 8.46 (S, 1H), 8.30(m, 1 H), 8.18 (m, 1H), 7.89 (d, J=8.3 Hz, 1H), 7.78 (m, 1 H), 7.71 (m, 1 H), 7.60 (m, 1 H), 7.41 (d, J=8.7, 2H), 7.21 (m, 2H) 7.07 (d, J=8.7, 2H), 6.60 (s, 1H), 5.50 (s, 2H) 2.48 (s, 3H); MS: (M$^+$H m/z=444.2).

EXAMPLE 17

2-[4-(2-Methyl-6-pyridin-4-yl-[1,2,4]triazolo[1.5-a]pyrimidin-7-yl)-phenoxymethyl]-quinoline Following the procedure for the preparation of 2-[4-(2-Methyl-6-pyridin-4-yl-pyrazolo[1,5-a]pyrimidin-7-yl)-phenoxymethyl]-quinoline but substituting 5-Methyl-2H-[1,2,4]-triazol-3ylamine provided the title compound. $^1$H NMR (400 MHz, CDCl$_3$) δ 8.75 (s, 1H), 8.55 (m, 2H), 8.21(d, J=8.3 Hz, 1 H), 8.06 (d, J=7.5 Hz, 1H), 7.84 (d, J=7.1 Hz, 1H), 7.73 (m, 1H), 7.64 (d, J=8.3 Hz, 1 H), 7.55 (m, 1H), 7.42 (d, J=8.7, 2H), 7.08 (m, 4H), 5.39 (s, 2H) 2.60 (s, 3H); MS: (M$^+$H m/z=445.2).

Preparation 6

2-Pyridazin-4-yl-1-[4-(quinolin-2-ylmethoxy)-phenyl]-ethanone

Following the procedure for the preparation of 2-pyridin-4-yl-1-[4-(quinolin-2-ylmethoxy)-phenyl]-ethanone but substituting 4-methyl pyridazine for 4-picoline provided the title compound. $^1$H NMR (400 MHz, CDCl$_3$) δ 9.12 (d, J=5.4 Hz, 1 H), 9.08 (d, J=8.7 Hz, 2.1 H), 8.20 (d, J=8.3 Hz, 1H), 8.07 (d, J=8.3 Hz, 1 H), 7.96 (m, 2 H), 7.83 (d, J=7.9 Hz, 1 H), 7.76 (m, 1 H), 7.62 (d, J=8.3 Hz, 1 H), 7.55 (m, 1 H) 7.38 (dd, J=5.4, 2.5 Hz, 1H), 7.09 (m, 2H), 5.44 (s, 2H) 4.23 (s, 2H); MS: (M$^+$H m/z=356.2).

Preparation 7

3-Dimethylamino-2-pyridazin-4-yl-1-[4-(quinolin-2-ylmethoxy)-phenyl]-propenone Following the procedure for the preparation of 3-Dimethylamino-2-pyridin-4-yl-1-[4-(quinolin-2-ylmethoxy)-phenyl}-propenone but substituting 2-Pyridazin-4-yl-1-[4-(quinolin-2-ylmethoxy)-phenyl]-ethanone provided the title compound. LC/MS: RT=1.8 min, MS: (M$^+$H m/z=411.2).

EXAMPLE 18

2-[4-(4-Pyridazin-4-yl-2H-pyrazol-3-yl)-phenoxymethyl]-quinoline

Following the procedure for the preparation of 2-[-4-(4-Pyridin-4-yl-2H-pyrazol-3-yl)-phenoxymethyl}-quinoline but substituting 3-Dimethylamino-2-pyridazin-4-yl-1-[4-(quinolin-2-ylmethoxy)-phenyl]-propenone provided the title compound as a white solid. $^1$H NMR (400 MHz, CDCl$_3$) δ 9.11 (s, 1H), 9.01 (d, J=5.0 Hz, 1H), 8.34(d, J=8.7 Hz, 1 H), 8.25 (d, J=8.7 Hz, 1H), 7.89 (m 2H), 7.81 (d, J=8.3 Hz, 1 H), 7.79 (m, 2 H), 7.61 (t, J=7.6 Hz, 1H), 7.34 (m, 1H), 7.31 (d, J=8.7 Hz, 2H), 7.05 (d, J=8.7, 2H), 5.49 (s, 2H); MS: (M$^+$H m/z=380.2).

EXAMPLE 19

2-[4-(1-Methyl-4-pyridazin-4-yl-1H-pyrazol-3-yl)-phenoxymethyl]-quinoline

Following the procedure for the preparation of 2-[4-(1-Methyl-4-pyridin-4-yl-1H-pyrazol-3-yl)-phenoxymethyl]-quinoline but substituting 3-Dimethylamino-2-pyridazin-4-yl-1-[4-(quinolin-2-ylmethoxy)-phenyl]-propenone provided the title compound as a white solid. $^1$H NMR (400 MHz, CDCl$_3$) δ 9.11 (d, J=2.5 Hz, 1H), 8.96 (d, J=5.4 Hz, 1H), 8.19(d, J=8.7 Hz, 1H), 8.06 (d, J=8.3 Hz, 1H), 7.82 (d, J=7.9 Hz, 1H), 7.73 (t, J=7.1 Hz, 1 H), 7.67 (m, 2H), 7.55 (t, J=7.1 Hz, 1H), 7.34 (d, J=9.1 Hz, 2H), 7.24 (m, 1H), 7.02 (d, J=6.6 Hz, 2H), 5.39 (s, 2H) 3.97 (s, 3H); MS: (M$^+$H m/z=394.2).

EXAMPLE 20

2-[4-(2-Methyl-4-pyridazin4-yl-2H-pyrazol-3-yl)-phenoxymethyl]-quinoline

Following the procedure for the preparation of 2-[4-(1-Methyl-4-pyridin4-yl-1H-pyrazol-3-yl)-phenoxymethyl]-quinoline but substituting 3-Dimethylamino-2-pyridazin4-yl-1-[4-(quinolin-2-ylmethoxy)-phenyl]-propenone provided the title compound as a white solid. $^1$H NMR (400 MHz, CDCl$_3$) δ 8.99 (d, J=2.5 Hz, 1H), 8.90 (d, J=5.4 Hz, 1H), 8.24(d, J=8.7 Hz, 1H), 8.08 (d, J=8.7 Hz, 1H), 7.89 (s, 1H), 7.85 (d, J=8.3 Hz, 1 H), 7.75 (t, J=7. 1 Hz, 1 H), 7.70 (d, J=8.3 Hz, 1H), 7.57 (t, J=7.1 Hz, 1H), 7.21 (d, J=8.7 Hz, 2H), 7.15 (d, J=9.1 Hz, 2H), 7.11 (m, 1 H), 5.43 (s, 2H) 3.73 (s, 3H); MS: (M$^+$H m/z=394.2).

EXAMPLE 21

2-[-4-(4-Pyrimidin-4yl-2H-pyrazol-3-yl)-phenoxymethyl]-quinoline

Following the procedure for the preparation of 2-[4-(4-Pyridin-4-yl-2H-pyrazol-3-yl)-phenoxymethyl}-quinoline and making the necessary chemical substitutions provided the title compound as a white solid. LC/MS: RT=1.8 min, MS: (M$^+$H m/z=380.2).

EXAMPLE 22

2-[4-(4-Pyridazin-3-yl-2H-pyrazol-3-yl)-phenoxymethyl]-quinoline

Following the procedure for the preparation of 2-[-4-(4-Pyridin-4-yl-2H-pyrazol-3-yl)-phenoxymethyl}-quinoline and making the necessary chemical substitutions provided the title compound as a white solid. LC/MS: RT=1.7 min, MS: (M$^+$H m/z=380.2).

Preparation 8

2-(3-Methyl-isoxazol-5-yl)-1-[4-(quinolin-2-ylmethoxy)-phenyl]-ethanone

Following the procedure for the preparation of 2-pyridin-4-yl-1-[4-(quinolin-2-ylmethoxy)-phenyl]-ethanone but substituting 3,5-dimethyl isoxazole for 4-picoline provided the title compound. LC/MS: RT=2.3 min, MS: (M$^+$H m/z=359.2).

Preparation 9

3-Dimethylamino-2-(3-methyl-isoxazol-5-yl)-1-[4-(quinolin-2-ylmethoxy)-phenyl]-propenone Following the procedure for the preparation of 3-Dimethylamino-2-pyridin4-yl-1-[4-(quinolin-2-ylmethoxy)-phenyl}-propenone but 2-(3-Methyl-isoxazol-5-yl)-1-[4-(quinolin-2-ylmethoxy)-phenyl]-ethanone provided the title compound. LC/MS: RT=2.1 min, MS: (M$^+$H m/z=414.2).

EXAMPLE 23

2-{4-[4-(3-Methyl-isoxazol-5-yl)-2H-pyrazol-3-yl]-phenoxymethyl}-quinoline

Following the procedure for the preparation of 2-[-4-(4-Pyridin-4-yl-2H-pyrazol-3-yl)-phenoxymethyl}-quinoline but substituting 3-Dimethylamino-2-(3-methyl-isoxazol-5-yl)-1-[4-(quinolin-2-ylmethoxy)-phenyl]-propenone provided the title compound. $^1$H NMR (400 MHz, CDCl$_3$) δ 8.23 (d, J=8.7 Hz, 1H), 8.12 (d, J=8.7 Hz, 1H), 7.94(s, 1 H), 7.84 (d, J=7.1 Hz, 1H), 7.74 (m, 1H), 7.69 (d, J=8.3 Hz, 1 H), 7.57 (t, J=6.6 Hz, 2 H), 7.46 (d, J=8.87 Hz, 2H), 7.08 (d, J=8.7 Hz, 2H), 5.88 (s, 1H), 5.42 (s, 2H), 2.23 (s, 3H); MS: (M$^+$H m/z=383.2).

EXAMPLE 24

2-{4-[2-Methyl-4-(3-methyl-isoxazol-5-yl)-2H-pyrazol-3-yl]-phenoxymethyl)-quinoline Following the procedure for the preparation of 2-[4-(1-Methyl-4-pyridin-4-yl-1H-pyrazol-3-yl)-phenoxymethyl]-quinoline but substituting 3-Dimethylamino-2-(3-methyl-isoxazol-5-yl)-1-[4-(quinolin-2-ylmethoxy)-phenyl]-propenone provided the title compound as a white solid. $^1$H NMR (400 MHz, CDCl$_3$) δ 8.25 (d, J=8.7 Hz, 1H), 8.12 (d, J=8.3 Hz, 1H), 7.89(s, 1 H), 7.85 (d, J=8.3 Hz, 1H), 7.74 (m, 2H), 7.57 (t, J=7.1 Hz, 1 H), 7.28 (s, 1 H), 7.26 (d, J=10.4 Hz, 2H), 7.16 (d, J=8.7 Hz, 2H), 5.45 (s, 2H), 3.71 (s, 3H), 2.16 (s, 3H); MS: (M$^+$H m/z=397.2).

EXAMPLE 25

2-{4-[1-Methyl-4-(3-methyl-isoxazol-5-yl)-1H-pyrazol-3-yl]-phenoxymethyl}-quinoline Following the procedure for the preparation of 2-[4-(1-Methyl-4-pyridin4-yl-1H-pyrazol-3-yl)-phenoxymethyl]-quinoline but substituting 3-Dimethylamino-2-(3-methyl-isoxazol-5-yl)-1-[4-(quinolin-2-ylmethoxy)-phenyl]-propenone provided the title compound as a white solid. $^1$H NMR (400 MHz, CDCl$_3$) δ 8.18 (d, J=8.3 Hz, 1H), 8.07 (d, J=8.7 Hz, 1H), 7.81(d, J=7.1 Hz, 1 H), 7.77 (s, 1H), 7.74 (t, J=7.1 Hz, 1H), 7.67 (d, J=8.7 Hz, 1 H), 7.54 (t, J=7.1 Hz, 1H), 7.48 (d, 8.7 Hz, 2H), 7.07 (d, J=8.7 Hz, 2H), 5.81 (s, 1H), 5.41 (s, 2H), 3.92 (s, 3H), 2.20 (s, 3H); MS: (M$^+$H m/z=397.2).

EXAMPLE 26

2-{4-[2-Methyl-5-(3-methyl-isoxazol-5-yl)-pyrimidin-4-yl]-phenoxymethyl}-quinoline Following the procedure for the preparation of 2-[4-(5-Pyridin-4-yl-pyrimidin-4-yl)-phenoxymethyl]-quinoline but substituting acetamidine hydrochloride and 3-Dimethylamino-2-(3-methyl-isoxazol-5-yl)-1-[4-(quinolin-2-ylmethoxy)-phenyl]-propenone provided the title compound as the hydrochloride salt. $^1$H NMR (400 MHz, CDCl$_3$) δ 8.87 (s, 1H), 8.18 (d, J=8.3 Hz, 1H), 8.06 (d, J=8.3 Hz, 1H), 7.82(d, J=8.3 Hz, 1 H), 7.72 (t, J=7.1 Hz, 1H), 7.63 (d, J=8.7 Hz, 1H), 7.53 t, J=6.6 Hz, 1 H), 7.45 (d, J=9.1 Hz, 2H), 7.05 (d, J=9.1 Hz, 2H), 5.79 (s, 1H), 5.40 (s, 2H), 2.78 (s, 3H), 2.23 (s, 3H); MS: (M$^+$H m/z=409.2).

Preparation 10

1-[4-(Quinolin-2-ylmethoxy)-phenyl]-ethanone

To a solution of 2-Chloromethyl quinoline (2.5 g, 14 mmole) in acetone (47 ml) was added 4-hydroxy acetophenone (1.92 g, 1.0 eq.) and potassium carbonate (2.5 g, 2 eq.). The reaction mixture was heated at 60° C. for 16 h under N$_2$ atmosphere, cooled to ambient temperature and poured into 1N sodium hydroxide (50 ml)/ethyl acetate (100 ml). The layers were separated and the organic layer dried magnesium sulfate, filtered and concentrated. Biotage MPLC was run using a 5-40% ethyl acetate/hexane gradient on a 40 M column to provide the title compound as a white solid (2.75 g, 71%). $^1$H NMR (400 MHz, CDCl$_3$) δ 8.19 (d, J=8.7 Hz, 1 H), 8.07 (d, J=8.7, 1H), 7.91 (m, 2H), 7.82 (dd, J=8.3, 1.3 1H), 7.73 (t, J=7.1 Hz, 1 H), 7.62 (d, J =8.3 Hz, 1 H), 7.54 (t, J=7.1 Hz, 1 H), 7.06 (m, 2H), 5.42 (s, 2 H), 2.51 (s, 3 H); MS: (M$^+$H m/z=278.3).

Preparation 11

3-Dimethylamino-1-[4-(quinolin-2-ylmethoxy)-phenyl]-propenone

1-[4-(Quinolin-2-ylmethoxy)-phenyl]-ethanone (1.0 g, 3.61 mmole) was stirred in dimethoxymethyl-dimethyl amine (5 ml) and heated at reflux for 18 h. The reaction mixture was cooled to RT and a tan precipitate formed. It was filtered and washed with ethyl ether to provide the title compound 840 mg, 71%). $^1$H NMR (400 MHz, CDCl$_3$) δ 8.39 (d, J=8.3 Hz, 1 H), 7.97 (m, 2H), 7.91 (m, 2H), 7.84 (m, 2H), 7.75 (t, J=6.6 Hz, 1 H), 7.62 (m, 3H), 7.05 (d, J=8.7 Hz, 2 H), 5.77 (d, J=12.0, 1H), 5.40 (s, 2 H), 3.07 (bs, 3 H), 2.84 (bs, 3H); MS: (M$^{+H\ m/z=}$333.3).

EXAMPLE 27

2-[4-(2-Pyridin-4-yl-2H-pyrazol-3-yl)-phenoxymethyl]-quinoline

To a solution of 3-Dimethylamino-1-[4-(quinolin-2-ylmethoxy)-phenyl]-propenone (46 mg) in ethanol (0.7 ml) was added water (0.7 ml), acetic acid (0.05ml) and 4-pyridyl hydrazine (25 mg, 1 eq.). The reaction mixture was heated at 100° C. for 3 h, cooled to RT, poured into 1 N NaOH, extracted with chloroform, dried magnesium sulfate, filtered and concentrated. Biotage MPLC was run on a 25S column eluting with 20-80% ethyl acetate/hexane to provide the title compound as a tan solid (31 mg, 61%). $^1$H NMR (400 MHz, CDCl$_3$)δ 8.51 (bs, 2H), 8.24 (d, J=8.7 Hz, 1 H), 8.11 (d, J=8.7, 2H), 7.84 (d, J=8.3 Hz, 1H), 7.74 (m, 2H), 7.69 (d, J=8.7 Hz, 1 H), 7.58 (t, J=7.1, 1H), 7.32 (bs, 2H), 7.19 (d, J=6.6 Hz, 2H), 7.04 (d, J=6.6, 2H), 5.40 (s, 2 H), 6.45 (s, 1H), 5.42 (s, 2H); MS: (M$^+$H m/z=379.2).

EXAMPLE 28

2-[4-(3-Methyl-5-pyridin-4-yl [1,2,4]triazol-4-yl)-phenoxymethyl]-quinoline

To a solution of isonicotinic hydrazide (1.04 g, 1.12 eq.) in acetonitrile (30 ml) was added N,N-dimethylacetamide dimethyl acetal (1.1 eq.) and the reaction mixture was heated at 50° C. for 3 h. The reaction mixture was cooled to ambient temperature and concentrated. 4-(Quinolin-2-ylmethoxy)-phenylamine (1.70 g) was added along with acetic acid (30 ml) and the reaction mixture was heated at reflux for 3 h, and cooled to ambient temperature. The reaction mixture was concentrated on a rotovap and purified via combiflash MPLC to provide the title compound as a tan solid (56%). $^1$H NMR (400 MHz, CDCl$_3$) δ 8.51 (d, J=6.2 Hz, 2H), 8.24 (d, J=8.7 Hz, 1 H), 8.08 (d, J=8.7, 1H), 7.85 (d, J=7.9 Hz, 1H), 7.76 (t, J=8.3 Hz, 1H), 7.67 (d, J=8.7 Hz, 1 H), 7.58 (t, J=7.1, 1H), 7.29 (d, J=6.2 Hz, 2 H), 7.17 (d, J=9.1 Hz, 2H), 7.12 (d, J=9.1 Hz, 2 H), 5.43 (s, 2 H), 2.31 (s, 3H); MS: (M$^+$H m/z=394.3).

Preparation 12

4-benzyloxy-N-methoxy-N-methyl-benzamide

Following the procedure for the preparation of N-Methoxy-N-methyl-4-(quinolin-2-ylmethoxy)-benzamide but substituting 4-benzyloxy benzoic acid provided the title compound as a waxy solid. MS: (M$^+$H m/z=272.3).

Preparation 13

1-(4-Benzyloxy-phenyl)-2-pyridin-4-yl-ethanone

Following the procedure for the preparation of 2-pyridin-4-yl-1-[4-(quinolin-2-ylmethoxy)-phenyl]-ethanone but substituting 4-benzyloxy-N-methoxy-N-methyl-benzamide provided the title compound. MS: (M$^+$H m/z=304.2).

Preparation 14

4-[3-(4-Benzyloxy-phenyl)-1-methyl-1H-pyrazol-4-yl]-pyridine

Following the procedure for the preparation of 2-[4-(1-Methyl-4-pyridin-4-yl-1H-pyrazol-3-yl)-phenoxymethyl]-quinoline but substituting 1-(4-Benzyloxy-phenyl)-2-pyridin-4-yl-ethanone provided the title compound. MS: (M$^+$H m/z=342.2).

Preparation 15

4-(1-Methyl-4-pyridin-4-yl-1H-pyrazol-3-yl)-phenol

To a solution of 4-[3-(4-Benzyloxy-phenyl)-1-methyl-1H-pyrazol-4-yl]-pyridine (1.28 g) in ethanol (50 ml)/ethyl acetate (50 ml) in a parr bottle was added Palladium hydroxide (500 mg). The parr bottle was charged to 40 psi on a shaker for 6 h. The reaction mixture was filtered and concentrated. MPLC biotage chromatography eluting with methanol (1-7%)/chloroform provided the title compound (860 mg, 91%). $^1$H NMR (400 MHz, DMSO) δ 9.53 (s, 1H), 8.39 (d, J=5.8 Hz, 2 H), 7.15 (m, 4H), 6.72 (d, J=8.7 Hz, 1H), 3.84 (s, 3H); MS: ($M^+$H m/z=252.2).

EXAMPLE 29

2-[4-(1-Methyl-4-pyridin-4-yl-1H-pyrazol-3-yl)-phenoxymethyl]-quinoxaline

To a solution of 4-(1-Methyl4-pyridin-4-yl-1H-pyrazol-3-yl)-phenol (50 mg) in dioxane (2 ml) was added triphenylphosphine (84 mg), quinoxaline-2-yl-methanol (48 mg) and di-t-butyl-aza-dicarboxylate (73 mg) and the reaction mixture was heated at 60° C. for 18 h. The reaction mixture was poured into 1N NaOH, extracted 3× methylene chloride, dried magnesium sulfate, filtered and concentration Purification via MPLC biotage chromatography provided the title compound (54 mg, 67%). $^1$H NMR (400 MHz, CDCl$_3$) δ 9.09 (s, 1H), 8.45 (d, J=6.2 Hz, 2H), 8.10 (m, 2 H), 7.77 (m, 2H), 7.55 (s, 1H), 7.37 (d, J=9.1 Hz, 2H), 7.10 (d, J=6.9 Hz, 2 H), 7.01 (d, J=8.7, 2H), 5.41 (s, 2 H), 3.94 (s, 3H); MS: ($M^+$H m/z=394.4).

EXAMPLE 30

7-Chloro-2-[4-(1-methyl-4-pyridin-4-yl-1H-pyrazol-3-yl)-phenoxymethyl]-quinoline hydrogen chloride Following the procedure for the preparation of 4-(Quinolin-2-ylmethoxy)-benzoic acid methyl ester but substituting 4-(1-Methyl-4-pyridin-4-yl-1H-pyrazol-3-yl)-phenol and 7-chloro-2-chloromethyl-quinoline provided the title compound. $^1$H NMR (400 MHz, DMSO) δ 8.66 (d, J=6.6 Hz, 2H), 8.54 (s, 1 H), 8.47 (d, J=8.3, 2H), 8.04 (m, 2H), 7.70 (m, 2H), 7.65 (m, 1H), 7.36 (d, J=8.7 Hz, 2H), 7.12 (d, J=8.7, 2H), 5.38 (s, 2H), 3.90 (s, 3 H); MS: ($M^+$H m/z=427.1).

EXAMPLE 31

6-Fluoro-2-[4-(1-methyl-4-pyridin-4-yl-1H-pyrazol-3-yl)-phenoxymethyl]-quinoline hydrogen chloride Following the procedure for the preparation of 7-Chloro-2-[4-(1-methyl-4-pyridin-4-yl-1H-pyrazol-3-yl)-phenoxymethyl]-quinoline hydrogen chloride but substituting 2-chloromethyl-6-fluoro-quinoline provided the title compound. $^1$H NMR (400 MHz, DMSO) δ 8.67 (d, J=6.6 Hz, 2H), 8.55 (s, 1 H), 8.42 (d, J=8.3, 1H), 8.04 (m, 1H), 7.82 (m, 1H), 7.71 (m, 4H), 7.36 (d, J=8.7 Hz, 2H), 7.12 (d, J=8.7, 2H), 5.37 (s, 2H), 3.91 (s, 3 H); MS: ($M^+$H m/z=411.2).

Preparation 16

3-Fluoro-4-(quinolin-2-ylmethoxy)-benzoic acid quinolin-2-ylmethyl ester

Following the procedure for the preparation of 4-(Quinolin-2-ylmethoxy)-benzoic acid methyl ester but substituting 3-fluoro-4-hydroxy-benzoic acid provided the title compound. MS: ($M^+$H m/z=439.0).

Preparation 17

3-Fluoro-4-(quinolin-Z-ylmethoxy)-benzoic acid

Following the procedure for the preparation of 4-(Quinolin-2-ylmethoxy)-benzoic acid but substituting 3-Fluoro-4-(quinolin-2-ylmethoxy)-benzoic acid quinolin-2-ylmethyl ester provided the title compound. MS: ($M^+$H m/z=298.2).

Preparation 18

3-Fluoro-N-methoxyl-N-methyl-4-(quinolin-2-ylmethoxy)-benzamide

Following the procedure for the preparation of N-Methoxy-N-methyl-4-(quinolin-2-ylmethoxy)-benzamide but substituting 3-Fluoro-4-(quinolin-2-ylmethoxy)-benzoic acid provided the title compound. MS: ($M^+$H m/z=341.2).

Preparation 19

1-[3-Fluoro-4-(quinolin-2-ylmethoxy)-phenyl]-2-pyridin-4-yl-ethanone

Following the procedure for the preparation of 2-pyridin-4-yl-1-[4-(quinolin-2-ylmethoxy)-phenyl]-ethanone but substituting 3-Fluoro-N-methoxyl-N-methyl-4-(quinolin-2-ylmethoxy)-benzamide provided the title compound. MS: ($M^+$H m/z=373.1).

EXAMPLE 32

2-[2-Fluoro-4-(4-pyridin-4-yl-1H-pyrazol-3-yl)-phenoxymethyl]-quinoline

Following the procedure for the preparation of 2-[-4-(4-Pyridin-4-yl-2H-pyrazol-3-yl)-phenoxymethyl}-quinoline but substituting 1-[3-Fluoro-4-(quinolin-2-ylmethoxy)-phenyl]-2-pyridin-4-yl-ethanone provided the title compound. $^1$H NMR (400 MHz, CDCl$_3$) δ 8.47 (bs, 2H), 8.19 (d, J=8.7 Hz, 1H), 8.05 (d, J=8.3 Hz, 1 H), 7.71 (m, 4H), 7.54 (t, J=7.1 Hz, 1H), 7.18 (m, 3H), 7.07 (m, 2 H), 5.42 (s, 2 H); MS: ($M^+$H m/z=397.0).

EXAMPLE 33

2-[2-Fluoro-4-(1-methyl-4-pyridin-4-yl-1H-pyrazol-3-yl)-phenoxymethyl]-quinoline Following the procedure for the preparation of 2-[4-(1-Methyl-4-pyridin-4-yl-1H-pyrazol-3-yl)-phenoxymethyl]-quinoline but substituting 1-[3-Fluoro-4-(quinolin-2-ylmethoxy)-phenyl]-2-pyridin-4-yl-ethanone provided the title compound. $^1$H NMR (400 MHz, CDCl$_3$) δ 8.47 (d, J=6.2 Hz, 2H), 8.21 (d, J=8.3 Hz, 1H), 8.05 (d, J=8.7 Hz, 1 H), 7.83 (d, J=7.9 Hz, 2H), 7.72 (m, 2H), 7.55 (m, 2H), 7.16 (m, 2 H), 7.07 (m, 1H), 6.99 (m, 2H), 5.45 (s, 2 H), 3.95 (s, 3H); MS: ($M^+$H m/z=411.0).

Preparation 20

2,3-Difluoro-4-(quinolin-2-ylmethoxy)-benzoic acid quinolin-2-yl methyl ester Following the procedure for the preparation of 4-(Quinolin-2-ylmethoxy)-benzoic acid methyl ester but substituting 2,3-difluoro-4-hydroxy-benzoic acid provided the title compound. MS: (M+H m/z=457.1).

Preparation 21

2,3-Difluoro-4-(quinolin-2-ylmethoxy)-benzoic-acid

Following the procedure for the preparation of 4-(Quinolin-2-ylmethoxy)-benzoic acid but substituting 2,3-Difluoro-4-(quinolin-2-ylmethoxy)-benzoic acid quinolin-2-yl methyl ester provided the title compound. MS: (M+H m/z=316.1).

Preparation 22

2,3-Difluoro-N-methoxy-N-methyl-4-(quinolin-2-ylmethoxy)-benzamide

Following the procedure for the preparation of N-Methoxy-N-methyl-4-(quinolin-2-ylmethoxy)-benzamide but substituting 2,3-Difluoro-4-(quinolin-2-ylmethoxy)-benzoic acid provided the title compound. MS: (M+H m/z=359.1).

Preparation 23

1-[2,3-Difluoro-4-(quinolin-2-ylmethoxy)-phenyl]-2-pyridin-4-yl-ethanone

Following the procedure for the preparation of 2-pyridin-4-yl-1-[4-(quinolin-2-ylmethoxy)-phenyl]-ethanone but substituting 2,3-Difluoro-N-methoxy-N-methyl-4-(quinolin-2-ylmethoxy)-benzamide provided the title compound. MS: (M+H m/z=391.1).

EXAMPLE 34

2-[2,3-Difluoro-4-(1-methyl-4-pyridin-4-yl-1H-pyrazol-3-yl)-phenoxymethyl]-quinoline Following the procedure for the preparation of 2-[4-(1-Methyl-4-pyridin-4-yl-1H-pyrazol-3-yl)-phenoxymethyl]-quinoline but substituting 1-[2,3-Difluoro-4-(quinolin-2-ylmethoxy)-phenyl]-2-pyridin-4-yl-ethanone provided the title compound. $^1$H NMR (400 MHz, CDCl$_3$) δ 8.44 (bs, 2H), 8.22 (d, J=8.7 Hz, 1H), 8.06 (d, J=8.7 Hz, 1 H), 7.84 (d, J=7.9 Hz, 1H), 7.70 (m, 2H), 7.66 (s, 1H), 7.56 (t, J=7.9 Hz, 1H), 7.08 (m, 3H), 6.88 (m, 1H), 5.48 (s, 2H); MS: (M+H m/z=429.1).

Preparation 24

2-Fluoro-4-(quinolin-2-ylmethoxy)-benzoic acid quinolin-2-ylmethyl ester

Following the procedure for the preparation of 4-(Quinolin-2-ylmethoxy)-benzoic acid methyl ester but substituting 2-fluoro-4-hydroxy-benzoic acid provided the title compound. MS: (M+H m/z=439.0).

Preparation 25

2-Fluoro-4-(quinolin-2-ylmethoxy)-benzoic acid

Following the procedure for the preparation of 4-(Quinolin-2-ylmethoxy)-benzoic acid but substituting 2-Fluoro-4-(quinolin-2-ylmethoxy)-benzoic acid quinolin-2-yl methyl ester provided the title compound. MS: (M+H m/z=298.2).

Preparation 26

2-Fluoro-n-methoxy-N-methyl-4-(quinolin-2-ylmethoxy)-benzamide

Following the procedure for the preparation of N-Methoxy-N-methyl-4-(quinolin-2-ylmethoxy)-benzamide but substituting 2-Fluoro-4-(quinolin-2-ylmethoxy)-benzoic acid provided the title compound. MS: (M+H m/z =341.2).

Preparation 27

1-{2-Fluoro-4-(quinolin-2-ylmethoxy)-phenyl}-2-pyridin-4-yl-ethanone

Following the procedure for the preparation of 2-pyridin-4-yl-1-[4-(quinolin-2-ylmethoxy)-phenyl]-ethanone but substituting 2-Fluoro-n-methoxy-N-methyl-4-(quinolin-2-ylmethoxy)-benzamide provided the title compound. MS: (M+H m/z=373.0).

EXAMPLE 35

2-[3-Fluoro-4-(4-pyridin-4-yl-1H-pyrazol-3-yl)-phenoxymethyl]-quinoline

Following the procedure for the preparation of 2-[-4-(4-Pyridin-4-yl-2H-pyrazol-3-yl)-phenoxymethyl}-quinoline but substituting 1-{2-Fluoro-4-(quinolin-2-ylmethoxy)-phenyl}-2-pyridin-4-yl-ethanone provided the title compound. $^1$H NMR (400 MHz, CDCl$_3$) δ 8.47 (d, J=6.5 Hz, 2H), 8.22 (d, J=8.3 Hz, 1H), 8.08 (d, J=8.7 Hz, 1 H), 7.84 (s, 1H), 7.82 (m, 1H), 7.74 (m, 1H), 7.65 (d, J=8.7 Hz, 1 H), 7.55 (m, 1 H), 7.25 (m, 1 H), 7.18 (d, J=6.2 HZ, 2H), 6.85 (d, J=10.9, 2 H), 5.38 (s, 2 H); MS: (M+H m/z=397.2).

Preparation 28

4-(Quinolin-2-ylmethoxy)-benzaldehyde

Following the procedure for the preparation of 4-(Quinolin-2-ylmethoxy)-benzoic acid methyl ester but substituting 4-Hydroxy-benzaoldehyde provided the title compound. MS: (M+H m/z=264.2).

Preparation 29

1-Pyridin-4-yl-2-[4-(quinolin-2-ylmethoxy)-phenyl]-ethanone

To a solution of 4-pyridine carboxaldehyde (10.8 g) in 2-propanol (50 ml) was added aniline (9.3 g). After 15 min, the phenyl-pyridin-4-ylmethylene-amine product (68%) was filtered and used crude. To a solution of the imine in ethoanol (35 ml) was added diphenyl phosphite (13.1 ml) and stirred 1 h. Ethyl ether (200 mL) was added and the (Phenylamino-pyridin-4-yl-methyl-phosphonic acid diphenyl ester (5.06 g) was filtered. The phophonic ester (0.98 g) in THF (25 ml) was stirred at −40° C. under N$_2$. A solution of KOH/methanol (0.146 g/10%) was added followed by 4-(Quinolin-2-ylmethoxy)-benzaldehyde (0.62 g). The crude reation mixture was warmed to ambient temperature for 1 h and concentrated. The crude product was stirred in acetonitrile (1 mL)/1 ml conc. HCl for 1 h, quenched with sat'd sodium bicarbonate, extracted with chloroform, dried magnesium sulfate, filtered and concentrated. Purification via MPLC combiflash provided the title compound. MS: (M+H m/z=355.1).

EXAMPLE 36

2-[4-(5-Pyridin-4-yl-1H-pyrazol-4-yl)-phenoxymethyl]-quinoline

1-Pyridin-4-yl-2-[4-(quinolin-2-ylmethoxy)-phenyl]-ethanone (168 mg) was heated in diethoxymethyl-dimethyl amine (1 ml) at reflux for 2 hours. The reaction mixture was concentrated and dissolved in methanol (1 ml) and hydrazine hydrate (0.023 ml) was added and the reaction mixture was heated at 65° C. for 1 h. The reaction mixture was concentrated and purified by combiflash MPLC chromatography to provide the title compound (90%). $^1$H NMR (400 MHz, CDCl$_3$) δ 8.37 (bs, 2H), 8.18 (d, J=8.7 Hz, 1 H), 7.99 (d, J=8.7 Hz, 1H), 7.78 (d, J=8.3 Hz, 1 H), 7.66 (m, 2 H), 7.54 (s, 1 H), 7.48 (m, 1 H), 7.36 (m, 2 H), 7.11 (d, J=7.1 Hz, 2H), 6.94 (d, J=8.3 Hz, 2H), 5.29 (s, 2H); MS: (M+H m/z=379.2).

EXAMPLE 37

2-[4-(1-Methyl-5-pyridin-4-yl-1H-pyrazol-4-yl)-phenoxymethyl]-quinoline

Following the procedure for the preparation of 2-[4-(5-Pyridin-4-yl-1H-pyrazol-4-yl)-phenoxymethyl]-quinoline but substituting methyl hydrazine provided the title compound and 2-[4-(1-Methyl-3-pyridin-4-yl-1H-pyrazol4-yl)-phenoxymethyl]-quinoline. $^1$H NMR (400 MHz, CDCl$_3$) δ 8.66 (bs, 2 H), 8.17 (d, J=8.7 Hz, 1H), 8.05 (d, J=7.9 Hz, 1 H), 7.81 (d, J=8.3 Hz, 1H), 7.70 (m, 1 H), 7.63 (m, 2 H), 7.53 (t, J=7.1 Hz, 1 H), 7.21 (m, 2 H), 7.03 (d, J=9.1 Hz, 2H), 6.89 (d, J=8.7 Hz, 2H), 5.32 (s, 2H), 3.80 (s, 3H); MS: (M+H m/z=393.2).

EXAMPLE 38

2-[4-(1-Methyl-3-pyridin-4-yl-1H-pyrazol-4-yl)-phenoxymethyl]-quinoline

Following the procedure for the preparation of 2-[4-(5-Pyridin-4-yl-1H-pyrazol-4-yl)-phenoxymethyl]-quinoline but substituting methyl hydrazine provided the title compound and 2-[4-(1-Methyl-4-pyridin-4-yl-1H-pyrazol-4-yl)-phenoxymethyl]-quinoline. $^1$H NMR (400 MHz, CDCl$_3$) δ 8.49 (bs, 2 H), 8.20 (d, J=8.3 Hz, 1 H), 8.07 (d, J=8.3 Hz, 1 H), 7.83 (d, J=8.3 Hz, 1H), 7.74 (m, 2 H), 7.55 (t, J=7.1 Hz, 1 H), 7.42 (m, 2H), 7.38 (s, 1H), 7.17 (d, J=8.7 Hz, 2H) 7.00 (d, J=8.7Hz, 2H), 5.38 (s, 2H), 3.95 (s, 3H); MS: (M+H m/z=393.2).

EXAMPLE 39

2-Methyl-1-{4-pyridin-4-yl-3-[4-(quinolin-2-ylmethoxy)-phenyl]-pyrazol-1-yl}-propan-2-ol Following the procedure for the preparation of 2-[4-(1-Methyl-4-pyridin-4-yl-1H-pyrazol-3-yl)-phenoxymethyl]-quinoline but substituting 1-Hydrazino-2-methyl-propan-2-ol provided the title compound. $^1$H NMR (400 MHz, CDCl$_3$) δ 8.47 (d, J=6.2 Hz, 2 H), 8.19 (d, J=8.7 Hz, 1 H), 8.07 (d, J=8.7 Hz, 1 H), 7.82 (d, J=7.9 Hz, 1 H), 7.74 (t, J=8.3 Hz, 1 H), 7.68 (d, J=8.7 Hz, 1 H), 7.62 (s,1H), 7.55 (t, J=7.1 Hz, 1 H), 7.39 (d, J=8.7 Hz, 2H), 7.17 (m, 2H), 7.01 (d, J=8.7 Hz, 2H), 5.39 (s, 2H) 4.09 (s, 2H), 1.23 (s, 2H); MS: (M+H m/z=451.2).

EXAMPLE 40

2-Methyl-1-{4-pyridin-4-yl-5-[4-(quinolin-2-ylmethoxy)-phenyl]-pyrazol-1-yl}-propan-2-ol Following the procedure for the preparation of 2-[4-(1-Methyl-4-pyridin4-yl-1H-pyrazol-3-yl)-phenoxymethyl]-quinoline but substituting 1-Hydrazino-2-methyl-propan-2-ol provided the title compound. $^1$H NMR (400 MHz, CDCl$_3$) δ 8.37 (d, J=5.8 Hz, 2 H), 8.24 (d, J=8.3 Hz, 1 H), 8.09 (d, J=9.1 Hz, 1 H), 7.87 (s, 1H), 7.85 (d, J=7.9 Hz, 1H), 7.76 (m, 1 H), 7.72 (m, 1H), 7.17 (m, 4 H), 7.00 (d, J=6.2 Hz, 2H), 5.42 (s, 2H) 3.89 (s, 2H), 1.04 (s, 6H); MS: (M+H m/z=451.2).

EXAMPLE 41

(R)-1-{4-Pyridin-4-yl-3-[4-(quinolin-2-ylmethoxy)-phenyl]-pyrazol-1-yl}-propan-2-ol Following the procedure for the preparation of 2-[4-(1-Methyl-4-pyridin-4-yl-1H-pyrazol-3-yl)-phenoxymethyl]-quinoline but substituting (R)-1-Hydrazino-propan-2-ol provided the title compound. $^1$H NMR (400 MHz, CDCl$_3$) δ 8.42 (m, 2 H), 8.18 (d, J=8.3 Hz, 1 H), 8.06 (d, J=8.4 Hz, 1 H), 7.81 (d, J=8.3 Hz, 1H), 7.73 (m, 1H), 7.66 (d, J=8.7 Hz, 1H), 7.61 (s, 1 H), 7.54 (m, 1H), 7.36 (d, J=9.1 Hz, 2 H), 7.12 (m, 2H), 6.99 (d, J=8.7 Hz, 2H) 5.37 (s, 2H), 4.30 (m, 1H), 4.21 (dd, J=13.6, 2.5 Hz, 1H), 4.03 (dd, J=13.6, 7.9 Hz, 1H), 1.26 (d, J=6.2 Hz, 3H); MS: (M+H m/z=437.2).

EXAMPLE 42

(S)-1-{4-Pyridin-4-yl-3-[4-(quinolin-2-ylmethoxy)-phenyl]-pyrazol-1-yl}-propan-2-ol Following the procedure for the preparation of 2-[4-(1-Methyl-4-pyridin-4-yl-1H-pyrazol-3-yl)-phenoxymethyl]-quinoline but substituting (S)-1-Hydrazino-propan-2-ol provided the title compound. $^1$H NMR (400 MHz, CDCl$_3$) δ 8.42 (m, 2 H), 8.18 (d, J=8.3 Hz, 1 H), 8.06 (d, J=8.4 Hz, 1 H), 7.81 (d, J=8.3 Hz, 1H), 7.73 (m, 1H), 7.66 (d, J=8.7 Hz, 1H), 7.61 (s, 1 H), 7.54 (m, 1H), 7.36 (d, J=9.1 Hz, 2 H), 7.12 (m, 2H), 6.99 (d, J=8.7 Hz, 2H) 5.37 (s, 2H), 4.30 (m, 1H), 4.21 (dd, J=13.6, 2.5 Hz, 1H), 4.03 (dd, J=13.6, 7.9 Hz, 1H), 1.26 (d, J=6.2 Hz, 3H), MS: (M+H m/z=437.2).

EXAMPLE 43

2-[4-(1-Isopropyl-4-pyridin-4-yl-1H-pyrazol-3-yl)-phenoxymethyl]-quinoline

To a solution of 2-[4-(4-Pyridin-4-yl-2H-pyrazol-3-yl)-phenoxymethyl]-quinoline (0.075 g) in dimethyl formamide (2 ml) was added cesium carbonate (0.098 g) and 2-iodo propane (0.030 ml) and the reaction mixture heated at 60° C. for 72 h. The reaction mixture was poured into water and extracted with methylene chloride, dried magnesium sulfate, filtered and concentrated. Purification via Prep TLC eluting with 2% methanol/1% saturated ammonium hydroxide/67% ethyl acetate/30% hexane provided the title compound (60 mg). $^1$H NMR (400 MHz, CDCl$_3$) δ 8.43 (d, J=6.2 Hz, 2 H), 8.16 (d, J=8.7 Hz, 1 H), 8.05 (d, J=9.1 Hz, 1 H), 7.80 (d, J=8.3 Hz, 1H), 7.70 (m, 1H), 7.65 (d, J=8.7 Hz, 1 H), 7.59 (s, 1H), 7.53 (t, J=7.1 Hz, 1 H), 7.38 (d, J=9.1 Hz, 2H), 7.15 (d, J=8.7 Hz, 2H), 6.99 (d, J=8.7 Hz, 2H), 5.38 (s, 2H) 4.51 (m, 1H), 1.54 (d, J=6.6 Hz, 6H); MS: (M+H m/z=421.2).

EXAMPLE 44

2-[4-(1-Isobutyl-4-pyridin-4-yl-1H-pyrazol-3-yl)-phenoxymethyl]-quinoline

Following the procedure for the preparation of 2-[4-(1-Isopropyl-4-pyridin4-yl-1H-pyrazol-3-yl)-phenoxymethyl]-quinoline but substituting 1-Iodo-2-methyl-propane provided the title compound. $^1$H NMR (400 MHz, CDCl$_3$) δ 8.44 (m, 2H), 8.18 (d, J=8.7 Hz, 1H), 8.06 (d, J=8.3 Hz, 1 H), 7.83 (d, J=6.6 Hz, 1 H), 7.73 (t, J=6.6 Hz, 1H), 7.54 (s,1H), 7.52 (m, 1H), 7.38 (d, J=9.1 Hz, 2 H), 7.15 (m, 2H), 7.00 (d, J=8.7 Hz, 2 H), 5.38 (s, 2H) 3.93 (d, J=7.5 Hz, 2 H), 4.29 (m, 1H), 0.95 (d, J=6.6 Hz, 6H); MS: (M$^+$H m/z=435.2).

EXAMPLE 45

2-[4-(1-Methyl-4-pyridin-4-yl-1H-pyrazol-3-yl)-phenoxymethyl]-[1.8]Naphthyridine To a solution of 4-(1-methyl-4-pyridin-4-yl-1H-pyrazol-3-yl)-phenol (72 mg) in dioxane 1.5 ml, was added triphenyl phosphine (121 mg), [1,8]Naphthyridin-2-yl-methanol (69 mg) and di-t-butyl-diazacarboxalate (106 mg) and the reaction mixture heated at 60° C. for 24 h. The reaction mixture was poured into 1 N NaOH, extracted with methylene chloride, dried magnesium sulfate and concentrated. Purification via Prep TLC eluting with 15% methanol/70%ethyl acetate/15% hexanes provided the title compound (9.8 mg). $^1$H NMR (400 MHz, CDCl$_3$) δ 9.13 (dd, J=4.2, 1.7 Hz, 1H), 8.45 (d, J=5.8 Hz, 2H), 8.23 (d, J=8.3 Hz, 1H), 7.21 (dd, J=8.5, 2.1 Hz, 1 H), 7.79 (d, J=8.7 Hz, 1H), 7.57 (s, 1H), 7.52 (m, 1H), 7.37(d, J=9.1 Hz, 2 H), 7.16 (d, J=6.2 Hz, 2H), 7.01 (d, J=8.7 Hz, 2 H), 5.47 (s, 2H), 3.94 (s, 3 H); MS: (M$^+$H m/z=394.0).

Preparation 30

4-(2-Quinolin-2-yl-ethyl)-benzoic acid methyl ester

To a solution of 4-[Triphenyl-phophanyl)-methyl]-benzoic acid methyl ester (1.87 g) in THF (16 ml) under N$_2$ atmosphere at 0° C. was added sodium hydride (165 mg (60%)). After 30 min, quinoline-2-carbaldehyde (0.50 g) was added and the reaction stirred at ambient temperature for 2 h. The reaction mixture was quenched with brine, extracted with chloroform, dried magnesium sulfate, filtered and concentrated to provide the crude alkene. The crude product was placed on a parr shaker in ethanol (15 ml) with palladium hydroxide (200 mg) as the catalyst under 10 PSI of H$_2$. After 40 min, the reaction mixture was filtered through celite and concentrated. Biotage MPLC chromatography eluting with 10-20% ethyl acetate/hexane provided the title compound. MS: (M$^+$H m/z=292.1).

Preparation 31

4-(2-Quinolin-2-yl-ethyl)-benzoic acid

To a solution of 4-(2-Quinolin-2-yl-ethyl)-benzoic acid methyl ester (680 mg) in THF (11 ml)/methanol (3 ml) was added 1N sodium hydroxide solution (4.67 ml). The reaction mixture stirred for 4 h. and the pH adjusted to 3. The white solid was filtered to provide the title compound (550 mg, 86%). MS: (M$^+$H m/z=278.1).

Preparation 32

N-Methoxy-N-methyl-4-(2-quinolin-2-yl-ethyl)-benzamide

To a solution of 4-(2-Quinolin-2-yl-ethyl)-benzoic acid (530 mg) in dioxane 5 ml/acetonitrile 5 ml was added triethylamine (0.60 ml) and O,N-Dimethyl-hydroxylamine hydrogen chloride (240 mg). After 72 h, the reaction mixture was poured into 1N sodium hydroxide solution and extracted with chloroform, dried magnesium sulfate, filtered and concentrated. Biotage MPLC chromatography eluting with 20-50% ethyl acetate provided the title compound (516 mg, 88%). MS: (M$^+$H m/z=321.1).

Preparation 33

2-Pyridin-4-yl-1-[4-(2-quinolin-2-yl-ethyl)-phenyl]-ethanone

Following the procedure for the preparation of 2-pyridin-4-yl-1-[4-(quinolin-2-ylmethoxy)-phenyl]-ethanone but substituting N-Methoxy-N-methyl-4-(2-quinolin-2-yl-ethyl)-benzamide provided the title compound. MS: (M$^+$H m/z=353.1).

EXAMPLE 46

2-{2-[4-(4-Pyridin-4-yl-2H-pyrazol-3-yl)-phenyl]-ethyl}-quinoline

To 2-Pyridin-4-yl-1-[4-(2-quinolin-2-yl-ethyl)-phenyl]-ethanone (53 mg) was added 3 ml of Diethoxymethyl-dimethyl-amine and the reaction mixture heated at 100° C. After 3 h, the reaction mixture as concentrated and methanol (3 ml) and hydrazine (0.02 ml) was added. The reaction mixture was heated at 60° C. for 3 h and concentrated. Biotage MPLC purification eluting with 1-3% methanol/0.5% saturated ammonium hydroxide in chloroform provided the title compound. $^1$H NMR (400 MHz, CDCl$_3$) δ 8.47 (d, J=6.2 Hz, 2 H), 8.05 (d, J=8.3 Hz, 2 H), 7.80 (s, 1H), 7.78 (d, J=8.3 Hz, 2 H), 7.70 (t, J=7.1 Hz, 1H), 7.51 (t, J=7.1 Hz, 1 H), 7.32 (d, J=8.3 Hz, 2 H), 7.24 (m, 3H), 7.19 (d, J=6.2 Hz, 2H), 3.31 (m, 2H), 3.22 (m, 2H), MS: (M$^+$H m/z=377.1).

EXAMPLE 47

2-(2-[4-(1-Methyl-4-pyridin-4-yl-1H-pyrazol-3-yl)-phenyl]-ethyl]-quinoline

Following the procedure for the preparation of 2-{2-[4-(4-Pyridin-4-yl-2H-pyrazol-3-yl)-phenyl]-ethyl}-quinoline but substituting methyl hydrazine provided the title compound. $^1$H NMR (400 MHz, CDCl$_3$) δ 8.45 (d, J=6.2 Hz, 2 H), 8.06 (t, J=10.4 Hz, 2 H), 7.77 (d, J=7.1 Hz, 1 H), 7.70 (t, J=8.3 Hz, 1 H), 7.57 (s, 1H), 7.50 (t, J=9.1 Hz, 1 H), 7.35 (d, J=8.3 Hz, 2H), 7.24 (m, 3H), 7.20 (d, J=5.0 Hz, 2H), 3.97 (s, 3H), 3.31 (m, 2H), 3.18 (m, 2H); MS: (M$^{+H}$ m/z=391.0).

Preparation 34

2-(2-Chloro-pyridin-4-yl)-1-[4-(quinolin-2-yl-methoxy)-phenyl]-ethanone

Following the procedure for the preparation of 2-pyridin-4-yl-1-[4-(quinolin-2-ylmethoxy)-phenyl]-ethanone but substituting 2-chloro-4-methyl pyridine provided the title compound. MS: (M$^+$H m/z=389.0).

EXAMPLE 48

2-{4-[4-(2-Chloro-pyridin-4-yl)-1H-pyrazol-3-yl]-phenoxymethyl}-quinoline

Following the procedure for the preparation of 2-{2-[4-(4-Pyridin4-yl-2H-pyrazol-3-yl)-phenyl]-ethyl}-quinoline but substituting 2-(2-Chloro-pyridin-4-yl)-1-[4-(quinolin-2-yl-methoxy)-phenyl]-ethanone provided the title compound. $^1$H NMR (400 MHz, CDCl$_3$) δ 8.23 (m, 2 H), 8.08 (d, J=8.7 Hz, 1 H), 7.83 (d, J=8.3 Hz, 1 H), 7.80 (s, 1H), 7.75 (t, J=7.1 Hz, 1 H), 7.67 (d, J=8.3 Hz, 1H), 7.57 (t, J=7.1 Hz, 1 H), 7.33 (d, J=9.1 Hz, 2H), 7.05 (m, 4H), 5.40 (s, 2H); MS: (M$^+$H m/z=413.1).

EXAMPLE 49

2-{4-[4-(2-Chloro-pyridin-4-yl)-1-methyl-1H-pyrazol-3-yl]-phenoxymethyl}-quinoline Following the procedure for the preparation of 2-2-[4-(4-Pyridin-4-yl-2H-pyrazol-3-yl)-phenyl]-ethyl}-quinoline but substituting methyl hydrazine and 2-(2-Chloro-pyridin-4-yl)-1-[4-(quinolin-2-ylmethoxy)-phenyl]-ethanone provided the title compound. $^1$H NMR (400 MHz, CDCl$_3$) δ 8.19 (m, 2 H), 8.07 (d, J=8.3 Hz, 1 H), 7.83 (d, J=8.3 Hz, 1 H), 7.74 (t, J=8.3 Hz, 1H), 7.67 (d, J=8.3 Hz, 1 H), 7.58 (s, 1H), 7.55 (t, J=8.3 Hz, 1 H), 7.36 (d, J=8.7 Hz, 2H), 7.20 (s, 1H), 7.03 (m, 3H), 5.40 (s, 2H) 3.95 (s, 3H); MS: (M$^+$H m/z=427.0).

EXAMPLE 50

2-{4-[1-Methyl-4-(2-methyl-pyridin-4-yl)-1H-pyrazol-3-yl]-phenoxymethyl}-quinoline To a solution of 2-{4-[4-(2-Chloro-pyridin-4-yl)-1-methyl-1H-pyrazol-3-yl]-phenoxymethyl}-quinoline (100 mg) in dioxane (1.2 ml) was added methyl boroxine (0.066 ml), palladium tetrakis (41 mg) and 2N sodium carbonate solution (0.234 ml). The reaction mixture was heated at 100° C. for 8 h, poured into 1 N NaOH, extracted with chloroform, dried magnesium sulfate, filtered and concentrated. Prep TLC run with 3% methanol/0.5% saturated ammonium hydroxide/80% ethyl acetate in hexanes provided the free base material. The produce was stirred in ethyl acetate and 2 eq. of succinic acid was added to give a white precipitate which was filtered to provide the title compound as a white solid succinate salt (20 mg). $^1$H NMR (400 MHz, DMSO) δ 8.40 (d, J=8.3 Hz, 2 H), 8.25 (d, J=5.0 Hz, 2 H), 8.07 (s, 1H), 8.00 (t, J=7.9 Hz, 2 H), 7.77 (t, J=6.6 Hz, 1 H), 7.67 (d, J=8.7 Hz, 2H), 7.60 (t, J=6.6 Hz, 1 H), 7.29 (d, J=9.1 Hz, 2H), 7.03 (m, 3 H), 6.92 (m, 1H), 5.35 (s, 2H), 3.85 (s, 3H), 2.37 (s, 4H) 2.31 (s, 3H); MS: (M$^+$H m/z=407.0).

EXAMPLE 51

Dimethyl-(4-{1-methyl-3-[4-(quinolin-2-yl-methoxy)-phenyl]-1H-pyrazol-4-yl}-pyridin-2-yl)-amine To a solution of 2-{4-[4-(2-Chloro-pyridin-4-yl)-1-methyl-1H-pyrazol-3-yl]-phenoxymethyl}-quinoline (100 mg) in dimethyl formamide (1 ml) was added diethanolamine (0.035 ml) and the reaction mixture heated at 130° C. for 72 h. The reaction mixture was poured into water and extracted with ethyl ether, dried magnesium sulfate, filtered and concentrated. Prep TLC eluting with 60% ethyl acetate/hexane provided the title compound as a Free base. The product was stirred in ethyl acetate and 1 eq. of succinic acid was added. After 18 h, the white precipitate was filtered to provide the succinate salt (24 mg). $^1$H NMR (400 MHz, DMSO) δ 8.40 (d, J=8.3 Hz, 1 H), 8.03 (s, 1 H), 7.98 (m, 2 H), 7.90 (d, J=5.4 Hz, 1 H), 7.77 (m, 1H), 7.65 (d, J=8.3 Hz, 1 H), 7.59 (m, 1 H), 7.31 (d, J=6.6 Hz, 2H), 7.04 (d, J=9.1 Hz, 2 H), 6.37 (m, 2 H), 5.35 (s, 2H), 3.84 (s, 3H), 2.80 (s, 6H) 2.37 (s, 4H); MS: M$^+$H m/z=436.0).

Preparation 35

3-Dimethylamino-1-pyridin-4-yl-propenone

To 1-Pyridin-4-yl-ethanone(1.62 g) was added N,N-dimethylformamide diethylacetal (10 ml) and the reaction mixture heated at 120° C. for 2 h and concentrated to provide the title compound. MS: (M$^+$H m/z=177.0).

Preparation 36

4-[2-(4-Benzyloxy-phenyl-2H-pyrazol-3-yl]-pyridine

To a solution of 3-Dimethylamino-1-pyridin-4-yl-propenone (590 mg) in methanol (10 ml) was added acetic acid (0.5 ml) and (4-Benzyloxy-phenyl)-hydrazine hydrogen chloride (836 mg) and the reaction mixture heated to 60° C. for 6 h. The reaction mixture was poured into saturated sodium bicarbonate, extracted with ethyl acetate, dried magnesium sulfate, filtered and concentrated. Purification via combiflash MPLC provided the title compound (795 mg). MS: (M$^+$H m/z=328.1).

Preparation 37

4-(5-Pyridin-4-yl-pyrazol-1-yl)-phenol

To a solution of 4-[2-(4-Benzyloxy-phenyl-2H-pyrazol-3-yl]-pyridine (610 mg) in ethyl acetate (15 ml)/ethanol (15 ml) was added palladium hydroxide (20%, 343 mg). The reaction mixture was placed on a parr shaker under 45 psi of H$_2$ gas for 18 h. The reaction mixture was filtered through celite and concentrated. Purification via chromatotron (2 mm silica, 5% methanol/chloroform) provided the title compound (259 mg). MS: (M$^+$H m/z=238.1).

EXAMPLE 52

2-[4-(5-Pyridin-4-yl-pyrazol-1-yl)-phenoxymethyl]-quinoline

To a solution of 4-(5-Pyridin-4-yl-pyrazol-1-yl)-phenol (82 mg) in acetone was added potassium carbonate (153 mg) and 2-Chloromethyl-quinoline (95 mg) and the reaction mixture heated at 60° C. for 18 h. The reaction mixture was poured into brine and extracted with ethyl acetate, dried magnesium sulfate, filtered and concentrated. Purification via combiflash MPLC provided the title compound (91 mg). $^1$H NMR (400 MHz, CDCl$_3$) δ 8.51 (m, 2 H), 8.20 (d, J=8.7 Hz, 1 H), 8.06 (d, J=8.7 Hz, 1 H), 7.83 (d, J=7.1 Hz, 1H), 7.74 (m, 2H), 7.65 (d, J=8.7 Hz, 1 H), 7.57 (m, 1H), 7.20 (d, J=8.7 Hz, 2 H), 7.09 (d, J=5.8 Hz, 2H), 7.02 (d, J=9.1 Hz, 2H), 6.60 (d, J=1.7 Hz, 1H), 5.39 (s, 2H); MS: (M$^+$H m/z=379.0).

EXAMPLE 53

2-[4-(3-Methyl-5-pyridin-4-yl-pyrazol-1-yl)-phenoxymethyl]-quinoline

Following the procedure for the preparation of 2-[4-(5-Pyridin-4-yl-pyrazol-1-yl)-phenoxymethyl]-quinoline but substituting (1,1-Dimethoxy-ethyl)-dimethyl-amine provided the title compound. $^1$H NMR (400 MHz, CDCl$_3$) δ 8.49 (d, J=6.2 Hz, 2 H), 8.20 (d, J=8.3 Hz, 1 H), 8.06 (d, J=8.7 Hz, 1 H), 7.83 (d, J=8.3 Hz,1H), 7.74 (m,1H), 7.64 (d, J=8.3 Hz, 1 H), 7.54 (m, 1H), 7.18 (d, J=8.7 Hz, 2 H), 7.07 (d, J=6.2 Hz, 2H), 7.00 (d, J=9.1 Hz, 2H), 6.40 (s, 1H), 5.38 (s, 2H), 2,35 (s, 3H); MS: (M$^+$H m/z=393.4).

Preparation 38

3-Chloro-4-(quinolin-2-ylmethoxy)-benzoic acid methyl ester

Following the procedure for the preparation of 4-(Quinolin-2-ylmethoxy)-benzoic acid methyl ester but substituting 3-Chloro-4-hydroxy-benzoic acid methyl ester provided the title compound. MS: (M$^+$H m/z=328.0).

Preparation 39

3-Chloro-4-(quinolin-2-ylmethoxy)-benzoic acid

Following the procedure for the preparation of 4-(Quinolin-2-ylmethoxy)-benzoic acid but substituting 3-Chloro-4-(quinolin-2-ylmethoxy)-benzoic acid methyl ester provided the title compound. (M$^+$H m/z=314.0).

Preparation 40

3-Chloro-N-methoxy-N-methyl4-(quinolin-2-ylmethoxy)-benzamide

Following the procedure for the preparation of N-Methoxy-N-methyl-4-(2-quinolin-2-yl-ethyl)-benzamide but substituting 3-Chloro4-(quinolin-2-ylmethoxy)-benzoic acid provided the title compound. (M$^+$H m/z=356.9).

Preparation 41

1-[3-Chloro-4-(quinolin-2-ylmethoxy)-phenyl]-2-pyridin-4-yl-ethanone

Following the procedure for the preparation of 2-pyridin-4-yl-1-[4-(quinolin-2-ylmethoxy)-phenyl]-ethanone but substituting 3-Chloro-N-methoxy-N-methyl-4-(quinolin-2-ylmethoxy)-benzamide provided the title compound. (M$^+$H m/z=389.0).

EXAMPLE 54

2-[2-Chloro4-(4-pyridin4-yl-1H-pyrazol-3-yl)-phenoxymethyl]-quinoline

Following the procedure for the preparation of 2-{2-[4-(4-Pyridin-4-yl-2H-pyrazol-3-yl)-phenyl]-ethyl}-quinoline but substituting 1-[3-Chloro-4-(quinolin-2-ylmethoxy)-phenyl]-2-pyridin-4-yl-ethanone provided the title compound. $^1$H NMR (400 MHz, CD$_3$OD) δ 8.37 (m, 4 H), 8.02 (d, J=8.7 Hz, 2 H), 7.93 (d, J=8.3 Hz, 2H), 7.78 (m, 2 H), 7.61 (t, J=7.1 Hz, 1 H), 7.31 (m, 2H), 7.21 (m, 1 H), 5.44 (s, 2H); MS: (M$^+$H m/z=413.0).

EXAMPLE 55

2-[2-Chloro-4-(1-methyl-4-pyridin-4-yl-1H-pyrazol-3-yl)-phenoxymethyl]-quinoline Following the procedure for the preparation of 2-{2-[4-(4-Pyridin-4-yl-2H-pyrazol-3-yl)-phenyl]-ethyl}-quinoline but substituting methyl hydrazine and 1-[3-Chloro-4-(quinolin-2-ylmethoxy)-phenyl]-2-pyridin-4-yl-ethanone provided the title compound. $^1$H NMR (400 MHz, CDCl$_3$) δ 8.47 (d, J=6.2 Hz, 2 H), 8.21 (d, J=8.3 Hz, 1 H), 8.04 (d, J=7.5 Hz, 1H), 7.83 (d, J=8.3 Hz, 1 H), 7.78 (d, J=8.7 Hz, 1 H), 7.72 (m, 1H), 7.56 (m, 3 H), 7.21 (m, 1H), 7.14 (d, J=6.2 Hz, 2 H), 6.97 (d, J=8.7 Hz, 1 H), 5.46 (s, 2H), 3.95 (s, 3H); MS: (M$^+$H m/z=427.1).

Preparation 42

4-(4-Pyridin-4-yl-4H-[1,2,4]triazol-3-yl)-phenol

To a solution of 4-Methoxy-N-pyridin-4-yl-benzamide (75 mg) in POCl$_3$ (3 ml) was added PCl$_5$ (68 mg) and the reaction mixture heated at reflux for 5 h. The reaction mixture was concentrated and dissolved in dimethyl formamide (2 ml) and Formic acid hydrazide (5 eq, 100 mg) was added and stirred for 2 h. The reaction mixture was concentrated and diluted with isopropanol (3 mL) and 0.25 ml of conc. HCl was added. The reaction mixture stirred for 18 h, quenched with 1 NaOH, extracted with dichloromethane, dried magenesium sulfate and concentrated. The crude product dissolved in methylene chloride (2 mL) and boron tribromide (0.63 mL 1.0M hexanes) was added at 0° C. The reaction mixture was warmed to ambient temperature and stirred for 18 h. The reaction mixture was quenched with 1 N NaOH and pH adjusted to 9, extracted with dichloromethane, dried magnesium sulfate, filtered and concentrated. Purification via Biotage MPLC chromatography eluting with 0-20% methanol/methylene chlroride provided the title compound (32 mg, 55%). MS: (M$^+$H m/z=239.2).

EXAMPLE 56

2-[4-(4-Pyridin-4-yl-4H-[1,2,4]triazol-3-yl)-phenoxymethyl]-quinoline

To a solution of 4-(4-Pyridin-4-yl-4H-[1,2,4]triazol-3-yl)-phenol (44 mg) in dimethyl formamide (1 ml) in a 7 ml Teflon capped vial was added cesium carbonate (185 mg) and 2-Chloromethyl-quinoline (37 mg) and the reaction mixture heated on a shaker plate at 60° C. for 18 h. The reaction mixture was poured into water and extracted with methylene chloride, dried magnesium sulfate, filtered and concentrated to provide the title compound (45 mg). $^1$H NMR (400 MHz, CDCl$_3$) δ 8.87 (s, 1H), 8.65 (d, J=6.0 Hz, 2 H), 8.37 (d, J=8.3 Hz, 1 H), 8.03 (d, J=8.7 Hz, 1H), 7.94 (d, J=7.9 Hz, 1H), 7.78 (m, 1 H), 7.70 (d, J=8.3 Hz, 1 H), 7.61 (t, J=5.8 Hz, 1 H), 7.40 (m, 4H), 7.14 (d, J=9.1 Hz, 2 H), 5.38 (s, 2H); MS: (M$^+$H m/z=380.2).

Preparation 43

[4-(Quinolin-2-ylmethoxy)-phenyl]-hydrazine

To a suspension of 4-(Quinolin-2-ylmethoxy)-phenylamine (1.73 g) in 30 mL of concentrated HCl at 0° C. was added sodium nitrite (531 mg). After 3 h, tin chlrodie (3.95 g) was dissolved in 20 mL of concentrated HCl and added slowly dropwise and the reaction mixture stirred at ambient temperature for 18 h. The reaction mixture was filtered and the solid dried to provide the title compound as the HCL salt (3.94 g). MS: (M+H m/z=266.3).

EXAMPLE 57

2-[4-(5-Pyridin4-yl-[1,2,4]triazol-1-yl)-phenoxymethyl]-quinoline

Isonicatinamide (4.15 g) was heated in 35 ml of N,N-Dimethylformamide diethyl acetal at reflux for 3 h. The reaction mixture was cooled to ambient temperature and concentrated to give 5.02 g of N-Dimethylaminomethylene-isonicotinamide. To a solution of [4-(Quinolin-2-ylmethoxy)-phenyl]-hydrazine (3.16 g) in methanol (30 mL) and acetic acid (2.5 mL) was added N-Dimethylaminomethylene-isonicotinamide (1.10 g) and the reaction mixture heated at reflux for 72 h. The reaction mixture was concentrated onto silica gel and purified by flash chromatography to provided the title compound (514 mg). $^1$H NMR (400 MHz, CDCl$_3$) δ 8.60 (d, J=5.8 Hz, 2 H), 8.22 (d, J=8.7 Hz, 1 H), 8.10 (s, 1H), 8.07 (d, J=8.7 Hz, 1H), 7.85 (d, J=7.1 Hz, 1H), 7.76 (m, 1 H), 7.66 (d, J=8.3 Hz, 1 H), 7.56 (m, 1 H), 7.56 (m, 1H), 7.38 (d, J=6.2 Hz, 2 H), 7.26 (d, J=8.7Hz, 2H), 7.11 (d, J=9.1 Hz, 2H), 5.42 (s, 2H); MS: (M+H m/z=380.3).

Preparation 44

[4-(Quinolin-2-ylmethoxy)-phenyl]-hydrazine

Following the procedure for the preparation of (4-(Quinolin-2-ylmethoxy)-phenyl]-hydrazine but substituting 4-(Quinolin-2-ylmethoxy)-phenylamine provided the title compound. MS: (M+H m/z=266.2).

EXAMPLE 58

2-[4-(3-Methyl-5-pyridin-4-yl-[1,2,4]triazol-1-yl)-phenoxymethyl]-quinoline

Following the procedure for the preparation of 2-[4-(5-Pyridin-4-yl-[1,2,4]triazol-1-yl)-phenoxymethyl]-quinoline but substituting N,N-dimethylacetamide dimethyl acetal provided the title compound. $^1$H NMR (400 MHz, CDCl$_3$) δ 8.58 (d, J=6.2 Hz, 2 H), 8.22 (d, J=8.3 Hz, 1 H), 8.08 (d, J=8.3 Hz, 1H), 7.84 (d, J=7.7 Hz, 1H), 7.74 (m, 1 H), 7.65 (d, J=8.3 Hz, 1 H), 7.56 (m, 1 H), 7.36 (d, J=6.2 Hz, 2 H), 7.25 (d, J=9.1 Hz, 2H), 7.09 (d, J=8.7 Hz, 2H), 5.41 (s, 2H), 2.48 (s, 3H); MS: (M+H m/z=394.4).

Preparation 45

4-(Quinolin-2-ylmethoxy)-benzamide

To a solution of 2-Chloromethyl-quinoline (1.57 g) and 4-Hydroxy-benzamide (995 mg) in dimethyl formamide (20 mL) was added cesium carbonate (7.3 g) and the reaction mixture heated at 80° C. for 18 h. The reaction mixture was poured into water and extracted with chloroform, dried magnesium sulfate, filtered and concentrated to provided the title compound (909 mg). MS: (M+H -m/z=279.3).

EXAMPLE 59

2-[4-(2-Pyridin-4-yl-2H-[1,2,4]triazol-3-yl)-phenoxymethyl]-quinoline

Following the procedure for the preparation of 2-[4-(5-Pyridin-4-yl-[1,2,4]triazol-1-yl)-phenoxymethyl]-quinoline but substituting 4-(Quinolin-2-ylmethoxy)-benzamide and Pyridin-4-yl-hydrazine provided the title compound. $^1$H NMR (400 MHz, CDCl$_3$) δ 8.65 (d, J=6.2 Hz, 2 H), 8.21 (d, J=8.3 Hz, 1 H), 8.08 (s, 1H), 8.07 (d, J=7.9 Hz, 1H), 7.84 (d, J=8.3 Hz, 1H), 7.73 (m, 1 H), 7.65 (d, J=8.7 Hz, 1 H), 7.55 (m, 1 H), 7.43 (d, J=9.1 Hz, 2H), 7.32 (d, J=6.2 Hz, 2 H), 7.05 (d, J=8.7Hz, 2H), 5.40 (s, 2H); MS: (M+H m/z=380.2).

EXAMPLE 60

2-[4-(5-Methyl-2-pyridin-4-yl-2H-[1,2,4]triazol-3-yl)-phenoxymethyl]-quinoline

Following the procedure for the preparation of 2-[4-(5-Pyridin-4-yl-[1,2,4]triazol-1-yl)-phenoxymethyl]-quinoline but substituting 4-(Quinolin-2-ylmethoxy)-benzamide, Pyridin4-yl-hydrazine and N,N-dimethylacetamide dimethyl acetal provided the title compound. $^1$H NMR (400 MHz, CDCl$_3$) δ 8.61 (d, J=6.2 Hz, 2 H), 8.21 (d, J=8.7 Hz, 1 H), 8.07 (d, J=7.9 Hz, 1H, 7.83 (d, J=8.3 Hz, 1H), 7.75 (m, 1 H), 7.64 (d, J=8.3 Hz, 1 H), 7.55 (m, 1 H), 7.56 (m, 1H), 7.41 (d, J=9.1 Hz, 2 H), 7.29 (d, J=6.2 Hz, 2H), 7.05 (d, J=8.7 Hz, 2H), 5.40 (s, 2H), 2.47 (s, 3H); MS: (M+H m/z=394.3).

Preparation 46

4-[3-(4-Benzyloxy-phenyl)-1H-pyrazol-4-yl]-pyridine

To a solution of 1-(4-Benzyloxy-phenyl)-2-pyridin-4-yl-ethanone (1.58 g) was added toluene (26 ml) and 1.6 g of Diethoxymethyl-dimethyl-amine and the reaction mixture heated at reflux for 1 h. The reaction mixture was concentrated, dissolved in methanol (26 ml) and hydrazine (0.64 g) and the reaction mixture was heated at reflux for 1 h. The reaction mixture was concentrated and purified via biotage MPLC eluting with 5% methanol/chloroform/0.5% ammonium hydroxide to provided the title compound (0.89 g). MS: (M+H m/z=328.1).

Preparation 47

4-[3-(4-Benzyloxy-phenyl)-1-(2,2,2-trifluoro-ethyl)-1H-pyrazol4-yl]-pyridine

To a solution of 4-[3-(4-Benzyloxy-phenyl)-1H-pyrazol-4-yl]-pyridine (0.42 g) in dimethyl formamide (7 ml) was added cesium carbonate (0.65 g) and 1,1,1-Trifluoro-2-iodo-ethane (0.29 ml). The reaction mixture was heated at 60° C. for 24 h, poured into water and extracted 3× with dichloromethane. Purification via biotage MPLC chromatography, eluting with 5% methanol/0.5% ammonium hydroxide/70% ethyl acetate/hexane provided the title compound. MS: (M+H m/z=410.0).

Preparation 48

4-[4-Pyridin-4-yl-1-(2,2,2-trifluoro-ethyl)-1H-pyrazol-3-yl]-phenol

Following the procedure for the preparation of 4-(1-Methyl4-pyridin4-yl-1H-pyrazol-3-yl)-phenol but substituting 4-[3-(4-Benzyloxy-phenyl)-1-(2,2,2-trifluoro-ethyl)-1H-pyrazol-4-yl]-pyridine provided the title compound. MS: (M+H m/z=320.1)

EXAMPLE 61

2-{4-[4-Pyridin-4-yl-1-(2,2,2-trifluoro-ethyl)-1H-pyrazol-3-yl]-phenoxymethyl}-quinoxaline To a solution of 4-[4-Pyridin4-yl-1-(2,2,2-trifluoro-ethyl)-1H-pyrazol-3-yl]-phenol (79 mg) and Quinoxalin-2-yl-methanol (50 mg) in dioxane (2 ml) was added triphenylphosphine (105 mg) and di-t-butyldiazacarboxalate (92 mg) and the reaction mixture heated at 60° C. After 18, the reaction mixture was poured into 1N NaOH, extracted with methylene chloride, dried magnesium sulfate, filtered and concentrated. Purification with MPLC biotage eluting with 2% methanol/0.5% ammonium hydroxide/60% ethyl acetate/hexanes provided the title compound (54 mg). $^1$H NMR (400 MHz, CDCl$_3$) δ 9.09 (s, 1 H), 8.52 (m, 2H), 8.13 (m, 1H), 8.10 (m, 1H), 7.79 (m, 2 H), 7.73 (s, 1 H), 7.40 (d, J=8.7, Hz, 2 H), 7.24 (m, 2H), 7.04 (d, J=8.7 Hz, 2 H), 5.32 (s, 2H), 4.79 (q, J=8.3 Hz, 2 H); MS: (M$^+$H m/z=462.1).

EXAMPLE 62

8-Methoxy-2-[4-(1-methyl-4-pyridin-4-yl-1H-pyrazol-3-yl)-phenoxymethyl]-quinoline Following the procedure for the preparation of 2-{4-[4-Pyridin4-yl-1-(2,2,2-trifluoro-ethyl)-1H-pyrazol-3-yl]-phenoxymethyl}-quinoxaline but substituting 4-(1-Methyl4-pyridin4-yl-1H-pyrazol-3-yl)-phenol and (8-Methoxy-quinolin-2-yl)-methanol provided the title compound. $^1$H NMR (400 MHz, CDCl$_3$) δ 8.45 (d, J=6.2 Hz, 2 H), 8.15 (d, J=8.7 Hz, 1H), 7.73 (d, J=8.3 Hz,1H), 7.55 (s, 1H), 7.44 (m, 1 H), 7.37 (m, 3 H), 7.15 (d, J=5.8, Hz, 2 H), 7.07 (d, J=7.5 Hz, 1H), 6.99 (d, J=8.7 Hz, 2 H), 5.46 (s, 2H), 4.08 (s, 3 H), 3.94 (s, 3H); MS: (M$^+$H m/z=423.1).

EXAMPLE 63

2-[4-(1-Methyl-4-pyridin-4-yl-1H-pyrazol-3-yl)-phenoxymethyl]-pyrido[1,2-a]pyrimidin-4-one Following the procedure for the preparation of 2-[4-(4-Pyridin-4-yl-4H-[1,2,4]triazol-3-yl)-phenoxymethyl]-quinoline but substituting 2-Chloromethyl-pyrido[1,2-a]pyrimidin4-one provided the title compound. $^1$H NMR (400 MHz, CDCl$_3$) δ 9.01 (d, J=7.1 Hz, 1 H), 8.43 (m, 2H), 7.72 (m, 1H), 7.59 (d, J=8.7 Hz, 1H), 7.53 (s, 1H), 7.37 (d, J=9.1 Hz, 2H), 7.12 (m, 3H), 6.93 (d, J=8.7Hz, 2H), 6.68 (s, 1 H), 5.05 (s, 2H), 3.92 (s, 3H); MS: (M$^+$H m/z=410.1).

EXAMPLE 64

2-[4-(1-Methyl-4-pyridin-4-yl-1H-pyrazol-3-yl)-phenoxymethyl]-quinazoline

Following the procedure for the preparation of 2-[4-(4-Pyridin-4-yl-4H-[1,2,4]triazol-3-yl)-phenoxymethyl]-quinoline but substituting 2-Chloromethyl-quinazoline provided the title compound. $^1$H NMR (400 MHz, CDCl$_3$) δ 9.43 (s, 1H), 4.43 (d, J=4.6 Hz, 2 H), 8.07 (d, J=8.3 Hz, 1H), 7.93 (d, 2H), 7.69 (t, J=7.9 Hz, 1H), 7.55 (s, 1 H), 7.36 (d, J=8.7 Hz, 2 H), 7.15 (d, J=6.2, Hz, 2 H), 7.05 (d, J=8.7 Hz, 2H), 5.48 (s, 2H), 3.94 (s, 3H); MS: (M$^+$H m/z=394.2)

Preparation 49

4-Benzyloxy-2-fluoro-benzoic acid benzyl ester

Following the procedure for the preparation of 4-(Quinolin-2-ylmethoxy)-benzoic acid methyl ester but substituting two equivalents of benzyl bromide and 2-Fluoro4-hydroxy-benzoic acid provided the title compound. MS: (M$^+$H m/z=337.2).

Preparation 50

4-Benzyloxy-2-fluoro-benzoic acid

Following the procedure for the preparation of 4-(Quinolin-2-ylmethoxy)-benzoic acid but substituting 4-Benzyloxy-2-fluoro-benzoic acid benzyl ester provided the title compound. MS: (M$^+$H m/z=247.1).

Preparation 51

4-Benzyloxy-2-fluoro-N-methoxy-N-methyl-benzamide

Following the procedure for the preparation of N-Methoxy-N-methyl4-(quinolin-2-ylmethoxy)-benzamide but substituting 4-Benzyloxy-2-fluoro-benzoic acid provided the title compound. MS: (M$^+$H m/z=290.2).

Preparation 52

1-(4-Benzyloxy-2-fluoro-phenyl)-2-pyridin-4-yl-ethanone

Following the procedure for the preparation of 2-pyridin-4-yl-1-[4-(quinolin-2-ylmethoxy)-phenyl]-ethanone but substituting 4-Benzyloxy-2-fluoro-N-methoxy-N-methyl-benzamide provided the title compound. MS: (M$^+$H m/z=322.1).

Preparation 53

4-[3-(4-Benzyloxy-2-fluoro-phenyl)-1-methyl-1H-pyrazol-4-yl]-pyridine

Following the procedure for the preparation of 4-[3-(4-Benzyloxy-phenyl)-1-methyl-1H-pyrazol4-yl]-pyridine but substituting 1-(4-Benzyloxy-2-fluoro-phenyl)-2-pyridin4-yl-ethanone provided the title compound. MS: (M$^+$H m/z=360.1).

Preparation 54

3-Fluoro-4-(1-methyl-4-pyridin-4-yl-1H-pyrazol-3-yl)-phenol

Following the procedure for the preparation of 4-(1-Methyl4-pyridin-4-yl-1H-pyrazol-3-yl)-phenol but substituting 4-[3-(4-Benzyloxy-2-fluoro-phenyl)-1-methyl-iH-pyrazol4-yl]-pyridine provided the title compound. MS: (M$^+$H m/z=270.1).

EXAMPLE 65

2-[3-Fluoro-4-(1-methyl-4-pyridin-4-yl-1H-pyrazol-3-yl)-phenoxymethyl]-quinoline To a solution of 3-Fluoro-4-(1-methyl-4-pyridin4-yl-1H-pyrazol-3-yl)-phenol (450 mg) in dimethylformamide (10 ml) was added cesium carbonate (2 g) and 2-chloro methyl quinoline (481 mg) and the reaction mixture was heated at 60° C. for 18 h. The reaction mixture was poured into 1N NaOH, extracted with methylene chloride, dried magnesium sulfate, filtered and concentrated. Biotage MPLC purification eluting with methanol 2%/0.5% ammonium hydroxide/70% ethyl acetate/hexanes provided the title compound. The free base was stirred in ethyl acetate and 1.1 equivalents of succinic acid was added. The white precipitate was filtered and dried to provide the title compound as the succinate salt (280 mg). $^1$H NMR (400 MHz, DMSO) δ 8.43 (d, J=8.3 Hz, 1 H), 8.37 (d, J=6.2 Hz, 2H), 8.26 (s, 1H), 8.00 (m, 2H), 7.78 (t, J=7.1 Hz, 1H), 7.70 (d, J=8.3 Hz, 1 H), 7.61 (t, J=6.6 Hz, 1 H), 7.38 (t, J=8.3, Hz, 1 H), 7.10 (d, J=6.2 Hz, 2H), 7.00 (m, 2H), 5.40 (s, 2H), 3.88 (s, 3 H), 2.38 (s, 4H), MS: (M$^+$H m/z=411.1).

Preparation 55

4-[3-(4-Benzyloxy-2-fluoro-phenyl)-1H-pyrazol-4-yl]-pyridine

Following the procedure for the preparation of 2-[4-(4-Pyridin4-yl-1H-pyrazol-3-yl)-phenoxymethyl]-quinoline but substituting 1-(4-Benzyloxy-2-fluoro-phenyl)-2-pyridin-4-yl-ethanone provided the title compound. MS: (M$^+$H m/z=346.3).

Preparation 56

4-[3-(4-Benzyloxy-2-fluoro-phenyl)-1-(2,2,2-trifluoro-ethyl)-1H-pyrazol-4-yl]-pyridine Following the procedure for the preparation of 2-{4-[-Pyridin-4-yl-1-(2,2,2-trifluoro-ethyl)-1H-pyrazol-3-yl]-phenoxymethyl}-quinoline but substituting 4-[3-(4-Benzyloxy-2-fluoro-phenyl)-1H-pyrazol4-yl]-pyridine provided the title compound. MS: (M$^+$H m/z=428.4).

Preparation 57

3-Fluoro-4-[4-pyridin-4-yl-1-(2,2,2-trifluoro-ethyl)-1H-pyrazol-3-yl]-phenol

To 4-[3-(4-Benzyloxy-2-fluoro-phenyl)-1-(2,2,2-trifluoro-ethyl)-1H-pyrazol-4-yl]-pyridine (900 mg) was added trifluoroacetic acid (5.25 ml) and anisole (1.15 ml) and the reaction mixture heated at reflux for 18 h. The reaction mixture was quenched with with 1N NaOH, extracted 3× tetrahydrofuran, dried magnesium sulfate, filtered and concentrated. Purification via Biotage MPLC eluting with 5% methanol/1% ammonium hydroxide/ethyl acetate provided the title compound (552 mg). MS: (M$^+$H m/z=338.2).

EXAMPLE 66

2-{3-Fluoro-4-[4-pyridin-4-yl-1-(2,2,2-trifluoro-ethyl)-1H-pyrazol-3-yl]-phenoxymethyl}-quinoline Following the procedure for the preparation of 2-[3-Fluoro4-(1-methyl4-pyridin-4-yl-1H-pyrazol-3-yl)-phenoxymethyl]-quinoline but substituting 3-Fluoro4-[4-pyridin-4-yl-1-(2,2,2-trifluoro-ethyl)-1H-pyrazol-3-yl]-phenol and acetone as the solvent provided the title compound. $^1$H NMR (400 MHz, CDCl$_3$) δ 8.46 (m, 2 H), 7.80 (s, 1H), 7.31 (t, J=8.3 Hz, 1H), 7.24 (m, 5 H), 6.72 (dd, J=8.3, 2.5 Hz, 1 H), 6.50 (dd, J=11.6, 2.1 Hz, 1 H), 4.81 (q, J=8.4 Hz, 2H); MS: (M$^+$H m/z=479.2).

EXAMPLE 67

2-{3-Fluoro-4-[4-pyridin-4-yl-1-(2,2,2-trifluoro-ethyl)-1H-pyrazol-3-yl]-phenoxymethyl}-quinoxaline Following the procedure for the preparation of 2-[3-Fluoro4-(1-methyl4-pyridin-4-yl-1H-pyrazol-3-yl)-phenoxymethyl]-quinoline but substituting 3-Fluoro4-[4-pyridin4-yl-1-(2,2,2-trifluoro-ethyl)-1H-pyrazol-3-yl]-phenol, 2-Chloromethyl-quinoxaline and acetone as the solvent provided the title compound. $^1$H NMR (400 MHz, CDCl$_3$) δ 9.09 (s, 1 H), 8.46 (m, 2H), 8.15 (m, 1H), 8.09 (m, 1 H), 7.81 (m, 3H), 7.43 (t, J=8.7Hz, 1H), 7.12 (d, J=6.2 Hz, 2H), 6.93 (dd, J=7.9, 2.0 Hz, 1 H), 6.81 (dd, J=11.6, 2.5 Hz, 1 H), 5.43 (s, 2H), 4.80 (q, J=8.3 Hz, 2H); MS: (M$^+$H m/z=480.1).

EXAMPLE 68

4-Chloro-2-[4-(1-methyl4-pyridin-4-yl-1H-pyrazol-3-yl)-phenoxymethyl]-quinoline

Following the procedure for the preparation of 2-{4-[4-Pyridin-4-yl-1-(2,2,2-trifluoro-ethyl)-1H-pyrazol-3-yl]-phenoxymethyl}-quinoxaline but substituting 4-(1-Methyl-4-pyridin4-yl-1H-pyrazol-3-yl)-phenol and (4-Chloro-quinolin-2-yl)-methanol provided the title compound. $^1$H NMR (400 MHz, CDCl$_3$) δ 8.43 (d, J=4.6 Hz, 2 H), 8.18 (d, J=8.7 Hz, 1H), 8.04 (d, J=7.9 Hz, 1H), 7.73 (m, 2H), 7.60 (t, J=7.1 Hz, 1 H), 7.52 (s, 1 H), 7.37 (d, J=9.1, Hz, 2 H), 7.12 (d, J=6.2 Hz, 2H), 6.98 (d, J=8.7 Hz, 2 H), 5.30 (s, 2H), 3.90 (s, 3 H); MS: (M$^+$H m/z=427.1).

EXAMPLE 69

4-Methoxy-2-[4-(1-methyl-4-pyridin4-yl-1H-pyrazol-3-yl)-phenoxymethyl]-quinoline To a solution of 4-Chloro-2-[4-(1-methyl-4-pyridin-4-yl-1H-pyrazol-3-yl)-phenoxymethyl]-quinoline (125 mg) in methanol (4 mL) was added phenanthroline (78 mg), cesium carbonate (143 mg) and copper iodide (5 mg). The reaction mixture was heated in a microwave reactor at 165° C. with 50 W of power for 20 min. The reaction mixture was filtered through celite and concentrated. Purification via MPLC biotage chromatography, eluting with 5% methanol/1% ammonium hydroxide/methylene chloride provided the title compound (74 mg). $^1$H NMR (400 MHz, CDCl$_3$) δ 8.45 (d, J=5.4 Hz, 2 H), 8.18 (d, J=8.3 Hz, 1H), 7.97 (d, J=8.3 Hz, 1H), 7.68 (m, 1H), 7.55 (s, 1H), 7.49 (t, J=7.1 Hz, 1 H), 7.37 (d, J=9.1, Hz, 2 H), 7.15 (d, J=6.2 Hz, 2H), 7.01 (m, 3H), 5.32 (s, 2H), 4.02 (s, 3 H), 3.95 (s, 3H); MS: (M$^+$H m/z=423.3).

EXAMPLE 70

Dimethyl-{2-[4-(1-methyl-4-pyridin-4-yl-1H-pyrazol-3-yl)-phenoxymethyl]-quinolin-4-yl}-amine To a solution of 4-Chloro-2-[4-(1-methyl-4-pyridin-4-yl-1H-pyrazol-3-yl)-phenoxymethyl]-quinoline (135 mg) in tetrahydrofuran (4 mL) was added dimethylamine (2N in methanol, 0.32 mL), cesium fluoride (5 mg), diisopropyl ethyl amine (62 mg) and tetrabutyl ammonium iodide (12 mg). The reaction mixture was heated in a microwave reactor at 180° C. with 100 W of power for 40 min. The reaction mixture was filtered through celite and concentrated. Purification via MPLC biotage chromatography, eluting with 5% methanol/1% ammonium hydroxide/methylene chloride provided the title compound (36 mg). $^1$H NMR (400 MHz, CDCl$_3$) δ 8.45 (d, J=6.2Hz, 2 H), 8.04 (d, J=8.3 Hz, 1H), 7.99 (d, J=8.3 Hz, 1H), 7.62 (m, 1H), 7.56 (s, 1H), 7.42 (m, 1 H), 7.38 (d, J=9.1 Hz, 2 H), 7.15 (d, J=6.2 Hz, 2H), 7.01 (m, 3H), 5.29 (s, 2H), 3.95 (s, 3 H), 3.03 (s, 6H); MS: (M$^+$H m/z=436.3).

Preparation 58

N-Methoxy-N-methyl-4-triisopropylsilanyloxymethyl-benzamide

Following the procedure for the preparation of 4-benzyloxy-N-methoxy-N-methyl-benzamide but substituting 4-Triisopropylsilanyloxymethyl-benzoic acid provided the title compound. MS: (M$^+$H m/z=352.1).

Preparation 59

2-Pyridin-4-yl-1-(4-triisopropylsilanyloxymethyl-phenyl)-ethanone

Following the procedure for the preparation of 1-(4-Benzyloxy-phenyl)-2-pyridin-4-yl-ethanone but substituting N-Methoxy-N-methyl-4-triisopropylsilanyloxymethyl-benzamide provided the title compound. MS: (M$^+$H m/z=384.1).

Preparation 60

4-[1-Methyl-3-(4-triisopropylsilanyloxymethyl-phenyl)-1H-pyrazol-4-yl]-pyridine

Following the procedure for the preparation of 4-[3-(4-Benzyloxy-phenyl)-1-methyl-1H-pyrazol-4-yl]-pyridine but substituting 2-Pyridin-4-yl-1-(4-triisopropylsilanyloxymethyl-phenyl)-ethanone provided the title compound. MS: (M$^+$H m/z=422.2).

Preparation 61

[4-(1-Methyl-4-pyridin-4-yl-1H-pyrazol-3-yl)-phenyl]-methanol

To a solution of 4-[1-Methyl-3-(4-triisopropylsilanyloxymethyl-phenyl)-1H-pyrazol-4-yl]-pyridine (1.75 g) in THF (16.2 mL) was added TBAF (1.0M THF, 5.2 mL) and the reaction mixture stirred at ambient temperature under inert atmosphere for 1 h. The reaction mixture was poured into saturated sodium bicarbonate, extracted 3× with chloroform, dried magnesium sulfate filtered and concentration. Purification via MPLC biotage chromatography eluting with 2% methanol/0.5% saturated ammonium hydroxide/50% ethyl acetate/hexanes provided the title compound (920 mg, 84%). MS: (M$^+$H m/z=266.1).

EXAMPLE 71

2-[4-(1-Methyl-4-pyridin-4-yl-1H-pyrazol-3-yl)-benzyloxy]-quinoline di succinic acid Following the procedure for the preparation of 2-{4-[4-Pyridin4-yl-1-(2,212-trifluoro-ethyl)-1H-pyrazol-3-yl]-phenoxymethyl}-quinoxaline but substituting [4-(1-Methyl-4-pyridin-4-yl-1H-pyrazol-3-yl)-phenyl]-methanol and Quinolin-2-ol provided the title compound. $^1$H NMR (400 MHz, DMSO) δ 8.42 (d, J=5.0 Hz, 2 H), 8.25 (d, J=8.7 Hz, 1H), 8.14 (s, 1H), 7.88 (d, J=7.9 Hz, 1H), 7.78 (d, J=7.9 Hz, 1H), 7.66 (t, J=7.1 Hz, 1 H), 7.51 (d, J=7.5 Hz, 2 H), 7.40 (m, 3 H), 7.19 (d, J=4.6 Hz, 2H), 7.07 (d, J=8.7 Hz, 1H), 5.49 (s, 2H), 2.38 (s, 8 H); MS: (M$^+$H m/z=393.1).

Preparation 62

N-((4-(Benzyloxy)phenyl)(tosyl)methyl)formamide

A mixture of 4-methylbenzenesulfinic acid (3.1 g, 19.9 mmol), 4-(benzyloxy)benzaldehyde (4.2 g, 19.9 mmol), and formamide (4.5 mL) was heated at 60° C. for 20 h. The mixture was diluted with methanol and stirring was continued for 1 h at rt. The resultant solid was filtered and dried to give 3.81 g (49%) of a white solid. The product was used in the next step without future purification.

Preparation 63

1-((4-(Benzyloxy)phenyl)isocyanomethylsulfonyl)-4-methylbenzene

To a solution of N-((4-(Benzyloxy)phenyl)(tosyl)methyl) formamide (3.2 g, 8.1 mmol) in 43 mL of DME (dimethoxy ethane) at 0° C. was added POCl$_3$ (2.27 mL) followed by the dropwise addition of triethylamine (5.6 mL). The resultant solution was then stirred at 0° C. for 3 h and finally poured into cooled water. The precipitate was collected and dried to give 3.3 g of pale yellow solid. MS m/z: 378 [M+1]$^+$.

Preparation 64

4-(4-(4-(Benzyloxy)phenyl)oxazol-5-yl)pyridine

A mixture of 1-((4-(Benzyloxy)phenyl)isocyanomethylsulfonyl)4-methylbenzene (4.3 g, 11.4 mmol), isonicotinaldehyde (1.34 g, 12.5 mmol) and K$_2$CO$_3$ (3.15 g, 22.8 mmol) in methanol (96 mL) and DME (30 mL) was heated at reflux for 5 h. After removal of solvent, the residue was purified by silica gel chromatography (2:1 hexane/EtOAc) to provide 2.29 g (84%) of a white solid. $^1$H NMR (400 MHz, CDCl$_3$) δ: 5.12v (s, 2H), 7.03 (d, 2H), 7.46 (m, 6H), 7.56 (d, 2H), 7.61 (d, 2H), 8.02 (s, 1H), 8.58 (d, 2H). MS m/z: 329 [M+1]$^+$.

Preparation 65

4-(5-(pyridin-4-yl)oxazol-4-yl)phenol

To a solution of 4-(4-(4-(Benzyloxy)phenyl)oxazol-5-yl) pyridine (300 g, 0.91 mmol) was added 20% Pd(OH)$_2$/C (30 mg) and ammonium formate (115 mg, 1.83 mmol) in methanol (8 mL). The solution was heated at 60° C. for 20 min. The catalyst was removed by filtration and the filtrate was concentrated to give 208 mg (96%) of the title compound. $^1$H NMR (400 MHz, CDCl$_3$) δ: 6.92 (m, 2H), 7.46 (m, 2H), 7.57 (d, 2H), 8.02 (s, 1H), 8.58 (m, 2H). MS m/z: 239 [M+1]$^+$.

EXAMPLE 72

2-((4-(5-(pyridin-4-yl)oxazol-4-yl)phenoxy)methyl)quinoline

To a solution of compound 4-(5-(pyridin4-yl)oxazol4-yl) phenol (90 mg, 0.38 mmol) in 1 mL of dry DMF was added CsF (115 mg, 0.76 mmol). After stirring for 0.5 h, 2-(chloromethyl)quinoline (67 mg, 0.38 mmol) was added and the reaction was heated at 80° C. for 48 h. Upon removal of DMF under vacuum, the residue was purified by PTLC (1:2 hexane/ EtOAc) to give 29 mg (20%) of the title compound as a white solid. $^1$H NMR (400 MHz, CDCl$_3$) δ: 5.47 (s, 2H), 7.11 (m, 2H), 7.56 (m, 5H), 7.70 (d, 1H), 7.78 (t, 1H), 7.86 (d, 1H), 8.01 (s, 1H), 8.12 (d, 1H), 8.26 (d, 1H), 8.57 (d, (2H). MS m/z: 380 [M+1]$^+$.

Preparation 66

1-(4-(benzyloxy)phenyl)-2-bromo-2-(pyridin-4-yl) ethanone

To a solution of 1-(4-(benzyloxy)phenyl)-2-(pyridin-4-yl) ethanone (1.39 g, 4.58 mmol) in acetic acid was added a solution of bromine (0.72 g, 4.58 mmol) in acetic acid (3 mL). After stirring 2 h, the solid was collected via filtration and washed with acetic acid to provide 1.67 g (96%) of the title compound as a pale yellow solid. $^1$H NMR (400 MHz, DMSO) δ: 5.21 (s, 1H), 7.15 (d, 2H), 7.42 (m, 3H), 7.87 (m, 1H), 8.06 (d, 2H), 8.77 (m, 1H). MS m/z: 382 [M+1]$^+$.

Preparation 67

4-(4-(4-(benzyloxy)phenyl)-2-methyloxazol-5-yl) pyridine

To a mixture of sodium acetate (323 mg, 2.38 mmol) and ammonium acetate (304 mg, 3.95 mmol) in acetic acid (10 mL) was added 1-(4-(benzyloxy)phenyl)-2-bromo-2-(pyridin-4-yl)ethanone (302 mg, 0.79 mmol). The resulting mixture was then refluxed for 48 h. After removal of the solvent under vacuum, the residue was dissolved in ethyl acetate and the solution was washed with satd NaHCO3. The organic phase was dried and concentrated in vacuum to give an oil, which was purified via silica gel chromatography (1:3 EtOAc/n-hexane) to provide 111 mg (41%) of the title compound. $^1$H NMR (400 MHz, CDCl$_3$) δ: 2.58 (s, 3H), 5.15 (s, 2H), 7.01 (d, 2H), 7.39 (m, 7H), 7.56 (d, 2H), 8.57 (d, 2H). MS m/z: 343 [M+1]$^+$.

Preparation 68

4-(2-methyl-5-(pyridin-4-yl)oxazol-4-yl)phenol 4-(4-(4-(Benzyloxy)phenyl)-2-methyloxazol-5-yl)pyridine was hydrogenated in the presence of ammonium formate and Pd(OH)$_2$ in methanol for 1 h at 50° C. The catalyst was removed via filtration and the filtrate was concentrated. The resultant residue was dissolved in methylene chloride and dried with Na$_2$SO$_4$. Evaporation of the solvent gave 69 mg (86%) of the title compound as a brown solid. MS m/z: 253.

EXAMPLE 73

2-((4-(2-methyl-5-(pyridin-4-yl)oxazol-4-yl)phenoxy)methyl)quinoline

To a solution of 4-(2-methyl-5-(pyridin-4-yl)oxazol-4-yl) phenol (21 mg, 0.083 mmol) in 2.5 mL of dry DMF was added Cs$_2$CO$_3$ (54 mg, 0.17 mmol). After stirring for 0.5 h, 2-(chloromethyl)quinoline (17.8 mg, 0.100 mmol) was added and the mixture was stirred at 85° C. for 12 h. After removal of the DMF under vacuum, the residue was purified by PTLC (1:2 hexane/EtOAc) to give 13 mg (40%) of the title compound as a pale yellow solid. $^1$H NMR (400 MHz, CDCl$_3$) δ: 2.54 (s, 3H), 5.41 (s, 2H), 7.06 (m, 2H), 7.41 (m, 2H), 7.53 (m, 3H), 7.68 (d, 1H), 7.80 (t, 1H), 7.83 (d, 1H), 8.05 (d, 1H), 8.20 (d, 1H), 8.53 (m, 2H). MS m/z: 394 [M+1]$^+$.

Preparation 69

4-(4-((quinolin-2-yl)methoxy)phenyl)-3-(pyridin-4-yl)but-3-en-2-one

A mixture of 4-((quinolin-2-yl)methoxy)benzaldehyde (2.5 g, 9.5 mmol), 1-(pyridin-4-yl)propan-2-one (1.3 g, 9.5 mmol) and piperidine (162 mg, 1.9 mmol) in toluene (50 mL) was heated at reflux for 18 h, concentrated, and the residue chromatographed on silica eluting with a gradient of ethyl acetate in hexanes giving impure title substance (2.4 g) as a yellow solid which was chromatographed again on silica eluted with 1% and 2% methanol in dichloromethane containing 0.5% concentrated ammonium hydroxide giving a 3:1 mixture of the title substance contaminated with the pyridyl starting material. Yield 2.0 g, 55%. The title substance appeared to be a 10:1 mixture of two isomers by NMR. $^1$H NMR (CDCl$_3$, 400 mHz, partial) δ 2.35 (s, 3H, major isomer), 2.23 (s, 3H, minor isomer). HPLC-MS 6.09 min, m/e 381 (MH+).

EXAMPLE 74

2-((4-(3-Methyl-4-(pyridin-4-yl)-1H-pyrazol-5-yl) phenoxy)methyl)quinoline

A mixture of 4-(4-((quinolin-2-yl)methoxy)phenyl)-3-(pyridin-4-yl)but-3-en-2-one (1.00 g, 2.60 mmol) and p-toluensulfonylhydrazine (484 mg, 2.6 mmol) in acetic acid (14 mL) was heated at reflux for 10 h. Additional p-toluenesulfonylhydrazine (242 mg, 0.5 mmol) was added and the mixture heated at reflux 2 h. The mixture was concentrated, the residue dissolved in dichloromethane and the resulting solution washed with water (2×25 mL), dried and concentrated. The residue was chromatographed on silica eluted with 1%, 2%, and 3% methanol in dichloromethane containing 0.5% concentrated ammonium hydroxide giving a solid which was triturated with ether and dried. Yield 293 mg, 29%. $^1$H NMR (CDCl$_3$, 400 mHz) δ 8.51 (m, 2H), 8.18 (d, 1H, J=8.7 Hz), 8.06 (d, 1H, J=7.9 Hz), 7.81 (d, 1H, J=8.3 Hz), 7.72 (m, 1H), 7.64 (d, 1H, J=8.3 Hz), 7.54 (m, 1H), 7.24 (m, 2H), 7.13 (m, 2H), 6.96 (m, 2H), 5.36 (s, 2H), 2.33 (s, 3H). HPLC-MS (system 1) 4.65 min, m/e 393 (MH+).

EXAMPLE 75

2-((4-(1,3-dimethyl-4-(pyridin-4-yl)-1H-pyrazol-5-yl)phenoxy)methyl)quinoline

A solution of 2-((4-(3-methyl-4-(pyridin-4-yl)-1H-pyrazol-5-yl)phenoxy)methyl)quinoline (150 mg, 0.38 mmol) in anhydrous dimethylformamide (2 mL) was treated at 0° C. with sodium hydride dispersion (30 mg, 0.76 mmol of 60% NaH in oil) followed after 20 min with methyl iodide (54 mg, 0.38 mmol), and the stirred mixture was allowed to warm to RT overnight. Water was added and the mixture extracted with dichloromethane (3×20 mL). The organic layer was dried, concentrated, and the residue chromatographed on silica eluted with an ethyl acetate-hexane gradient containing 1% triethylamine, giving fractions containing two isomeric substances. The less polar isomer (18 mg) was thus obtained (methylation regiochemistry tentatively assigned by NMR). $^1$H NMR (CDCl$_3$, 400 mHz) δ 8.41 (m, 2H), 8.21 (d, 1H, J=8.7 Hz), 8.07 (d, 1H, J=8.3 Hz), 7.84 (d, 1H, J=9.5 Hz), 7.74 (ddd, 1H), 7.67 (d, 1H, J=8.3 Hz), 7.55 (ddd, 1H), 7.12 (m, 2H), 7.05 (m, 2H), 7.0 (m, 2H), 5.40 (s, 2H), 3.71 (s, 3H), 2.37 (s, 3H). HPLC-MS 4.81 min, m/e 407 (MH+).

EXAMPLE 76

2-((4-(1,5-dimethyl-4-(pyridin-4-yl)-1H-pyrazol-3-yl)phenoxy)methyl)quinoline The more polar fractions obtained from the sodium hydride/methyl iodide alkylation of 2-((4-(3-methyl-4-(pyridin-4-yl)-1H-pyrazol-5-yl)phenoxy)methyl)quinoline gave 26 mg of impure title substance which was recrystallized from 10:1 ethyl acetate-hexanes giving isomerically pure material whose methylation regiochemistry was tentatively assigned by NMR. $^1$H NMR (CDCl$_3$, 400 mHz) δ 8.51 (m, 2H), 8.17 (d, 1H, J=8.7 Hz), 8.05 (d, 1H, J=8.3 Hz), 7.85 (d, 1H, J=8.3 Hz), 7.72 (ddd, 1H), 7.65 (d, 1H, J=8.7 Hz), 7.53 (t, 1H, J=7.5 Hz), 7.27 (m, 2H), 7.12-7.11 (m, 2H), 6.93 (m, 2H), 5.36 (s, 2H), 3.87 (s, 3H), 2.30 (s, 3H), HPLC-MS 4.78 min, m/e 407 (MH+).

Preparation 69a

1-(quinolin-2-yl)ethanol

A solution of methylmagnesium bromide (17.6 mL of 1.4 M in toluene, 24.7 mmol) was added at <10° C. to a solution of quinoline-2-carboxaldehyde (3.0 g, 19 mmol) in anhydrous tetrahydrofuran (50 mL). The mixture was stirred at RT for 1 h and poured into saturated aqueous ammonium chloride (100 mL), and the resulting mixture was extracted with ethyl acetate (3×150 mL). The extracts were dried, concentrated, and the residue chromatographed on silica eluted with 30% and 40% ethyl acetate-hexanes giving a yellow solid. Yield 2.46 g, 75%. $^1$H NMR (CDCl$_3$, 400 mHz) δ 8.15 (d, 1H, J=8.7 Hz), 8.07 (d, 1H, J=8.7 Hz), 7.81 (dd, 1H, J=1, 8 Hz), 7.71 (ddd, 1H, J=1, 7, 8.5 Hz), 7.51 (ddd, 1H, J=1, 7, 8.3 Hz), 7.33 (d, 1H, J=8.3 Hz), 5.07-4.99 (m, 2H), 1.56 (d, 3H, J=6.2 Hz).

EXAMPLE 77

2-(1-(4-(1-methyl-4-(pyridin-4-yl)-1H-pyrazol-3-yl)phenoxy)ethyl)quinoline

A mixture of 4-(1-methyl-4-(pyridin-4-yl)-1H-pyrazol-3-yl)phenol (75 mg, 0.30 mmol) and 1-(quinolin-2-yl)ethanol (78 mg, 0.45 mmol) in p-dioxane (2 mL) was treated sequentially at RT with triphenylphosphine (126 mg, 0.48 mmol) and di-t-butyldiazodicarboxylate (110 mg, 0.48 mmol) and the mixture was heated at 60° C. for 4 h. Aqueous 2N NaOH was added and the mixture extracted with dichloromethane. The organic layers were dried, concentrated, and the residue purified on silica gel eluted with a gradient of ethyl acetate-hexanes giving a yellow solid. Yield 36 mg, 29%. $^1$H NMR (CDCl$_3$, 400 mHz) δ 8.40 (m, 2H), 8.10 (d, 1H, J=8.7 Hz), 8.06 (d, 1H, J=7.5 Hz), 7.77 (d, 1H, J=8.3 Hz), 7.71 (ddd, 1H), 7.55 (d, 1H, J=8.3 Hz), 7.53-7.49 (m, 2H), 7.25 (m, 2H), 7.10 (m, 2H), 6.88 (m, 2H), 5.59 (q, 1H, J=6.6 Hz), 3.91 (s, 3H), 1.75 (d, 3H, J=6.6 Hz). HPLC-MS (system 1) 4.73 min, m/e 407 (MH+).

Preparation 70

2-((4-(2-(pyridin-4-yl)ethynyl)phenoxy)methyl)quinoline

A mixture of 4-(2-(pyridin-4-yl)ethynyl)phenol (335 mg, 1.72 mmol), 2-(chloromethyl)quinoline hydrochloride (385 mg, 1.8 mmol), and cesium carbonate (2.2 g, 6.87 mmol) was stirred in dimethylformamide (8 mL) at 65° C. for 3 h. Water (20 mL) was added and the mixture was extracted with dichloromethane (3×15 mL). The organic layers were dried, concentrated, and the residue chromatographed on silica eluted with a gradient of 10% to 80% ethyl acetate-hexanes giving 450 mg (78%) of a yellow solid. $^1$H NMR (CDCl$_3$, 400 mHz) δ 8.56 (m, 2H), 8.20 (d, 1H, J=8.7 Hz), 8.08 (d, 1H, J=8.3 Hz), 7.82 (d, 1H, J=7.9 Hz), 7.74 (ddd, 1H, J=8.4, 7, 1Hz), 7.63 (d, 1H, J=8.7 Hz), 7.55 (ddd, 1H, J=8, 7, 1 Hz), 7.47 (m, 2H), 7.35 (m, 2H), 7.01 (m, 2H), 5.41 (s, 2H). MS (AP+) m/e 337 (MH+).

Preparation 71

4-(2-(pyridin-4-yl)ethynyl)phenol

Boron tribromide (1M in dichloromethane, 9.7 mL, 9.7 mmol) was added at 0° C. to a solution of 4-(2-(4-methoxyphenyl)ethynyl)pyridine (810 mg, 3.88 mmol) in dichloromethane (10 mL) and the mixture was stirred at RT for 5 h. Aqueous 1 N sodium hydroxide (20 mL) was added and after 40 min the pH was brought between 7 and 8 by addition of 1 N HCl. The resulting mixture was extracted with 4:1 dichloromethane:2-propanol (3×30 mL). The organic layers were dried, concentrated and evaporated and the residue chromatographed on silica in a gradient from 25% to 80% ethyl acetate-hexanes giving a brown solid. Yield 450 mg, 60%. $^1$H NMR (CDCl$_3$ containing CD$_3$OD, 400 mHz) δ 8.50 (br, 2H), 7.38 (br, 2H), 7.37 (d, 2H, J=8.7 Hz), 6.77 (d, 2H, J=8.7 Hz), 3.11 (br, 2H, OH+H2O). MS (AP+) m/e 196 (MH+).

Preparation 72

4-(2-(4-methoxyphenyl)ethynyl)pyridine

A mixture of 4-methoxyphenylacetylene (2.86 g, 21.7 mmol), 4-iodopyridine (4.44 g, 21.7 mmol), cuprous iodide (206 mg, 1.08 mmol), bis(triphenylphosphine)palladium(II) dichloride (758 mg, 1.08 mmol) in tetrahydrofuran (40 mL) and triethylamine (20 mL) was heated at reflux for 2 h. The mixture was filtered, concentrated, and the residue chromaptographed on silica in 1:1 ethyl acetate-hexanes giving 2.45 g (54%) of a yellow solid. $^1$H NMR (CDCl$_3$, 400 mHz) δ 9.2 (very broad, 2H), 7.57 (br, 2H), 7.48 (d, 2H, J=8.7 Hz), 6.88 (d, 2H, J=8.7 Hz), 3.82 (s, 3H). MS (AP+) m/e 210 (MH+).

EXAMPLE 78

2-((4-(5-(pyridin-4-yl)-1,2,3-triazol-4-yl)phenoxy)methyl)quinoline

Trimethylsilylazide (730 mg, 6.4 mmol) and 2-((4-(2-(pyridin-4-yl)ethynyl)phenoxy)methyl)quinoline (360 mg) were combined in a screw cap sealed tube and heated behind a safety shield in a 150° C. bath for 72 h. The mixture was concentrated and the yellow residue triturated with ether (2×10 mL) leaving a yellow solid (346 mg) which was chromatographed on silica eluted with a gradient of 0.5%-2% methanol in dichloromethane giving a yellow solid (210 mg, 52%). $^1$H NMR (CDCl$_3$ with a drop of CD$_3$OD, 400 mHz) δ 8.54 (d, 2H, J=6.2 Hz), 8.23 (d, 1H, J=8.7 Hz), 8.07 (d, 1H, J=8.7 Hz), 7.84 (d, 1H, J=7.9 Hz), 7.74 (ddd, 1H, J=8.4, 7, 1Hz), 7.69 (d, 1H, J=8.7 Hz), 7.63 (d, 2H, J=6.2 Hz), 7.56 (ddd, 1H), 7.41 (m, 2H), 7.09 (m, 2H), 5.41 (s, 2H). MS (AP+) m/e 380 (MH+).

Preparation 73

4-(2-methyl-5-(pyridin-4-yl)-2H-1,2,3-triazol-4-yl)phenol

A solution of 4-(5-(4-methoxyphenyl)-2-methyl-2H-1,2,3-triazol-4-yl)pyridine (203 mg, 0.76 mmol) in dichloromethane (5 mL) was treated at 0° C. with boron tribromide (2.3 mL of 1M in dichloromethane) and the mixture stirred 18 h at RT. Methanol (3 mL) was added and the mixture was concentrated and extracted using dichloromethane and aqueous sodium bicarbonate. The organic extracts were dried and concentrated giving a yellow solid which was chromatographed on silica (gradient of 0.5%-3% methanol in dichloromethane) giving two substances. The more polar substance (88 mg) was assigned 4-(2-methyl-5-(pyridin4-yl)-2H-1,2,3-triazol-4-yl)phenol. $^1$H NMR (CDCl$_3$, 400 mHz, partial) δ 8.57 (br, 2H), 7.59 (d, 2H, J=5.2 Hz), 7.32 (m, 2H), 6.90 (m, 2H), 4.26 (s, 3H). HPLC-MS (system 1) 3.96 min, m/e 253 (MH+). The less polar substance (80 mg) was assigned to be the corresponding boronate as it was found to convert on treatment with aqueous NaOH to the less polar substance.

Preparation 74

4-(5-(4-methoxyphenyl)-2-methyl-2H-1,2,3-triazol-4-yl)pyridine, 4-(5-(4-methoxyphenyl)-1-methyl-1H-1,2,3-triazol-4-yl)pyridine, and 4-(5-(4-methoxyphenyl)-3-methyl-3H-1,2,3-triazol-4-yl)pyridine Sodium hydride (240 mg of 60% oil dispersion, 6.0 mmol) was added to a solution of 4-(5-(4-methoxyphenyl)-1,2,3-triazol-4-yl)pyridine (755 mg, 3.0 mmol) in dimethylformamide (10 mL) at 0° C. and the mixture was stirred 30 min. Methyl iodide (425 mg) was added and the mixture was stirred at 0° C. for 2.5 h, quenched with water (20 mL), and extracted with dichloromethane (3×20 mL). The organic layers were dried over magnesium sulfate and concentrated. The residue was chromatographed on silica eluted with a gradient of 50% to 100% ethyl acetate-hexanes providing three isomeric substances of increasing polarity. Each showed a mass of m/e 267 (MH+) by HPLC-MS. Each structure was assigned by single crystal X-ray on crystals grown from either ethyl acetate or acetonitrile. The least polar substance (454 mg of yellow solid), 4-(5-(4-methoxyphenyl)-2-methyl-2H-1,2,3-triazol-4-yl)pyridine, $^1$H NMR (CDCl$_3$, 400 mHz) δ 8.59 (br, 2H), 7.52 (br, 2H), 7.41 (m, 2H), 6.93 (m, 2H), 4.26 (s, 3H), 3.84 (s, 3H). The middle-polarity substance (235 mg yellow solid), 4-(5-(4-methoxyphenyl)-1-methyl-1H-1,2,3-triazol-4-yl)pyridine, $^1$H NMR (CDCl$_3$, 400 mHz) δ 8.49 (d, 2H, J=6.22), 7.52 (m, 2H), 7.24 (m, 2H), 7.06 (m, 2H), 3.91 (s, 3H), 3.89 (s, 3H). The most polar substance (50 mg yellow solid), 4-(5-(4-methoxyphenyl)-3-methyl-3H-1,2,3-triazol-4-yl)pyridine, $^1$H NMR (CDCl$_3$, 400 mHz) δ 8.59 (br, 2H), 7.52 (br, 2H), 7.41 (m, 2H), 6.93 (m, 2H), 4.26 (s, 3H), 3.84 (s, 3H).

Preparation 75

4-(5-(4-methoxyphenyl)-1,2,3-triazol-4-yl)pyridine 4-(2-(4-methoxyphenyl)ethynyl)pyridine (1.48 g, 7.1 mmol) and trimethylsilylazide (2.5 g, 21.3 mmol) were combined in a sealed tube which was heated 48 h in a 150° C. oil bath. The mixture was chromatographed on silica using an ethyl acetate-hexanes gradient giving a yellow solid (950 mg, 53%). $^1$H NMR (CDCl$_3$, 400 mHz) δ 8.50 (d, 2H, J=5.8 Hz), 7.60 (d, 2H, J=5.8 Hz), 7.36 (d, 2H, J=8.7 Hz), 6.92 (d, 2H, J=8.7 Hz), 3.81 (s, 3H), 2.80 (br, 1H). MS (AP+) m/e 253 (MH+).

EXAMPLE 79

2-((4-(2-methyl-5-(pyridin-4-yl)-2H-1,2,3-triazol-4-yl)phenoxy)methyl)quinoline

A mixture of 4-(2-methyl-5-(pyridin-4-yl)-2H-1,2,3-triazol-4-yl)phenol (80 mg, 0.32 mmol), 2-(chloromethyl)quinoline hydrochloride (71 mg, 0.33 mg), and cesium carbonate (414 mg, 1.27 mmol) in dimethylformamide was heated at 65° C. for 20 h, filtered, the filtrate concentrated and chromatographed on silica eluted with ethyl acetate-hexanes providing material containing starting phenol. This was dissolved in ethyl acetate, washed with aqueous NaOH, dried and concentrated giving a colorless solid (100 mg, 80%). $^1$H NMR (CDCl$_3$, 400 mHz) δ 8.56 (d, 2H, J=6.2 Hz), 8.24 (d,1H, J=8.3 Hz), 8.12 (d, 1H, J=8.3 Hz), 7.85 (d, 1H, J=8.3 Hz), 7.75 (ddd, 1H, J=8.5, 7, 1.6 Hz), 7.70 (d, 1H, J=8.7 Hz), 7.65 (d, 2H, J=6.2 Hz), 7.57 (m, 1H), 7.41 (m, 2H), 7.08 (m, 2H), 5.45 (s, 2H), 4.27 (s, 3H). MS (AP+) m/e 394 (MH+).

Preparation 76

4-(3-methyl-5-(pyridin-4-yl)-3H-1,2,3-triazol-4-yl)phenol

A solution of 4-(5-(4-methoxyphenyl)-1-methyl-1H-1,2,3-triazol-4-yl)pyridine (170 mg, 0.64 mmol) in dichloromethane (5 mL) was treated at RT With boron tribromide (1.27 mL of 1M in dichloromethane) and the mixture was stirred overnight. Aqueous 1N NaOH (10 mL) was added, and after being stirred 1 h the mixture was extracted with dichloromethane (20 mL). The aqueous layer was acidified to pH 7 with 2N HCl, and extracted with ethyl acetate (2×15 mL). The extracts were dried with sodium sulfate and concentrated giving a yellow solid (142 mg, 88%). $^1$H NMR (CDCl$_3$, 400 mHz) δ $^1$H NMR (CDCl$_3$, 400 mHz) δ 8.39 (d, 2H, J=5-6 Hz), 7.49 (d, 2H, J=5-6 Hz), 7.09 (d, 2H, J=8.7 Hz), 6.95 (d, 2H, J=8.7 Hz), 3.87 (s, 3H). MS (AP−) 351 (M−H).

EXAMPLE 80

2-((4-(3-methyl-5-(pyridin-4-yl)-3H-1,2,3-triazol-4-yl) phenoxy)methyl)quinoline A mixture of 4-(3-methyl-5-(pyridin-4-yl)-3H-1,2,3-triazol-4-yl)phenol (88 mg, 0.35 mmol), 2-(chloromethyl)quinoline hydrochloride (82 mg, 0.38 mmol), and cesium carbonate (455 mg, 1.4 mmol) in dimethylformamide was stirred at 65° C. for 20 h, filtered, and concentrated. The residue was chromatographed on silica eluting with a gradient of 50% to 100% ethyl acetate in hexanes giving a light yellow solid (100 mg, 73%). $^1$H NMR (CDCl$_3$, 400 mHz) δ 8.48 (d, 2H, J=6.2 Hz), 8.24 (d, 1H, J=8.3 Hz), 8.09 (d, 1H, J=8.3 HZ), 7.85 (d, 1H, J=7.9 Hz), 7.76 (ddd, 1H, J=8.5, 7, 1Hz), 7.70 (d, 1H, J=8.7 Hz), 7.57 (m, 1H), 7.54 (m, 2H), 7.24 (m, 2H), 7.20 (m, 2H). 5.46 (s, 2H), 3.90 (s, 3H). MS (AP+) m/e 394 (MH+).

Preparation 77

4-(1-(pyridin-4-yl)-1H-imidazol-2-yl)phenol

According to the procedure for preparation of 4-(3-methyl-5-(pyridin-4-yl)-3H-1,2,3-triazol-4-yl)phenol, except that 4:1 dichloromethane:2-propanol was used in place of ethyl acetate to extract the product, 4-(2-(4-methoxyphenyl)-1H-imidazol-1-yl)pyridine (125 mg, 0.5 mmol) was treated with 1.25 mmol of boron tribromide to give 90 mg of a colorless solid. $^1$H NMR (CDCl$_3$, 400 mHz) δ 8.52 (d, 2H, J=6 Hz), 7.14 (m, 2H), 7.11-7.08 (m, 4H), 6.79 (m, 2H), 2.94 (br, 1H).

Preparation 78

4-(2-(4-methoxyphenyl)-1H-imidazol-1-yl)pyridine

Phosphorus pentachloride (572 mg, 2.75 mmol) was added to a mixture of 4-methoxy-N-(pyridin-4-yl)benzamide (626 mg, 2.75 mmol) in phosphorus oxychloride (3 mL) and the mixture was heated a 105° C. oil bath for 4 h. The mixture was concentrated to dryness. To the residue was added 2,2-dimethoxyethylamine (3.1 g) in methanol, and the mixture was stirred at RT. After more than one hour the mixture was partially concentrated to remove most of the methanol, stirred at RT overnight and concentrated to dryness. Isopropyl alcohol (10 mL) and conc. HCl (15 mL) were added and the mixture was heated at 80° C. for 24 h. Solid sodium bicarbonate was added to bring the pH to 7-8, and the mixture was extracted with dichloromethane (3×50 mL) which was dried (sodium sulfate) and concentrated. Chromatography on silica eluted with 25% to 100% ethyl acetate-hexanes gave 130 mg (20%) of a yellow solid. $^1$H NMR (CDCl$_3$, 400 mHz) δ 8.55 (d, 2H, J=6 Hz), 7.22 (d, 2H, J=9Hz), 7.17 (s, 1H), 7.12 (s, 1H), 7.05 (d, 2H, J=6 Hz), 6.75 (d, 2H, J=9 Hz), 3.72 (s, 3H).

Preparation 79

4-methoxy-N-(pyridin-4-yl)benzamide

4-Aminopyridine (1.94 g, 20.6 mmol) was added to a solution of p-anisoyl chloride (3.5 g, 20.6 mmol) and triethylamine (8.6 mL, 62 mmol) in dichloromethane (100 mL) at 0° C. The mixture was stirred 3 h at RT, and then extracted successively with 1N NaOH, water and brine, dried over sodium sulfate, and concentrated. Chromatography on silica (gradient of 30% to 100% ethyl acetate-hexanes) gave 3.8 g (81%) of a colorless solid. $^1$H NMR (CDCl$_3$, 400 mHz) δ 8.49 (m, 2H), 8.19 (br, 1H), 7.85 (m, 2H), 7.59 (m, 2H), 6.95 (m, 2H), 3.85 (s, 3H), MS (AP+) 229 (MH+).

EXAMPLE 81

2-((4-(1-(pyridin-4-yl)-1H-imidazol-2-yl)phenoxy)methyl)quinoline

According to the procedure for preparation of 2-((4-(3-methyl-5-(pyridin-4-yl)-3H-1,2,3-triazol-4-yl)phenoxy)methyl)quinoline, 4-(1-(pyridin-4-yl)-1H-imidazol-2-yl)phenol (90 mg), 2-(chloromethyl)quinoline hydrochloride (81 mg) and cesium carbonate (495 mg) gave 120 mg as an off-white solid (84%). $^1$H NMR (CDCl$_3$, 400 mHz) δ 8.59 (m, 2H), 8.16 (d, 1H, J =8.3 Hz), 8.04 (d, 1H, J=8.3 Hz), 7.79 (d, 1H, J=7.9 Hz), 7.70 (ddd, 1H), 7.60 (d, 1H, J=8.3 Hz), 7.52 (ddd, 1H), 7.28 (m, 2H), 7.22 (d, 1H, J=1 Hz), 7.15 (d, 1H, J=1 Hz), 7.11 (m, 2H), 6.94 (m, 2H), 5.34 (s, 2H). HPLC-MS (system 1) 4.53 min, m/e 379 (MH+).

Preparation 80

4-(1-(4-methoxyphenyl)-1H-imidazol-5-yl)pyridine

4-Methoxyaniline (2.46 g, 20 mmol) and pyridine-4-carboxaldehyde (1.9 mL, 10 mmol) in toluene (110 mL) in a flask attached to a Dean-Stark trap and reflux condensor was heated at reflux. After 40 hours, the reaction was complete by infrared spectral analysis and mass spectral analysis. The toluene was removed via distillation through the Dean-Stark sidearm, the residue was dissolved in methanol (100 mL) and ca. ½ of the crude imine (ca. 10 mmol, 50 mL of methanol solution) was diluted with methanol (20 mL) and 1,2-dimethoxyethane (20 mL). The solution was then treated with potassium carbonate (2.76 g, 20 mmol) and tosylmethylisocyanide (TOSMIC, 2.93 g, 15 mmol) and was heated at reflux for 3 hours. After cooling to room temperature, the solvent was removed in vacuo, and the residue was dissolved in methylene chloride and was washed with brine. The brine layer was extracted with methylene chloride and the combined organic layers were dried (MgSO$_4$), were filtered, and were concentrated in vacuo. The residue was purified by silica gel chromatography with ethyl acetate—hexanes—methanol (80:20:0 to 76:19:5) to afford 1.4 g (56% yield) of the title compound; diagnostic $^{13}$C NMR signals (100 MHz, CDCl$_3$) δ 160.039, 150.161, 141.009, 137.240, 130.839, 129.179, 127.287, 121.597, 115.106, 55.801; MS (AP/Cl) 252.4 (M$^+$H)+.

Preparation 81

4-(1-(4-(benzyloxy)phenyl)-1H-imidazol-5-yl)pyridine

The title compound was prepared using the method described for Preparation 80, substituting 4-benzyloxyaniline for 4-methoxyaniline, and afforded 4-(1-(4-(benzyloxy)phenyl)-1H-imidazol-5-yl)pyridine in 54% yield; diagnostic $^{13}$C NMR signals (100 MHz, CDCl$_3$) δ 159.195, 150.132, 141.001, 137.263, 136.403, 130.892, 130.735, 129.389, 128.932, 128.521, 127.751, 127.317, 121.627, 116.078, 70.637; MS (AP/Cl) 328.4 (M+H)+.

Preparation 82

4-(1-(4-methoxyphenyl)-2-methyl-1H-imidazol-5-yl)pyridine

A solution of diisopropyl amine (0.51 mL, 3.6 mmol) in tetrahydrofuran (12 mL) at −20° C., was treated with n-butyl lithium (2.5 M in hexanes, 1.45 mL, 3.6 mmol) and the solution was stirred for 10 minutes. A solution of Preparation 80 (4-(1-(4-methoxyphenyl)-1H-imidazol-5-yl)pyridine, 730 mg, 2.9 mmol) in tetrahydrofuran was added and the solution became dark orange. The solution was stirred for 30 minutes as the temperature was allowed to rise to 0° C. After cooling to −20° C., methyl iodide (0.54 mL, 8.7 mmol) in tetrahydrofuran (12 mL) was added and the solution was stirred for 30 min at −20° C. and for 2 hr at 23° C. The solvent was removed in vacuo, the residue was diluted with brine and was extracted with ethyl acetate. The organic layer was then dried (MgSO$_4$), was filtered, and was concentrated in vacuo. The residue was purified by silica gel chromatography using ethyl acetate-hexanes-methanol (63:32:5 to 72:18:10) to afford 555 mg (72% yield) of the title compound; diagnostic $^{13}$C NMR signals (100 MHz, CDCl$_3$) δ 160.144, 150.034, 149.197, 137.749, 131.265, 129.463, 128.985, 128.828, 120.849, 115.233, 55.78, 14.203; MS (AP/Cl) 266.4 (M+H)+.

Preparation 83

4-(2-ethyl-1-(4-methoxyphenyl)-1H-imidazol-5-yl)pyridine

The title compound was prepared using the method described for Preparation 82 with ethyl iodide used in the place of methyl iodide and afforded 83% yield of 4-(2-ethyl-1-(4-methoxyphenyl)-1H-imidazol-5-yl)pyridine; diagnostic $^{13}$C NMR signals (100 MHz, CDCl$_3$) δ 160.144, 150.147, 149.990, 137.786, 129.239, 129.037, 128.992, 121.597, 120.909, 115.181, 55.771, 21.097, 12.348; MS (AP/Cl) 280.5 (M+H)+.

Preparation 84

4-(5-(pyridin-4-yl)-1H-imidazol-1-yl)phenol

A solution of Preparation 81 (4-(1-(4-(benzyloxy)phenyl)-1H-imidazol-5-yl)pyridine, 2 g, 6.1 mmol) and anisole (13 mL, 122 mmol) in trifluoracetic acid (50 mL) was heated at 75° C. for 24 h. The solvent was removed in vacuo and the residue was purified via silica gel chromatography with chloroform-methanol-ammonium hydroxide (94:5:1) to afford 1.27 g (88%) of the title compound; diagnostic $^{13}$C NMR signals (100 MHz, CDCl$_3$) δ 158.402, 149.145, 141.061, 138.018, 120.600, 129.822, 127.482, 127.370, 121.933, 116.497; MS (AP/Cl) 238.3 (M+H)+.

Preparation 85

4-(2-methyl-5-(pyridin-4-yl)-1H-imidazol-1-yl)phenol

A solution of boron tribromide (1 M in methylene chloride, 2.1 mL, 2.1 mmol) was added dropwise to a solution of Preparation 82 (4-(1-(4-methoxyphenyl)-2-methyl-1H-imidazol-5-yl)pyridine, 220 mg, 0.83 mmol) in methylene chloride (5 mL) at 0° C. After stirring at 23° C. for 24 h, aqueous sodium hydroxide solution (1 N, 15 mL) was added and the mixture was stirred at 23° C. for 1 h. The pH was adjusted to 7 by the addition of aqueous hydrochloric acid (1N), the mixture was extracted with methylene chloride/isopropanol (4:1, 3×30 mL), the combined organic layers were dried (MgSO$_4$), were filtered, and were concentrated in vacuo. The residue was purified by silica gel chromatography using chloroform-methanol (20:1 to 10:1) to afford 150 mg (72% yield) of the title compound; diagnostic $^{13}$C NMR signals (100 MHz, CDCl$_3$) δ 159.337, 149.548, 149.302, 138.302, 131.131, 128.760, 128.170, 127.310, 121.163, 117.237, 13.881; MS (AP/Cl) 252.4 (M+H)+.

Preparation 86

4-(2-ethyl-5-(pyridin-4-yl)-1H-imidazol-1-yl)phenol

The title compound was prepared using Preparation 4 as the starting material and the method for Preparation 85. This yielded 4-(2-ethyl-5-(pyridin-4-yl)-1H-imidazol-1-yl)phenol in 70% yield; diagnostic $^{13}$C NMR signals (100 MHz, CD$_3$OD/CDCl$_3$) δ 158.574, 149.182, 149.002, 138.511, 130.877, 128.895, 128.200, 127.340, 121.253, 116.692, 20.656, 12.020; MS (AP/Cl) 266.4 (M+H)+.

EXAMPLE 82

2-((4-(5-(pyridin-4-yl)-1H-imidazol-1-yl)phenoxy)methyl)quinoline

A mixture of Preparation 84 (4-(5-(pyridin-4-yl)-1H-imidazol-1-yl)phenol, 95 mg, 0.4 mmol), 2-chloromethylquinoline hydrochloride (128 mg, 0.6 mmol), and cesium carbonate (391 mg, 1.2 mmol) in dimethylsulfoxide (2 mL) was stirred at 23° C. for 24 h. The mixture was diluted with ethyl acetate/n-butanol (100 mL/5 mL), was washed with water and then brine, and the organic layer was dried (MgSO$_4$), was filtered, and was concentrated in vacuo. The residue was purified by silica gel chromatography using chloroform/methanol (50:1) to afford 150 mg (99% yield) of the title compound; diagnostic $^{13}$C NMR signals (100 MHz, CDCl$_3$) δ 158.940, 157.116, 149.990, 147.836, 141.054, 137.405, 130.989, 130.204, 129.650, 129.239, 127.953, 127.871, 127.392, 127.011, 121.627, 119.324, 116.198, 71.990; MS (AP/Cl) 379.4 (M+H)+.

EXAMPLE 83

2-((4-(2-methyl-5-(pyridin-4-yl)-1H-imidazol-1-yl)phenoxy)methyl)quinoline

The title compound was prepared using Preparation 85 and the method described in Example 82; 88% yield; diagnostic $^{13}$C NMR signals (100 MHz, CDCl$_3$) δ 159.060, 157.078, 150.004, 147.836, 137.689, 137.397, 130.204, 129.934, 129.239, 128.962, 127.968, 127.871, 127.385, 127.011, 120.886, 119.354, 116.273, 71.975, 14.225; MS (AP/Cl) 393.49 (M+H)+.

EXAMPLE 84

2-((4-(2-ethyl-5-(pyridin-4-yl)-1H-imidazol-1-yl)phenoxy)methyl)quinoline

The title compound was prepared using Preparation 86 and the method described in Example 82; 92% yield; diagnostic $^{13}$C NMR signals (100 MHz, CDCl$_3$) δ 159.090, 157.078, 150.147, 149.930, 147.836, 137.734, 137.405, 130.211, 129.680, 129.232, 129.127, 128.970, 127.968, 127.886, 127.392, 127.018, 120.961, 119.354, 116.243, 71.968, 21.090, 12.333; MS (AP/Cl) 407.5 (M+H)+.

Preparation 87

N-(4-methoxyphenyl)isonicotinamide

A solution of p-anisidine (2.46 g, 20 mmol) and triethylamine (13.9 mL, 100 mmol) in ethyl acetate (200 mL) was treated with isonicotinic acid (2.46 g, 20 mmol) followed by 1-propanephosphonic acid cyclic anhydride (50% in ethyl acetate, 15.1 mL, 24 mmol). After stirring at 23° C. for 4 h, the reaction mixture was diluted with ethyl acetate, was washed with water and with brine, and the organic layer was dried (MgSO$_4$), was filtered, and was concentrated in vacuo. Purification by silica gel chromatography with chloroform-methanol (40:1) gave 4 g (88% yield) of the title compound; diagnostic $^{13}$C NMR signals (100 MHz, CD$_3$OD/CDCl$_3$) δ 164.825, 157.213, 149.758, 143.349, 130.989, 123.085, 122.068, 55.285; MS (AP/Cl) 229.3 (M+H)+.

Preparation 88

4-(1-(4-methoxyphenyl)-1H-imidazol-2-yl)pyridine

Preparation 87 (N-(4-methoxyphenyl)isonicotinamide, 1 g, 4.39 mmol) was dissolved in phosphorous oxychloride (POCl$_3$) (5 mL) then phosphorous pentachloride (913 mg, 4.39 mmol) was added. The mixture was heated at 120° C. for 4 h. The POCl$_3$ was removed in vacuo, aminoacetaldehyde dimethyl acetal (9.5 mL, 87.8 mmol) and isopropanol (10 mL) were added, and the mixture was stirred at 23° C. for ca. 16 h. The reaction mixture was concentrated in vacuo and concentrated hydrochloric acid (36.5%, 25 mL) in isopropanol (15 mL) was added. The reaction mixture was heated at 90° C. for 24 h. After cooling to 23° C., aqueous sodium hydroxide (1N) and aqueous sodium bicarbonate were added to obtain pH=8. The mixture was extracted with methylene chloride, was dried (MgSO$_4$), and was filtered and concentrated in vacuo. The residue was purified by silica gel chromatography with ethyl acetate/hexanes/methanol (80:20:0 to 76:19:5) to afford 811 mg (74% yield) of the title compound; diagnostic $^{13}$C NMR signals (100 MHz, CDCl$_3$) δ 160.069, 149.952, 144.142, 137.853, 131.004, 129.882, 127.414, 124.977, 122.195, 115.114, 55.808; MS (AP/Cl) 252.4 (M+H)+.

Preparation 89

4-(2-(pyridin-4-yl)-1H-imidazol-1-yl)phenol

The title compound was prepared using the method outlined in Preparation 85 with the substitution of Preparation 88 for Preparation 82; 86% yield; diagnostic $^{13}$C NMR signals (100 MHz, CD$_3$OD/CDCl$_3$) δ 158.372, 149.145, 143.641, 138.257, 129.232, 128.985, 127.347, 125.418, 122.666, 116.505; MS (AP/Cl) 238.4 (M+H)+.

EXAMPLE 85

2-((4-(2-(pyridin-4-yl)-1H-imidazol-1-yl)phenoxy)methyl)quinoline

The title compound was prepared using the method outlined in Example 82 with the substitution of Preparation 89 for Preparation 84; 98% yield; diagnostic $^{13}$C NMR signals (100 MHz, CDCl$_3$) δ 158.948, 157.108, 149.847, 147.814, 137.868, 137.420, 131.445, 130.226, 129.942, 127.968, 127.871, 127.534, 127.026, 124.954, 122.247, 119.339, 116.190, 71.968; MS (AP/Cl) 379.4 (M+H)+.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A compound of formula I or a pharmaceutical acceptable salt thereof,

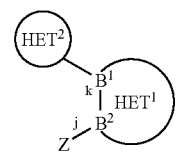

I wherein Z is

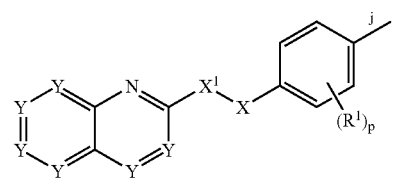

$R^1$ is each independently selected from a group consisting of hydrogen or halogen;
$R^2$ is hydrogen or C$_1$ to C$_8$ alkyl;
HET$^1$ is 2,3-pyrazole which may be optionally substituted with at least one $R^4$;
$R^4$ is C$_1$ to C$_8$ alkyl, C$_3$ to C$_8$ haloalkyl, or a C$_1$ to C$_8$ alkyl substituted with a substituent selected from a group consisting of —OR$^8$ and —NR$^8$R$^8$, wherein R$^8$ is independently selected from a group consisting of hydrogen and C$_1$ to C$_8$ alkyl;
HET$^2$ is a 4-pyridyl, which may be optionally substituted with at least one $R^5$;
$R^5$ is independently selected from a group consisting of halogen, C$_1$ to C$_8$ alkyl and —NR$^7$R$^7$;
B$^1$ and B$^2$ are adjacent atoms in Het$^1$ and are both carbon;
bond j is a covalent bond between Z and B$^2$;
bond k is a bond in Het$^1$ between B$^1$ and B$^2$;
X is oxygen or C(R$^2$)$_2$ and X$^1$ is C(R$^2$)$_2$;
Y is carbon substituted with R$^8$;
wherein each R$^6$ is independently selected from a group consisting of hydrogen, halogen, hydroxyl, C$_1$ to C$_8$ alkoxy and NR$^7$R$^7$;
wherein each R$^7$ is independently selected from a group consisting of hydrogen and C$_1$-C$_8$alkyl; p is 1, 2 or 3.

2. The compound of claim 1 or a pharmaceutical acceptable salt thereof, wherein the compound of formula I has the following structure:

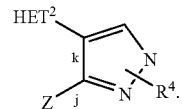

3. The compound of claim 1, or a pharmaceutical acceptable salt thereof, wherein the compound of formula I has the following structure:

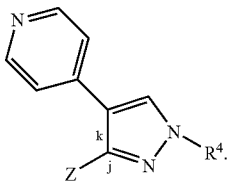

4. The compound of claim 1, or a pharmaceutical acceptable salt thereof wherein $X^1$ is $C(R^2)_2$ and X is oxygen.

5. The compound of claim 1, wherein said compound is selected from a group consisting of:
   2-[4-(4-Pyridin-4-yl-2H-pyrazol-3-yl)-phenoxymethyl]-quinoline;
   2-[4-(2-Methyl-4-pyridin4-yl-2H-pyrazol-3-yl)-phenoxymethyl]-quinoline;
   2-[4-(1-Methyl-4-pyridin4-yl-1H-pyrazol-3-yl)-phenoxymethyl]-quinoline;
   2-[4-(2-Ethyl-4-pyridin4-yl-2H-pyrazol-3-yl)-phenoxymethyl]-quinoline;
   2-[4-(1-Ethyl-4-pyridin4-yl-1H-pyrazol-3-yl )-phenoxymethyl]-quinoline;
   Dimethyl-(2-{4-pyridin4-yl-3-[4-(quinolin-2-ylmethoxy)-phenyl]-pyrazol-1-yl}-ethyl)-amine;
   Dimethyl-(2-{4-pyridin-4-yl-5-[4-(quinolin-2-ylmethoxy)-phenyl]-pyrazol-1-yl}-ethyl)-amine;
   1-{4-Pyridin-4-yl-3-[4-(quinolin-2-ylmethoxy)-phenyl]-pyrazol-1-yl}-propan-2-ol;
   1-{4-Pyridin-4-yl-5-[4-(quinolin-2-ylmethoxy)-phenyl]-pyrazol-1-yl}-propan-2-ol;
   2-[4-(2-Isopropyl-4-pyridin-4-yl-2H-pyrazol-3-yl)-phenoxymethyl]-quinoline;
   7-Chloro-2-[4-(1-methyl4-pyridin-4-yl-1H-pyrazol-3-yl )-phenoxymethyl]-quinoline hydrogen chloride;
   6-Fluoro-2-[4-(1-methyl-4-pyridin-4-yl-1H-pyrazol-3-yl)-phenoxymethyl]-quinoline hydrogen chloride;
   2-[2-Fluoro4-(4-pyridin-4-yl-1H-pyrazol-3-yl)-phenoxymethyl]-quinoline;
   2-[2-Fluoro4-(1-methyl-4-pyridin-4-yl-1H-pyrazol-3-yl)-phenoxymethyl]-quinoline;
   2-[2,3-Difluoro-4-(1-methyl-4-pyridin-4-yl-1H-pyrazol-3-yl)-phenoxymethyl]-quinoline;
   2-[3-Fluoro-4-(4-pyridin-4-yl-1H-pyrazol-3-yl)-phenoxymethyl]-quinoline;
   2-[4-(5-Pyridin-4-yl-1H-pyrazol-4-yl)-phenoxymethyl]-quinoline;
   2-[4-(1-Methyl-5-pyridin-4-yl-1H-pyrazol-4-yl)-phenoxymethyl]-quinoline 2-[4-(1-Methyl-3-pyridin-4-yl-1H-pyrazol-4-yl)-phenoxymethyl]-quinoline;
   2-Methyl-1-{4-pyridin-4-yl-3-[4-(quinolin-2-ylmethoxy)-phenyl]-pyrazol-1-yl}-propan-2-ol;
   2-Methyl-1-{4-pyridin-4-yl-5-[4-(quinolin-2-ylmethoxy)-phenyl]-pyrazol-1-yl}-propan-2-ol;
   (R)-1-{4-Pyridin-4-yl-3-[4-(quinolin-2-ylmethoxy)-phenyl]-pyrazol-1-yl}-propan-2-ol;
   (S)-1-{4-Pyridin-4-yl-3-[4-(quinolin-2-ylmethoxy)-phenyl]-pyrazol-1-yl}-propan-2-ol;
   2-[4-(1-Isopropyl-4-pyridin-4-yl-1H-pyrazol-3-yl)-phenoxymethyl]-quinoline;
   2-[4-(1-Isobutyl-4-pyridin-4-yl-1H-pyrazol-3-yl)-phenoxymethyl]-quinoline;
   2-{2-[4-(4-Pyridin-4-yl-2H-pyrazol-3-yl)-phenyl]-ethyl}-quinoline;
   2-{2-[4-(1-Methyl-4-pyridin-4-yl-1H-pyrazol-3-yl)-phenyl]-ethyl}-quinoline;
   2-{4-[4-(2-Chloro-pyridin-4-yl)-1H-pyrazol-3-yl]-phenoxymethyl}-quinoline;
   2-{4-[4-(2-Chloro-pyridin-4-yl)-1-methyl-1H-pyrazol-3-yl]-phenoxymethyl}-quinoline;
   8-Methoxy-2-[4-(1-methyl-4-pyridin-4-yl-1H-pyrazol-3-yl)-phenoxymethyl]-quinoline;
   2-[3-Fluoro4-(1-methyl-4-pyridin-4-yl-1H-pyrazol-3-yl)-phenoxymethyl]-quinoline;
   4-Chloro-2-[4-(1-methyl-4-pyridin-4-yl-1H-pyrazol-3-yl)-phenoxymethyl]-quinoline;
   4-Methoxy-2-[4-(1-methyl-4-pyridin-4-yl-1H-pyrazol-3-yl)-phenoxymethyl]-quinoline;
   Dimethyl-{2-[4-(1-methyl-4-pyridin-4-yl-1H-pyrazol-3-yl )-phenoxymethyl]-quinolin-4-yl}-amine;
   2-[4-(1-Methyl-4-pyridin-4-yl-1H-pyrazol-3-yl)-benzyloxy]-quinoline di-succinic acid;
   2-((4-(3-Methyl-4-(pyridin-4-yl)-1H-pyrazol-5-yl)phenoxy)methyl)quinoline;
   2-((4-(1,3-dimethyl-4-(pyridin-4-yl)-1H-pyrazol-5-yl)phenoxy)methyl)quinoline;
   2-((4-(1,5-dimethyl-4-(pyridin-4-yl)-1H-pyrazol-3-yl)phenoxy)methyl)quinoline;
   2-(1-(4-(1-methyl-4-(pyridin-4-yl)-1H-pyrazol-3-yl)phenoxy)ethyl)quinoline;
   and pharmaceutical acceptable salts thereof.

6. The compound of claim 1, wherein said compound is selected from a group consisting of:
   2-{4-[-Pyridin-4-yl-2-(2,2,2-trifluoro-ethyl)-2H-pyrazol-3-yl]-phenoxymethyl}-quinoline;
   2-{4-[-Pyridin-4-yl-1-(2,2,2-trifluoro-ethyl)-1H-pyrazol-3-yl]-phenoxymethyl}-quinoline;
   2-{3-Fluoro-4-[4-pyridin-4-yl-1-(2,2,2-trifluoro-ethyl)-1H-pyrazol-3-yl]-phenoxymethyl}-quinoline;
   and pharmaceutical acceptable salts thereof.

7. A pharmaceutical composition comprising an a compound of formula I according to claim 1 and a pharmaceutical acceptable carrier.

8. The compound of claim 1, wherein said compound is:
   2-[-4-(4-Pyridin-4-yl-2H-pyrazol-3-yl)-phenoxymethyl]-quinoline or a pharmaceutical acceptable salt thereof.

9. The compound of claim 1, wherein said compound is:
   2-[4-(1-Methyl-4-pyridin-4yl-1H-pyrazol-3-yl)-phenoxymethyl]-quinoline or a pharmaceutical acceptable salt thereof.

* * * * *